United States Patent
Sampath et al.

(10) Patent No.: US 10,366,787 B2
(45) Date of Patent: Jul. 30, 2019

(54) PHYSIOLOGICAL ALARM THRESHOLD DETERMINATION

(71) Applicant: MASIMO CORPORATION, Irvine, CA (US)

(72) Inventors: Anand Sampath, Corona, CA (US); Bilal Muhsin, San Clemente, CA (US); Jad Adel Wafeeq, Mission Viejo, CA (US)

(73) Assignee: MASIMO CORPORATION, Irvine, CA (US)

( * ) Notice: Subject to any disclaimer, the term of this patent is extended or adjusted under 35 U.S.C. 154(b) by 8 days.

(21) Appl. No.: 15/894,423

(22) Filed: Feb. 12, 2018

(65) Prior Publication Data

US 2018/0174679 A1    Jun. 21, 2018

Related U.S. Application Data

(60) Continuation of application No. 14/975,564, filed on Dec. 18, 2015, which is a division of application No.
(Continued)

(51) Int. Cl.
G06F 19/00    (2018.01)
G16H 10/60    (2018.01)
(Continued)

(52) U.S. Cl.
CPC .......... G16H 40/40 (2018.01); G06F 3/0482 (2013.01); G06F 19/00 (2013.01);
(Continued)

(58) Field of Classification Search
CPC ........ G16H 40/40; G16H 40/63; G16H 10/60; G16F 40/20; G16F 40/00; G06F 19/3418; G06F 3/0482; G06F 19/00
See application file for complete search history.

(56) References Cited

U.S. PATENT DOCUMENTS 3,646,606 A    2/1972    Buxton et al.
4,051,522 A    9/1977    Healy et al.
(Continued)

FOREIGN PATENT DOCUMENTS

CA    2674654 A1    10/2009
EP    1443480 A     8/2004
(Continued)

OTHER PUBLICATIONS

US 8,845,543 B2, 09/2014, Diab et al. (withdrawn)
(Continued)

*Primary Examiner* — Joy Chng

(74) *Attorney, Agent, or Firm* — Knobbe, Martens, Olson & Bear, LLP

(57) ABSTRACT

A method of reducing nuisance alarms for a physiological parameter at a specific care unit by determining an alarm threshold optimized for the care unit, the care unit including a plurality of patients being monitored for the physiological parameter. Measured physiological parameters for the plurality of patients is measured and provided to a threshold recommendation system. The threshold recommendation system determines a recommended parameter specific alarm threshold value calculated to reduce false alarms by determining how many alarms are generated at each of a range of threshold values and choosing a threshold value from the range of threshold values that reduces a number of false alarms without unacceptably increasing missed true alarms for said patient measurements.

26 Claims, 56 Drawing Sheets

Related U.S. Application Data

12/717,081, filed on Mar. 3, 2010, now Pat. No. 9,218,454.

(60) Provisional application No. 61/296,439, filed on Jan. 19, 2010, provisional application No. 61/209,147, filed on Mar. 4, 2009.

(51) Int. Cl.
*G16H 40/00* (2018.01)
*G16H 40/20* (2018.01)
*G16H 40/40* (2018.01)
*G16H 40/63* (2018.01)
*G06F 3/0482* (2013.01)

(52) U.S. Cl.
CPC ......... *G06F 19/3418* (2013.01); *G16H 10/60* (2018.01); *G16H 40/00* (2018.01); *G16H 40/20* (2018.01); *G16H 40/63* (2018.01)

(56) References Cited

U.S. PATENT DOCUMENTS

| | | |
|---|---|---|
| 4,216,462 A | 8/1980 | McGrath et al. |
| 4,237,344 A | 12/1980 | Moore |
| 4,356,475 A | 10/1982 | Nuemann et al. |
| 4,674,085 A | 6/1987 | Aranguren et al. |
| 4,838,275 A | 6/1989 | Lee |
| 4,852,570 A | 8/1989 | Levine |
| 4,887,260 A | 12/1989 | Carden et al. |
| 4,916,444 A | 4/1990 | King |
| 4,920,339 A | 4/1990 | Friend et al. |
| 4,960,128 A | 10/1990 | Gordon et al. |
| 4,964,408 A | 10/1990 | Hink et al. |
| 5,038,800 A | 8/1991 | Oba |
| 5,041,187 A | 8/1991 | Hink et al. |
| 5,061,916 A | 10/1991 | French et al. |
| 5,069,213 A | 12/1991 | Polczynski |
| 5,163,438 A | 11/1992 | Gordon et al. |
| 5,278,627 A | 1/1994 | Aoyagi |
| 5,296,688 A | 3/1994 | Hamilton et al. |
| 5,319,355 A | 6/1994 | Russek |
| 5,319,363 A | 6/1994 | Welch et al. |
| D348,463 S | 7/1994 | Scheid et al. |
| 5,331,549 A | 7/1994 | Crawford, Jr. |
| 5,337,744 A | 8/1994 | Branigan |
| 5,341,805 A | 8/1994 | Stavridi et al. |
| 5,348,008 A | 9/1994 | Bornn et al. |
| D353,195 S | 12/1994 | Savage et al. |
| D353,196 S | 12/1994 | Savage et al. |
| 5,375,604 A | 12/1994 | Kelly et al. |
| 5,377,676 A | 1/1995 | Vari et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,462,051 A | 10/1995 | Oka et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| D375,792 S | 11/1996 | Hillman et al. |
| 5,576,952 A | 11/1996 | Stutman et al. |
| 5,579,001 A | 11/1996 | Dempsey et al. |
| 5,579,775 A | 12/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,682,803 A | 11/1997 | Boianjiu |
| 5,685,299 A | 11/1997 | Diab et al. |
| 5,687,734 A | 11/1997 | Dempsey et al. |
| 5,694,940 A | 12/1997 | Unger et al. |
| D390,666 S | 2/1998 | Lagerlof |
| D392,639 S | 3/1998 | Tamura et al. |
| 5,724,580 A | 3/1998 | Levin et al. |
| D393,830 S | 4/1998 | Tobler et al. |
| 5,743,262 A | 4/1998 | Lepper, Jr. et al. |
| 5,748,103 A | 5/1998 | Flach et al. |
| 5,751,957 A | 5/1998 | Hiroya et al. |
| 5,752,917 A | 5/1998 | Fuchs |
| 5,758,079 A | 5/1998 | Ludwig et al. |
| 5,758,644 A | 6/1998 | Diab et al. |
| 5,760,910 A | 6/1998 | Lepper, Jr. et al. |
| 5,767,791 A | 6/1998 | Stoop et al. |
| 5,769,785 A | 6/1998 | Diab et al. |
| 5,772,585 A | 6/1998 | Lavin et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,822,544 A | 10/1998 | Chaco et al. |
| 5,823,950 A | 10/1998 | Diab et al. |
| 5,830,131 A | 11/1998 | Caro et al. |
| 5,833,618 A | 11/1998 | Caro et al. |
| D402,805 S | 12/1998 | Nagano et al. |
| 5,855,550 A | 1/1999 | Lai et al. |
| 5,860,919 A | 1/1999 | Kiani-Azarbayjany et al. |
| 5,865,736 A * | 2/1999 | Baker, Jr. ........... A61B 5/02455 600/323 |
| 5,871,451 A | 2/1999 | Unger et al. |
| 5,877,675 A | 3/1999 | Rebstock et al. |
| 5,890,929 A | 4/1999 | Mills et al. |
| D409,195 S | 5/1999 | Halstead et al. |
| 5,903,889 A | 5/1999 | de la Huerga et al. |
| 5,904,654 A | 5/1999 | Wohltmann et al. |
| 5,919,134 A | 7/1999 | Diab |
| 5,924,074 A | 7/1999 | Evans |
| 5,934,925 A | 8/1999 | Tobler et al. |
| 5,940,182 A | 8/1999 | Lepper, Jr. et al. |
| 5,942,986 A | 8/1999 | Shabot et al. |
| 5,960,431 A | 9/1999 | Choy |
| D414,870 S | 10/1999 | Saltzstein et al. |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,024,699 A | 2/2000 | Surwit et al. |
| 6,027,452 A | 2/2000 | Flaherty et al. |
| 6,036,642 A | 3/2000 | Diab et al. |
| D423,504 S | 4/2000 | Nishii et al. |
| 6,045,509 A | 4/2000 | Caro et al. |
| 6,057,758 A | 5/2000 | Dempsey et al. |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,110,522 A | 8/2000 | Lepper, Jr. et al. |
| 6,112,224 A | 8/2000 | Peifer et al. |
| 6,112,226 A | 8/2000 | Weaver et al. |
| 6,124,597 A | 9/2000 | Shehada |
| 6,128,521 A | 10/2000 | Marro et al. |
| 6,129,675 A | 10/2000 | Jay |
| 6,139,494 A | 10/2000 | Cairnes |
| 6,144,868 A | 11/2000 | Parker |
| 6,151,516 A | 11/2000 | Kiani-Azarbayjany et al. |

(56) References Cited

U.S. PATENT DOCUMENTS

| | | | |
|---|---|---|---|
| 6,152,754 A | 11/2000 | Gerhardt et al. |
| 6,157,850 A | 12/2000 | Diab et al. |
| 6,165,005 A | 12/2000 | Mills et al. |
| 6,168,563 B1 | 1/2001 | Brown |
| 6,171,237 B1 | 1/2001 | Avitall et al. |
| 6,184,521 B1 | 2/2001 | Coffin, IV et al. |
| 6,206,830 B1 | 3/2001 | Diab et al. |
| 6,221,012 B1 | 4/2001 | Maschke |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,661 B1 | 6/2001 | Schluess et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| D450,679 S | 11/2001 | Soh |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| D452,012 S | 12/2001 | Phillips |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,360,114 B1 | 3/2002 | Diab et al. |
| 6,364,834 B1 | 4/2002 | Reuss et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,380,853 B1 | 4/2002 | Long et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,406,426 B1 | 6/2002 | Reuss et al. |
| 6,424,249 B1 | 7/2002 | Houvener |
| 6,430,437 B1 | 8/2002 | Marro |
| 6,430,525 B1 | 8/2002 | Weber et al. |
| 6,440,067 B1 | 8/2002 | DeLuca et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,535,132 B2 | 3/2003 | Walters et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,678,703 B2 | 1/2004 | Rothschild et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,749,556 B2 | 6/2004 | Russ |
| 6,749,566 B2 | 6/2004 | Russ |
| 6,760,607 B2 | 7/2004 | Al-Ali |
| 6,770,028 B1 | 8/2004 | Ali et al. |
| 6,771,994 B2 | 8/2004 | Kiani et al. |
| 6,782,093 B2 | 8/2004 | Uckun |
| 6,784,797 B2 | 8/2004 | Smith et al. |
| 6,792,300 B1 | 9/2004 | Diab et al. |
| 6,804,656 B1 | 10/2004 | Rosenfeld |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,836,890 B1 | 12/2004 | Watts, Jr. et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,915,135 B1 | 7/2005 | McKee et al. |
| 6,920,345 B2 | 7/2005 | Al-Ali et al. |
| 6,928,370 B2 | 8/2005 | Anuzis et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,028,182 B1 | 4/2006 | Killcommons |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,916 B2 | 5/2006 | Flaherty et al. |
| 7,044,918 B2 | 5/2006 | Diab |
| 7,048,687 B1 | 5/2006 | Reuss et al. |
| 7,062,251 B2 | 6/2006 | Birkett et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| D539,265 S | 3/2007 | Tompkins et al. |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |

(56) References Cited

U.S. PATENT DOCUMENTS

| | | |
|---|---|---|
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,242,307 B1 | 7/2007 | LeBlond et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,256,429 B2 | 8/2007 | Schurman et al. |
| 7,256,708 B2 | 8/2007 | Rosenfeld |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| D554,616 S | 11/2007 | Pierce |
| 7,292,883 B2 | 11/2007 | De Felice et al. |
| 7,295,866 B2 | 11/2007 | Al-Ali |
| 7,307,543 B2 | 12/2007 | Rosenfeld et al. |
| 7,315,825 B2 | 1/2008 | Rosenfeld et al. |
| 7,321,862 B2 | 1/2008 | Rosenfeld et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,382,247 B2 | 6/2008 | Welch et al. |
| 7,383,070 B2 | 6/2008 | Diab et al. |
| 7,395,216 B2 | 7/2008 | Rosenfeld |
| 7,411,509 B2 | 8/2008 | Rosenfeld |
| 7,415,297 B2 | 8/2008 | Al-Ali et al. |
| 7,421,367 B2 | 9/2008 | Nye |
| 7,423,533 B1 | 9/2008 | LeBlond et al. |
| 7,427,920 B2 | 9/2008 | Martin et al. |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,570,152 B2 | 8/2009 | Smith et al. |
| 7,596,398 B2 | 9/2009 | Al-Ali et al. |
| D603,836 S | 11/2009 | Hibbard et al. |
| 7,618,375 B2 | 11/2009 | Flaherty |
| D606,659 S | 12/2009 | Kiani et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| D614,305 S | 4/2010 | Al-Ali et al. |
| 7,706,896 B2 | 4/2010 | Music et al. |
| RE41,317 E | 5/2010 | Parker |
| 7,729,733 B2 | 6/2010 | Al-Ali et al. |
| 7,734,320 B2 | 6/2010 | Al-Ali |
| 7,734,476 B2 | 6/2010 | Wildman et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,778,851 B2 | 8/2010 | Schoenberg |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,831,450 B2 | 11/2010 | Schoenberg |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,855,651 B2 | 12/2010 | LeBlond et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,933,642 B2 | 4/2011 | Istvan et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 7,991,625 B2 | 8/2011 | Rosenfeld et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,086,708 B2 | 12/2011 | Breitgand et al. |
| 8,094,029 B2 | 1/2012 | Ortiz et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,170,887 B2 | 5/2012 | Rosenfeld |

(56) References Cited

U.S. PATENT DOCUMENTS

| | | |
|---|---|---|
| 8,175,672 B2 | 5/2012 | Parker |
| 8,175,895 B2 | 5/2012 | Rosenfeld |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| D665,504 S | 8/2012 | Arimitsu |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,326,649 B2 | 12/2012 | Rosenfeld |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,358,214 B2 | 1/2013 | Amigo |
| 8,359,080 B2 | 1/2013 | Diab et al. |
| 8,364,223 B2 | 1/2013 | Al-Ali et al. |
| 8,364,226 B2 | 1/2013 | Diab et al. |
| D676,136 S | 2/2013 | Arimitsu |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,620,678 B2 | 12/2013 | Gotlib |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |

(56) References Cited

U.S. PATENT DOCUMENTS

| | | |
|---|---|---|
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |

(56) References Cited

U.S. PATENT DOCUMENTS

| | | |
|---|---|---|
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Daivi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 2001/0040512 A1 | 11/2001 | Hines et al. |
| 2001/0046366 A1 | 11/2001 | Susskind |
| 2002/0013518 A1* | 1/2002 | West .............. G16H 40/20 600/300 |
| 2002/0042723 A1 | 4/2002 | Rice et al. |
| 2002/0097277 A1 | 7/2002 | Pitroda |
| 2002/0167699 A1 | 11/2002 | Verplaetse et al. |
| 2002/0177758 A1 | 11/2002 | Schoenberg et al. |
| 2002/0198473 A1 | 12/2002 | Kumar et al. |
| 2003/0002653 A1 | 1/2003 | Uckun |
| 2003/0052787 A1 | 3/2003 | Zerhusen et al. |
| 2003/0058838 A1 | 3/2003 | Wengrovitz |
| 2003/0063010 A1 | 4/2003 | Smith et al. |
| 2004/0001101 A1 | 1/2004 | Trajkovic et al. |
| 2004/0002637 A1 | 1/2004 | Huang et al. |
| 2004/0102683 A1 | 5/2004 | Khanuja et al. |
| 2004/0127774 A1 | 7/2004 | Moore et al. |
| 2004/0133087 A1 | 7/2004 | Ali et al. |
| 2004/0143677 A1 | 7/2004 | Novak |
| 2004/0148308 A1 | 7/2004 | Rajan et al. |
| 2004/0167804 A1 | 8/2004 | Simpson et al. |
| 2004/0172222 A1 | 9/2004 | Simpson et al. |
| 2004/0172301 A1 | 9/2004 | Mihai et al. |
| 2004/0203895 A1 | 10/2004 | Balasuriya |
| 2005/0004953 A1 | 1/2005 | Kurase |
| 2005/0055242 A1 | 3/2005 | Bello et al. |
| 2005/0065851 A1 | 3/2005 | Aronoff et al. |
| 2005/0125256 A1 | 6/2005 | Schoenberg |
| 2005/0165519 A1 | 7/2005 | Ariyur et al. |
| 2005/0179536 A1 | 8/2005 | Lederer |
| 2005/0206518 A1 | 9/2005 | Welch et al. |
| 2005/0231374 A1 | 10/2005 | Diem et al. |
| 2005/0232421 A1 | 10/2005 | Simons et al. |
| 2005/0242946 A1 | 11/2005 | Hubbard, Jr. et al. |
| 2005/0251792 A1 | 11/2005 | Smith |
| 2005/0267655 A1 | 12/2005 | Gessner |
| 2006/0004745 A1 | 1/2006 | Kuhn et al. |
| 2006/0047681 A1 | 3/2006 | Black et al. |
| 2006/0047682 A1 | 3/2006 | Black et al. |
| 2006/0080140 A1 | 4/2006 | Buttner et al. |
| 2006/0129713 A1 | 6/2006 | Xie |
| 2006/0135858 A1 | 6/2006 | Nidd et al. |
| 2006/0149597 A1 | 7/2006 | Powell et al. |
| 2006/0161054 A1 | 7/2006 | Reuss et al. |
| 2006/0224326 A1 | 10/2006 | St. Ores et al. |
| 2006/0237427 A1 | 10/2006 | Logan |
| 2006/0238333 A1 | 10/2006 | Welch et al. |
| 2006/0253042 A1 | 11/2006 | Stahmann et al. |
| 2006/0253301 A1 | 11/2006 | Simms et al. |
| 2006/0288095 A1 | 12/2006 | Torok et al. |
| 2006/0293571 A1 | 12/2006 | Bao et al. |
| 2006/0294092 A1 | 12/2006 | Giang et al. |
| 2007/0032714 A1* | 2/2007 | Mannheimer ...... A61B 5/02455 600/323 |
| 2007/0073555 A1 | 3/2007 | Buist |
| 2007/0075965 A1 | 4/2007 | Huppi et al. |
| 2007/0106126 A1 | 5/2007 | Mannheimer et al. |
| 2007/0109098 A1 | 5/2007 | Siemon et al. |
| 2007/0129983 A1 | 6/2007 | Scherpbier et al. |
| 2007/0136102 A1 | 6/2007 | Rodgers |
| 2007/0180140 A1 | 8/2007 | Welch et al. |
| 2007/0213599 A1 | 9/2007 | Siejko et al. |
| 2007/0239377 A1 | 10/2007 | Reiner |
| 2007/0245158 A1 | 10/2007 | Giobbi et al. |
| 2007/0266389 A1 | 11/2007 | Ganguly et al. |
| 2007/0273504 A1 | 11/2007 | Tran |
| 2007/0279211 A1 | 12/2007 | Fenske et al. |
| 2007/0282478 A1 | 12/2007 | Al-Ali et al. |
| 2008/0004499 A1 | 1/2008 | Davis |
| 2008/0059556 A1 | 3/2008 | Greenspan et al. |
| 2008/0088414 A1 | 4/2008 | Suga et al. |
| 2008/0157980 A1* | 7/2008 | Sachanandani ...... A61B 5/0031 340/573.1 |
| 2008/0174551 A1 | 7/2008 | Ishibashi |
| 2008/0183054 A1* | 7/2008 | Kroeger .................. G06F 19/00 600/301 |
| 2008/0189783 A1 | 8/2008 | Music et al. |
| 2008/0194918 A1 | 8/2008 | Kulik et al. |
| 2008/0248781 A1 | 10/2008 | Cedo Perpinya |
| 2008/0262360 A1 | 10/2008 | Dalal et al. |
| 2009/0051545 A1 | 2/2009 | Koblasz |
| 2009/0091458 A1 | 4/2009 | Deutsch |
| 2009/0119330 A1 | 5/2009 | Sampath et al. |
| 2009/0160541 A1 | 6/2009 | Liu et al. |
| 2009/0184823 A1 | 7/2009 | Tessier |
| 2009/0224907 A1 | 9/2009 | Sinha et al. |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0234718 A1 | 9/2010 | Sampath et al. |
| 2010/0235782 A1 | 9/2010 | Powell et al. |
| 2010/0261979 A1 | 10/2010 | Kiani |
| 2010/0274100 A1 | 10/2010 | Behar et al. |
| 2010/0286488 A1 | 11/2010 | Cohen |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0296178 A1 | 11/2012 | Lamego et al. |
| 2012/0302894 A1 | 11/2012 | Diab et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |

(56) References Cited

U.S. PATENT DOCUMENTS

| | | |
|---|---|---|
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Kiani |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0120142 A1 | 5/2013 | Wildman et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0029664 A1 | 1/2014 | Au et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0244790 A1 | 8/2014 | Ise et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2015/0380875 A1 | 12/2015 | Coverston et al. |
| 2016/0029932 A1 | 2/2016 | Al-Ali |
| 2016/0051205 A1 | 2/2016 | Al-Ali et al. |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |

(56) References Cited

U.S. PATENT DOCUMENTS

| | | |
|---|---|---|
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0199871 A1 | 7/2018 | Pauley et al. |
| 2018/0214090 A1 | 8/2018 | Al-Ali et al. |
| 2018/0218792 A1 | 8/2018 | Muhsin et al. |

FOREIGN PATENT DOCUMENTS

| | | |
|---|---|---|
| EP | 1576925 A | 9/2005 |
| JP | 05-053605 | 3/1993 |
| JP | 2001-299707 A | 10/2001 |
| JP | 2004-102863 | 4/2004 |
| JP | 2005-514078 A | 5/2005 |
| JP | 2005-182698 | 7/2005 |
| JP | 2005-251125 | 9/2005 |
| JP | 2005-528967 | 9/2005 |
| JP | 2007-519437 | 7/2007 |
| JP | 2008-036005 | 2/2008 |
| JP | 2008-541822 | 11/2008 |
| JP | 2008-541976 A | 11/2008 |
| JP | 2009-151473 A | 7/2009 |
| JP | 2015-198941 A | 11/2015 |
| JP | 2017-200587 | 11/2017 |
| WO | WO 98/29790 | 7/1998 |
| WO | WO 99/13766 | 3/1999 |
| WO | WO 00/40143 | 7/2000 |
| WO | WO 2002/067122 A | 8/2002 |
| WO | WO 02/093312 A2 | 11/2002 |
| WO | WO 2007/065015 A2 | 6/2007 |
| WO | WO 2009/049254 A2 | 4/2009 |
| WO | WO 2010/102069 | 9/2010 |

OTHER PUBLICATIONS

Capuano et at. "Remote Telemetry—New Twists for Old Technology." Nursing Management. vol. 26, No. 7. Jul. 1995.

Decision to Refuse European Patent Application issued in European Application No. 08837990.4 dated Apr. 10, 2012. European Application No. 08837990.4 shares the same specification as the present application.

Decision of Rejection dated Nov. 26, 2014 in corresponding Japanese Application No. 2011-553097.

Decision to Grant dated Apr. 14, 2015 in corresponding Japanese Application No. 2011-553097, 3 pgs.

DeVita, Michael A., MD, "Medical Emergency Teams: A Vision of the Future," Critical Connections, Feb. 2005, pp. 12-13.

Emergin "General Overview," http://www.emergin.com/technology/default.html, downloaded and printed from the Internet on Dec. 1, 2006 in 2 pages.

European Office Action for EP application No. 08837990.4 dated Dec. 27, 2010.

Grundy et al. "Telemedicine in Critical Care: An Experiment in Health Care Delivery." Oct. 1977.

Grundy et al. "Telemedicine in Critical Care: Problems in design, implementation and assessment." vol. 10, No. 7. Jul. 1982.

International Preliminary Report on Patentability in corresponding PCT Application No. PCT/US2010/026131 dated Sep. 6, 2011.

International Search Report and Written Opinion dated Dec. 17, 2007 regarding PCT/US2006/046295.

International Search Report and Written Opinion dated Apr. 1, 2009 regarding PCT/US2008/079643.

International Search Report for application No. PCT/US2008/079643 dated Jan. 11, 2010.

Lopez-Casado C. et al., "Network architecture for global biomedical monitoring service", Engineering in Medicine and Biology Society, Sep. 2005, p. 2433-2436, Annual International Conference of the Shanghai, China Sep. 1-4, 2005, Piscataway, NJ, USA.

Kang, Ho Hyun et al., "Wired/Wireless Integrated Medical Information Prototype System Using Web Service," Enterprise Networking and Computing in Healthcare Industry, 2005, Healthcom 2005, Proceedings of 7th International Workshop on Busan, South Korea , Jun. 23-25, 2005, Piscataway, NJ, USA, pp. 41-44. ISBN: 0-7803-8940-9.

(56) References Cited

OTHER PUBLICATIONS

Lubrin E. et al., "An Architecture for Wearable, Wireless, Smart Biosensors: The MoteCare Prototype", Networking, International Conference on Systems and International Conference on Mobile Communications and Learning Technologies, 2006, in 6 pages.

Lubrin E. et al., "Motecare: An Adaptive Smart BAN Health Monitoring System", Proceedings of the 4th lasted International Conference on Biomedical Engineering, Feb. 15, 2006, pp. 60-67.

Oetiker T., "MRTG—The Multi Router Traffic Grapher", Proceedings of the Systems Administration Conference, Dec. 6, 1998, pp. 141-147, Boston, Massachusetts.

Office Action dated Jan. 31, 2014 in corresponding Japanese Application No. 2011-553097, 8 pgs.

Decision of Rejection dated Jan. 10, 2017 in correspondiong Japanese Application No. 2015-099195, 8 pgs.

Office Action dated Dec. 15, 2015 in corresponding European Application No. 10 708 058.2-1952, 8 pgs.

Oxford BioSignals Starts Clinical Tirals in US of BioSign Patient Monitoring Technology. Medical Technology Business Europe (Mar. 3, 2005).

Provision of the Minutes in Accordance with Rule 124(4) EPC in European Application No. 08837990.4 dated Apr. 10, 2012, European Application No. 08837990.4 shares the same specification as the present application.

Riudavets J. et al., "Multi Router Traffic Grapher (MRTG) for Body Area Network (BAN) Surveillance" WSEAS Transactions on Computers, Dec. 1, 2004 pp. 1856-1862, vol. 3, Issue 6.

Search Report dated May 27, 2010 in corresponding PCT Application No. PCT/US2010/026131, 11 pgs.

Summons to Attend Oral Proceedings in European Application No. 08837990.4 dated Dec. 14, 2011, European Application No. 08837990.4 shares the same specification as the present application.

WelchAllyn, "Accessories," http:www.monitoring.welchallyn.com/products/accessories/, downloaded and printed from Internet on Nov. 14, 2006 in 1 page.

WelchAllyn, "Product Overview," http://www.monitoring.welchallyn.com/products/, downloaed and printed from the Internet on Nov. 14, 2006 in 2 pages.

WelchAllyn, "Care Units," http://www.monitoring.welchallyn.com/products/careunits/, downloded and printed from the Internet on Nov. 14, 2006 in 5 pages.

WelchAllyn, "Monitoring Applications," http://www.monitoring.welchallyn.com/products/applications/, downloaded and printed from the Internet on Nov. 14, 2006 in 2 pages.

WelchAllyn, "Transport Monitoring," http://www.monitoring.welchallyn.com/products/applications/transport.asp, downloaded and printed from the Internet on Nov. 14, 2006 in 2 pages.

WelchAllyn, "Portable Bedside Monitoring," http://www.monitoring.welchallyn.com/products/applications/portablebed.asp, downloaded and printed from the Internet on Nov. 14, 2006 in 1 page.

WelchAllyn, "Centralized Monitoring," http://www.monitoring.welchallyn.com/products/applications/centralized.asp, downloaded and printed from the Internet on Nov. 14, 2006 in 2 pages.

WelchAllyn, "Miltary Field & Hospital," http://www.monitoring.welchallyn.com/products/applications/military.asp, downloaded and printed from Internet on Nov. 14, 2006 2 pages.

WelchAllyn, "Wireless/Telemetry Monitoring," http://www.monitoring.welchallyn.com/products/wireless/, downloaded and printed from Internet on Nov. 14, 2006 in 1 page.

WelchAllyn, "FlexNet™," http://www.monitoring.welchallyn.com/products/wireless/flexnet.asp, downloaded and printed from Internet on Nov. 14, 2006 in 1 page.

WelchAllyn, "Micropaq®," http://www.monitoring.welchallyn.com/products/wireless/micropaq.asp, downloaded and printed from Internet on Nov. 14, 2006 in 1 page.

WelchAllyn, "Wireless Propaq® CS," http://www.monitoring.welchallyn.com/products/wireless/wirelesspropaqcs.asp, downloaded and printed from Internet on Nov. 14, 2006 in 2 pages.

WelchAllyn, "Resource Library," http://www.monitoring.welchallyn.com/products/wireless/resourcelib.asp, downloaded and printed from Internet on Nov. 14, 2006 in 3 pages.

WelchAllyn, "Portable Monitors," http://www.monitoring.welchallyn.com/products/portable/, downloaded and printed from Internet on Nov. 14, 2006 in 2 pages.

WelchAllyn, "Propaq® CS," http://www.monitoring.welchallyn.com/products/portable/propaqcs.asp, downloaded and printed from Internet on Nov. 14, 2006 in 2 pages.

WelchAllyn, "Motion Tolerant Propaq® CS," http://www.monitoring.welchallyn.com/products/portable/motiontolerantcs.asp, downloaded and printed from Internet on Nov. 14, 2006 in 2 pages.

WelchAllyn, "Propaq Encore®," http://www.monitoring.welchallyn.com/products/portable/propaqencore.asp, downloaded and printed from Internet on Nov. 14, 2006 in 2 pages.

WelchAllyn, "Motion Tolerant Propaq Encore®," http://www.monitoring.welchallyn.com/products/portable/motiontolerantenc.asp, downloaded and printed from Internet on Nov. 14, 2006 in 2 pages.

WelchAllyn, "Atlas™," http://www.monitoring.welchallyn.com/products/portable/atlas.asp, downloaded and printed from Internet on Nov. 14, 2006 in 1 page.

WelchAllyn, "Vital Signs Monitor 300 Series," http://www.monitoring.welchallyn.com/products/portable/vitalsigns.asp, downloaded and printed from Internet on Nov. 14, 2006 in 2 pages.

WelchAllyn, "Spot Vital Signs®," http://www.monitoring.welchallyn.com/products/portable/spotvitalsigns.asp, downloaded and printed from Internet on Nov. 14, 2006 in 1 page.

WelchAllyn, "Refurbished Monitors," http://www.monitoring.welchallyn.com/products/portable/refurbished.asp, downloaded and printed from Internet on Nov. 14, 2006 in 1 page.

WelchAllyn, "Centralized Monitoring Systems," http://www.monitoring.welchallyn.com/products/systems/, downloaded and printed from Internet on Nov. 14, 2006 in 1 page.

WelchAllyn, "Acuity® Central Station," http://www.monitoring.welchallyn.com/products/systems/acuitycentral.asp, downloaded and printed from Internet on Nov. 14, 2006 in 1 page.

WelchAllyn, "Acuity® LT Central Station," http://www.monitoring.welchallyn.com/products/systems/acuityLTcentral.asp, downloaded and printed from Internet on Nov. 14, 2006 in 1 page.

WelchAllyn, "Mobile Acuity LT™ Central Station," http://www.monitoring.welchallyn.com/products/systems/mobileacuityLTcentral.asp, downloaded and printed from Internet on Nov. 14, 2006 in 1 page.

WelchAllyn, "Flexible Monitoring," http://www.monitoring.welchallyn.com/products/systems/flexible.asp, downloaded and printed from Internet on Nov. 14, 2006 in 2 pages.

WelchAllyn, "Dedicated Network Monitors," http://www.monitoring.welchallyn.com/products/systems/dedicated.asp, downloaded and printed from Internet on Nov. 14, 2006 in 1 page.

WelchAllyn, "Networked Acuity®," http://www.monitoring.welchallyn.com/products/systems/acuitynet.asp, downloaded and printed from Internet on Nov. 14, 2006 in 1 page.

WelchAllyn, "Institution-Wide General Purpose Monitoring," http://www.monitoring.welchallyn.com/products/systems/institution.asp, downloaded and printed from Internet on Nov. 14, 2006 in 1 page.

WelchAllyn, "Process Reegineering," http://www.monitoring.welchallyn.com/products/systems/processreeng.asp, downloaded and printed from Internet on Nov. 14, 2006 in 1 page.

WelchAllyn, "Partners," http://www.monitoring.welchallyn.com/products/partners/, downloaded and printed from Internet on Nov. 14, 2006 in 2 pages.

WelchAllyn, "Welch Allyn OEM Technologies," http://www.monitoring.welchallyn.com/products/oemtech/, downloaded and printed from Internet on Nov. 14, 2006 in 1 page.

Office Action dated Mar. 18, 2016 in corresponding Japanese Application No. 2015-099195, 3 pgs.

Office Action dated May 3, 2016 in corresponding European Application No. 10 708 058.2, 12 pgs.

* cited by examiner

FIG. 9

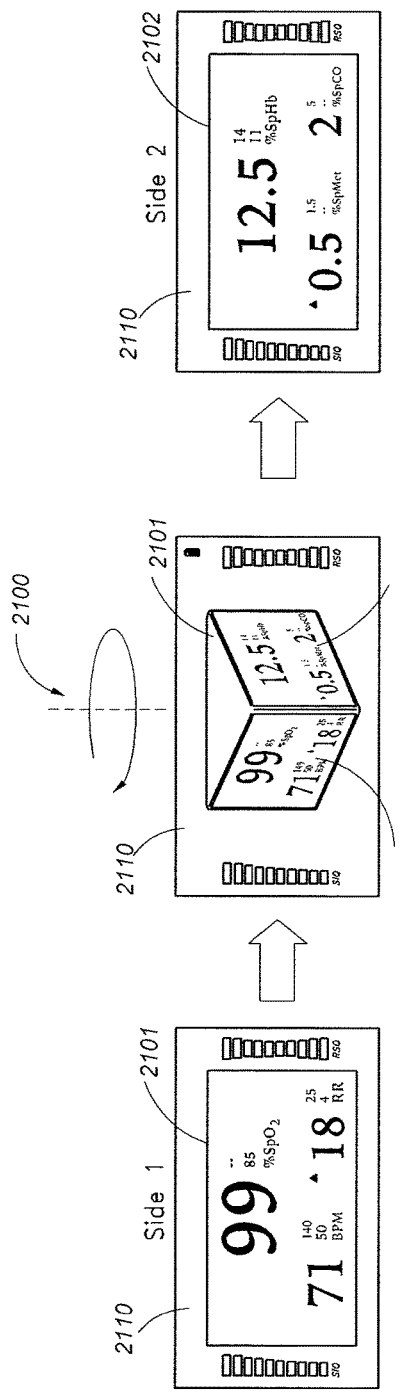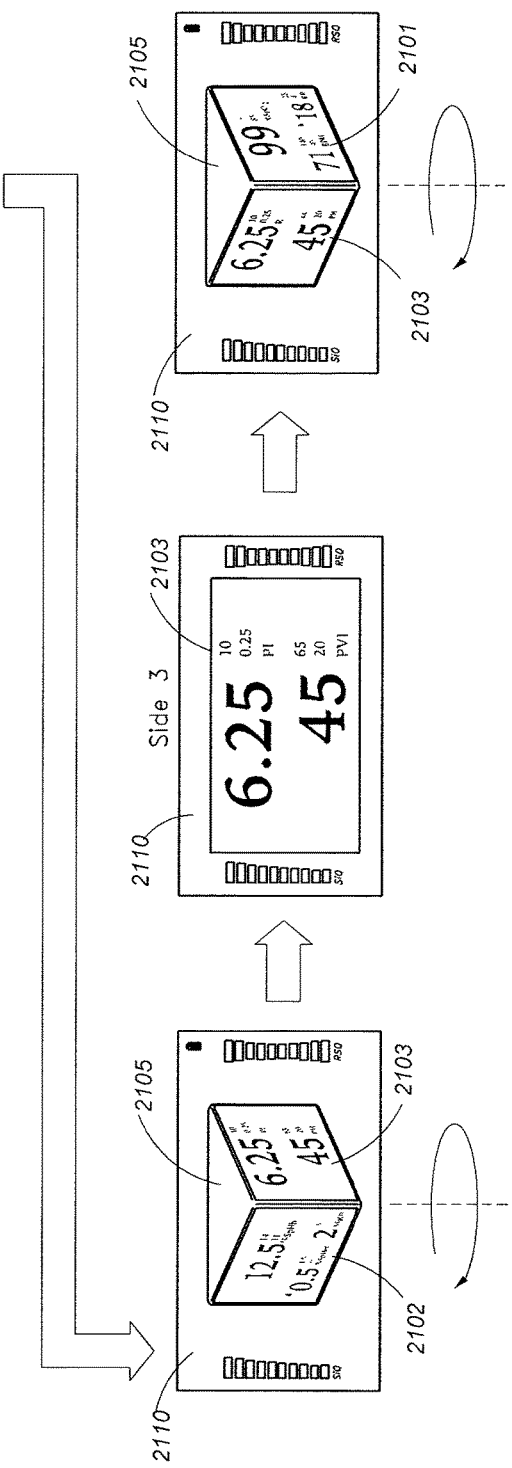

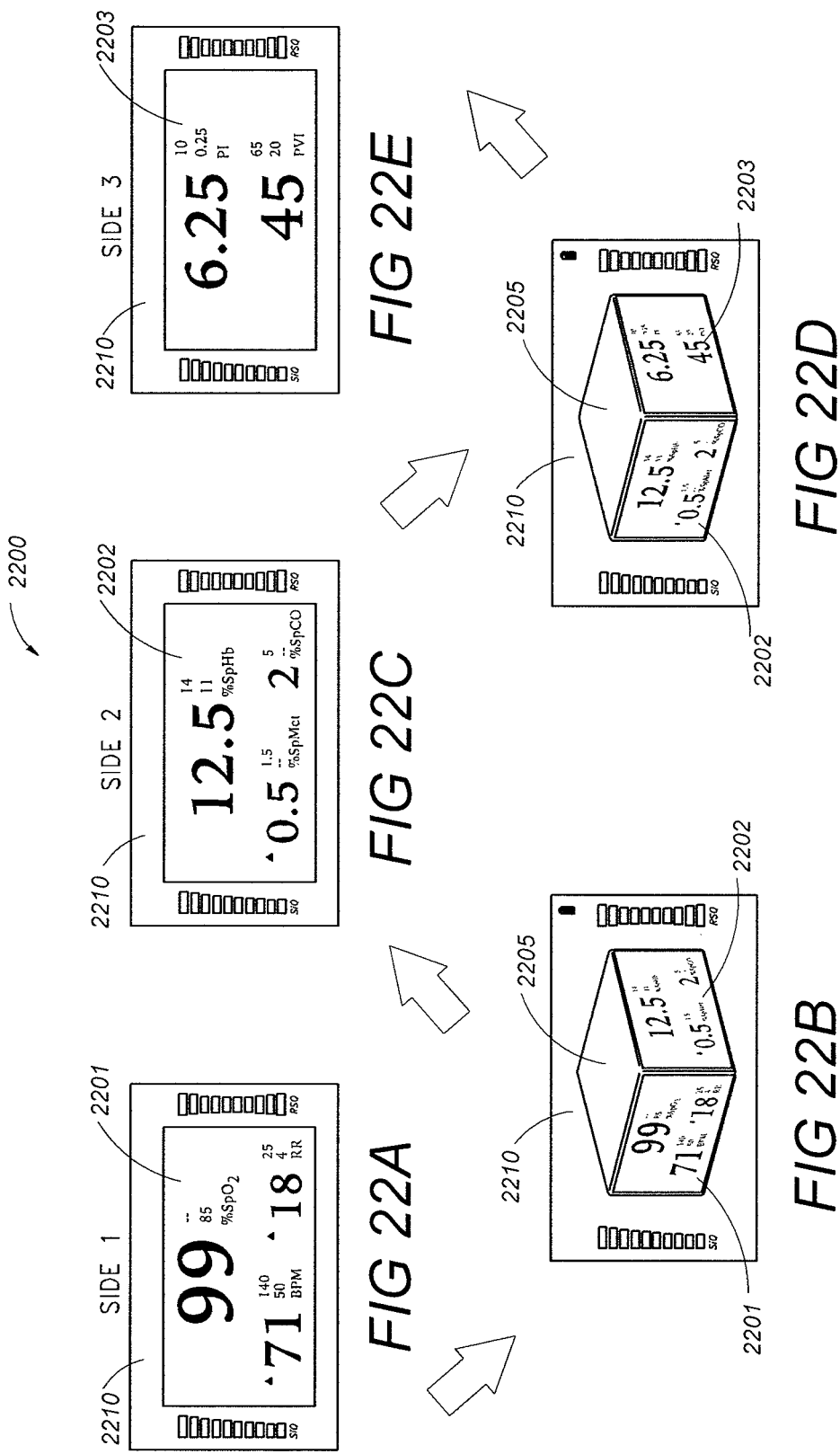

```
<SB>
MSH^~|\&^VAFC_PIMS^50^NPTF-508^200^20091120104609-0600^^^USA<CR>
                                                          2505            2506
EVN^A01^20091120104517-0600^^05<CR>
PID^1^50000000003V30^20090^11~7~M10^""^ALONG~BRIANA^""^19800401^M^^""~0005~""~CDC^""~""~""~""~P~""~""^
  ""~&""~0189~""~~CDC^    <CR>                              &""~""~|~""~~VACAE~""""&""~""""~~VACAM~""""~~VACA0~""""~~VACAC~""~""^
  ^""""""^^""^^"""^^29^^^
PD1^^^SOFTWARE SERVICE~~050^""<CR>
ZPD^1^""^^""^^""^^""^^""^^""^^""^^""^^""^^""^^""^^""^^""^^""^^""^^""^^""^^""^^""^^""^^""^^""^^""^^""^<CR>
PV1^1^I^PSYCH-304~1^^^""^^""^^""^^25~WESSELHOFT~MEAGAN^^^^^^^^NON-VETERAN
  (OTHER)^^^25^^^^^^^^^^^^^^^^^20091120104517-0600^""^^^^^^18<CR>
ROL^18-
  25*1^CO^""""^""~""~T~""""^~VA01^25&50~WESSELHOFT~MEAGAN~""""~""~""~""""~""""~VA200|""""~""~""~""""~""~""~""""~SSA<CR>
ROL^18-
  25*2^CO^""""^""~""~A~""""^~VA01^25&50~WESSELHOFT~MEAGAN~""""~""~""~""""~""~""~""""~VA200|""""~""~""~""""~""~""~""""~SSA<CR>
DG1^1^^^IBS<CR>
ZSP^1^^^""^^^""^^""^^""<CR>
ZEL^1^8^---~^""^^NON-VETERAN (OTHER)^""""^""""^^""^^""^^""^^""^^""^^""^^""<CR>
ZCT^1^1^1^""^^""^^""^^""^^""<CR>
ZEM^1^1^""^^""^^""^^""^^""^^""^^""^^""^^""^^""^^""^^""^^""^^""^^""^^""^^""<CR>
ZIR^1<CR>
ZEN^1<CR>
<EB><CR>
```

FIG. 25A

```xml
<?xml version="1.0" encoding="UTF-8" standalone="no" ?>
<ev7>
   <MSH>
      <MSH.1>^</MSH.1>
      <MSH.2>~|\&</MSH.2>
      <MSH.3>VAFC PIMS</MSH.3>
      <MSH.4>50</MSH.4>
      <MSH.5>NPTF-508</MSH.5>
      <MSH.6>200</MSH.6>
      <MSH.7>20091120104609-0600</MSH.7>
      <MSH.9>
         <component n="1">ADT</component>
         <component n="2">A01</component>
      </MSH.9>
      <MSH.10>58103</MSH.10>
      <MSH.11>P</MSH.11>
      <MSH.17>USA</MSH.17>
   </MSH>
   <EVN>
      <EVN.1>A01</EVN.1>
      <EVN.2>20091120104517-0600</EVN.2>
      <EVN.4>05</EVN.4>
   </EVN>
   ...
<ev7>
```

FIG. 25B

```xml
<?xml version="1.0" encoding="UTF-8"?>
<ADT_A01>
  <MSH>
    <MSH.1>^</MSH.1>
    <MSH.2>~|\&</MSH.2>
    <MSH.3>
      <HD.1>VAFC PIMS</HD.1>
    </MSH.3>
    <MSH.4>
      <HD.1>50</HD.1>
    </MSH.4>
    <MSH.5>
      <HD.1>NPTF-508</HD.1>
    </MSH.5>
    <MSH.6>
      <HD.1>200</HD.1>
    </MSH.6>
    <MSH.7>
      <TS.1>20091120104609-0600</TS.1>
    </MSH.7>
    <MSH.9>
      <MSG.1>ADT</MSG.1>
      <MSG.2>A01</MSG.2>
    </MSH.9>
    <MSH.10>58103</MSH.10>
    <MSH.11>
      <PT.1>P</PT.1>
    </MSH.11>
    <MSH.17>USA</MSH.17>
  </MSH>
  ...
```

FIG. 25C

```
<output-message>                                    2510
  <ACK>
    <MSH>
      <MSH.1>^</MSH.1>
      <MSH.2>~|\&</MSH.2>
      <MSH.3>
         <HD.1>NPTF-508</HD.1>
      </MSH.3>
      <MSH.4>
         <HD.1>200</HD.1>
      </MSH.4>
      <MSH.5>
         <HD.1>VAFC PIMS</HD.1>
      </MSH.5>
      <MSH.6>
         <HD.1>50</HD.1>
      </MSH.6>
      <MSH.7>
         <TS.1>20091120104619.8053-0800</TS.1>
      </MSH.7>
      <MSH.9>
         <MSG.1>ACK</MSG.1>
         <MSG.3>ACK</MSG.3>
      </MSH.9>
      <MSH.10>856bc9bd-97c8-4aa5-b411-3cd6fe2edd86</MSH.10>...
    </MSH>
    <MSA>
      <MSA.1>AA</MSA.1>
      <MSA.2>58103</MSA.2>
    </MSA>
  </ACK>
</output-message>
```

|  | Number of Alarms | Change Versus Actual Alarm Criteria |
|---|---|---|
| Simulated Alarm Criteria #1 | -- | -- |
| Simulated Alarm Criteria #2 | -- | -- |
| Simulated Alarm Criteria #3 | -- | -- |
| Simulated Alarm Criteria #4 | -- | -- |
| Simulated Alarm Criteria #5 | -- | -- |

FIG 32

|  | Number of Alarms | Change Versus Actual Alarm Setting | Estimated False Negatives Detected | Estimated Accurate Alarms Undetected |
|---|---|---|---|---|
| Simulated Alarm Criteria #1 | -- | -- | -- | -- |
| Simulated Alarm Criteria #2 | -- | -- | -- | -- |
| Simulated Alarm Criteria #3 | -- | -- | -- | -- |
| Simulated Alarm Criteria #4 | -- | -- | -- | -- |
| Simulated Alarm Criteria #5 | -- | -- | -- | -- |

FIG 34

8 PARAMETERS
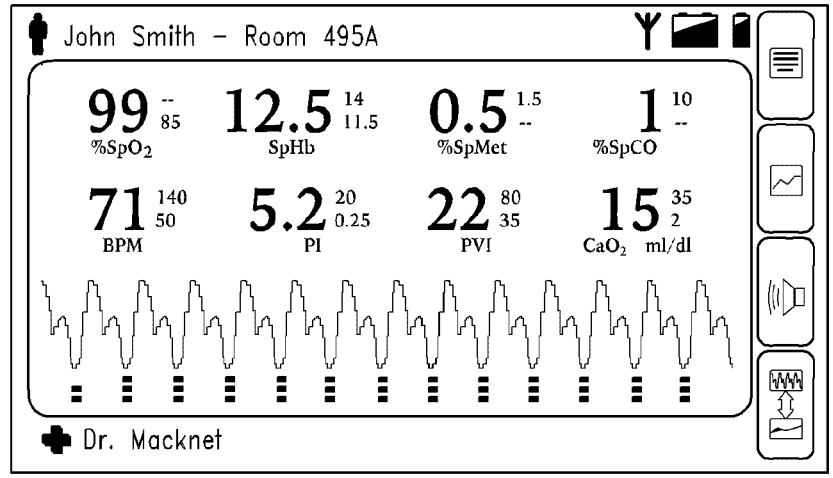
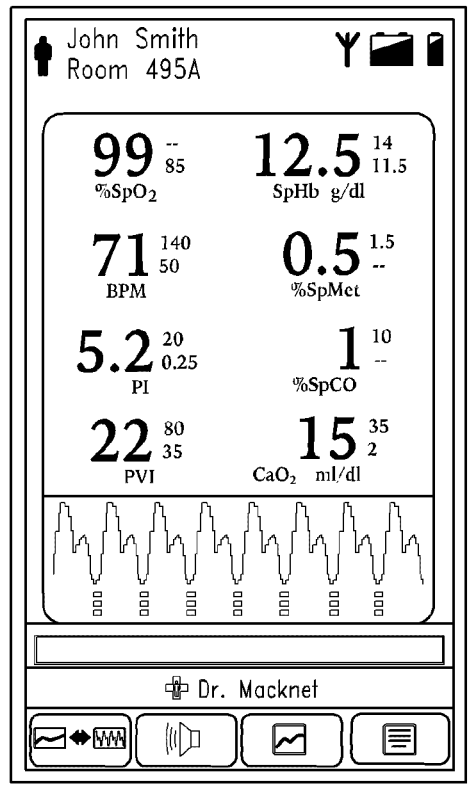
*FIG. 37A*

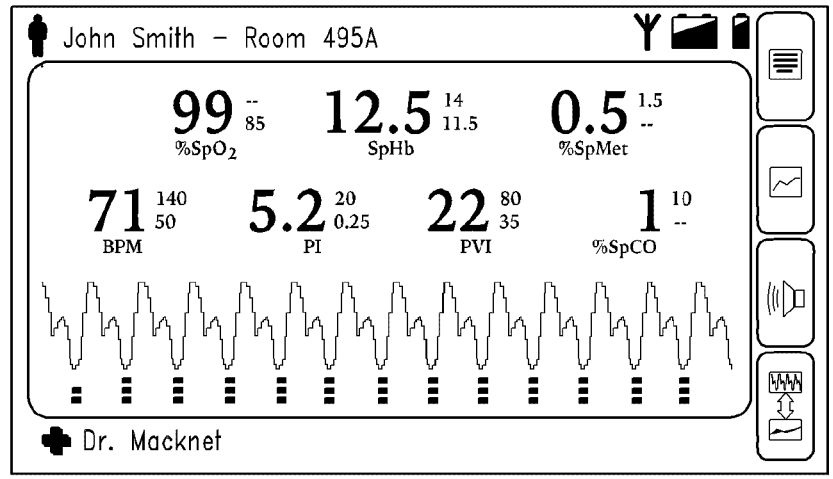
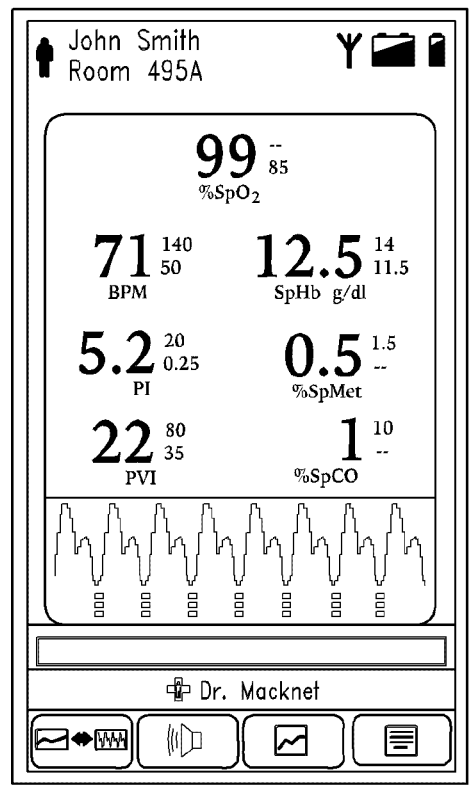
*FIG. 37B*

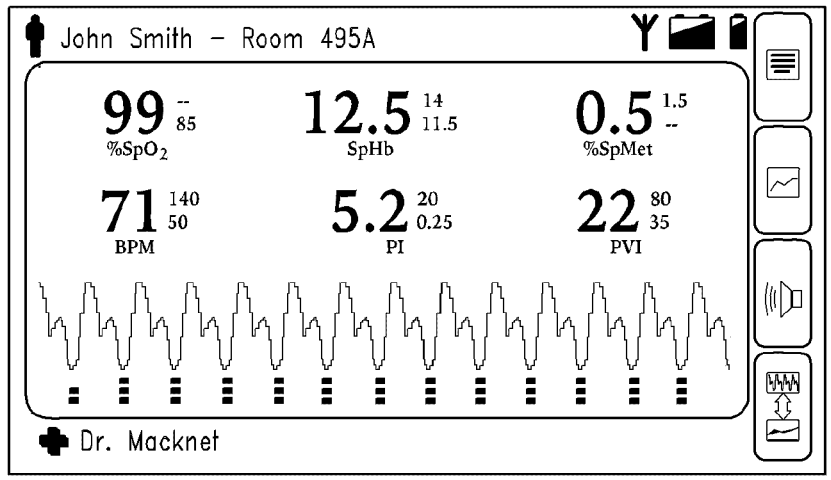
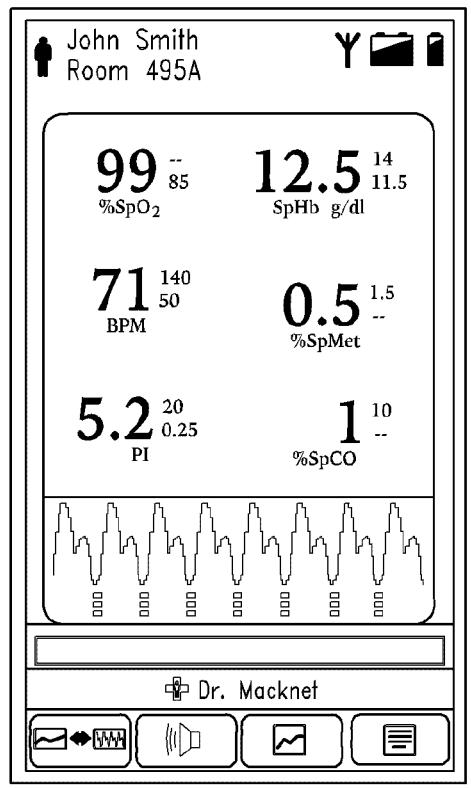
*FIG. 37C*

5 PARAMETERS
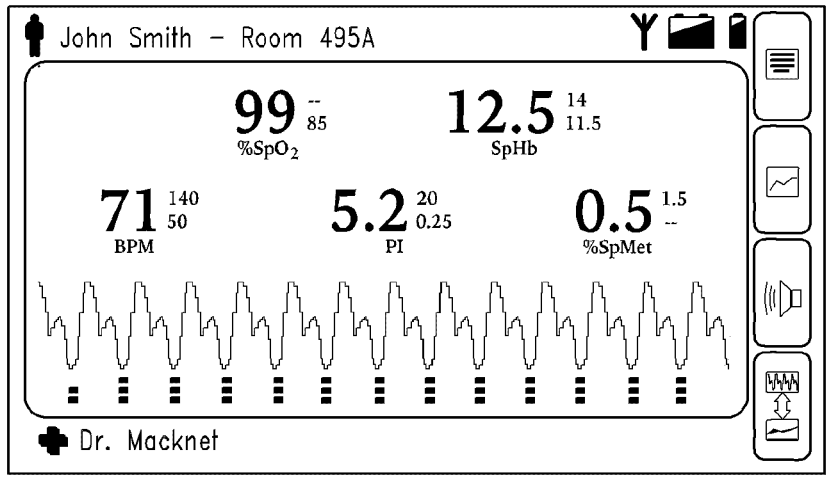
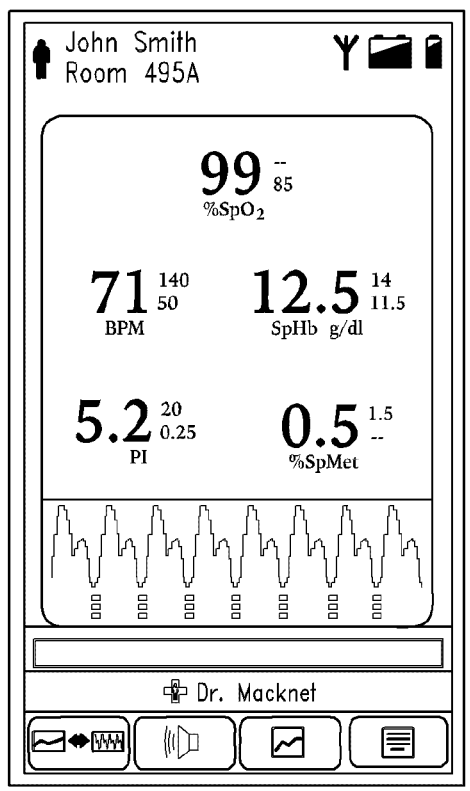
*FIG. 37D*

4 PARAMETERS
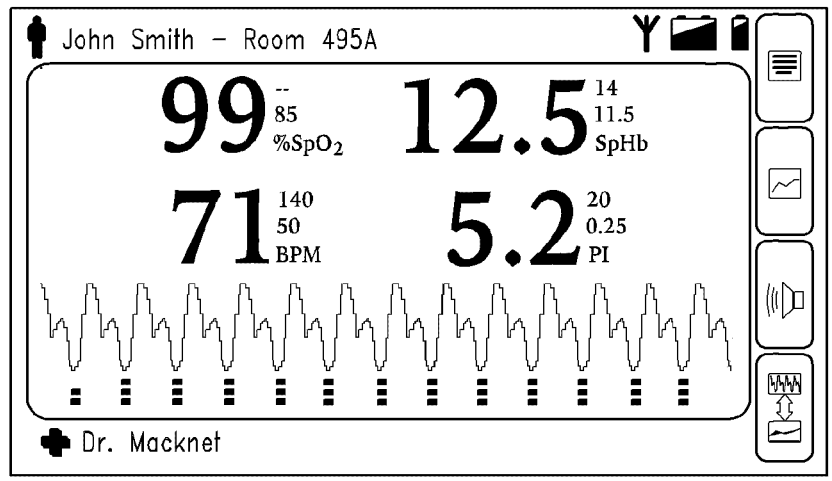
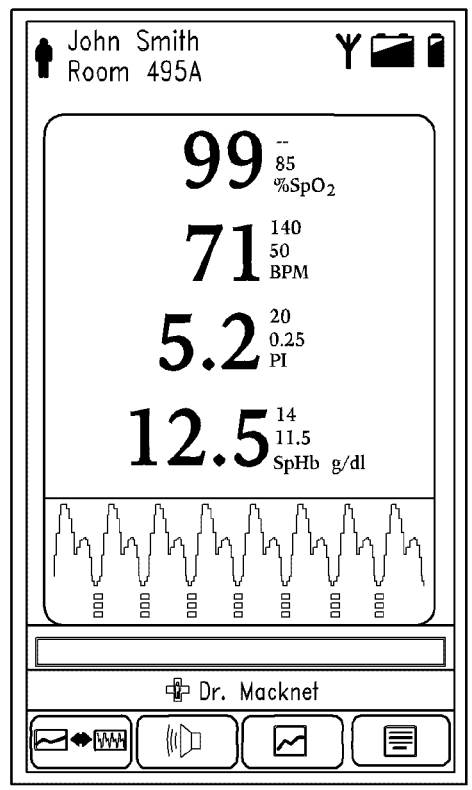
*FIG. 37E*

3 PARAMETERS
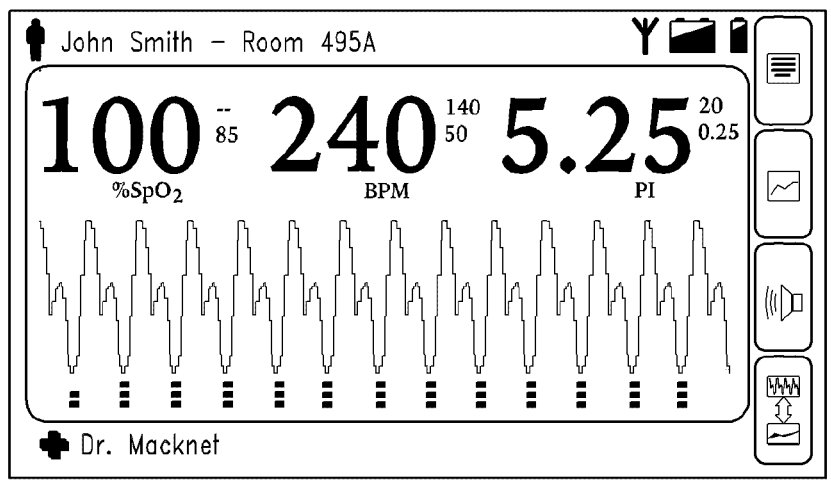
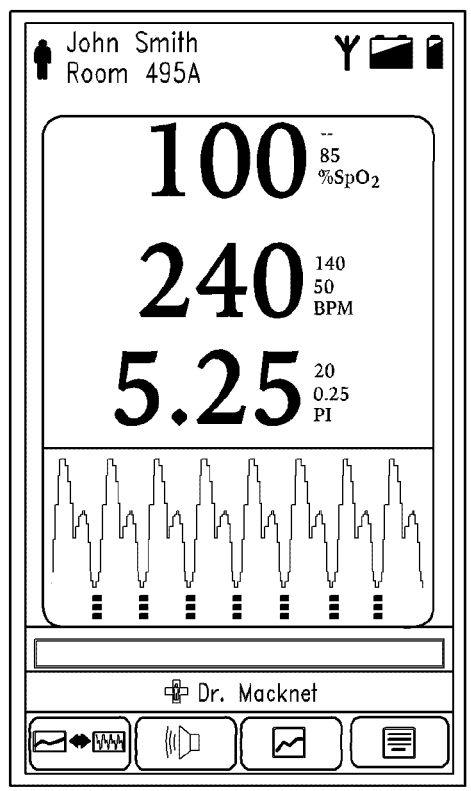
*FIG. 37F*

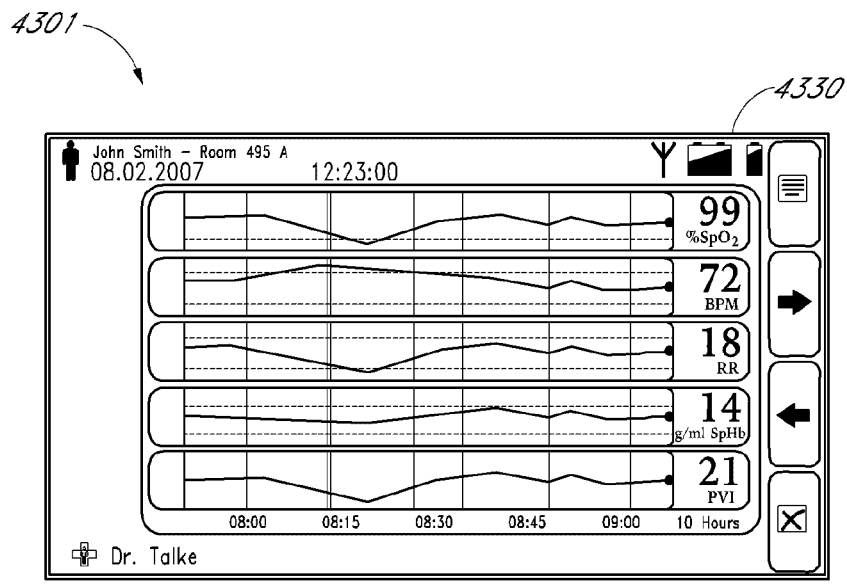
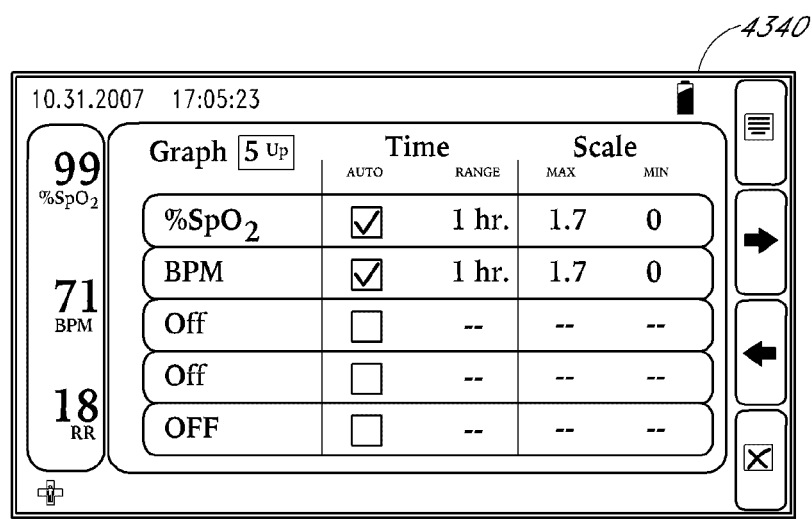
FIG. 43B

PHYSIOLOGICAL ALARM THRESHOLD DETERMINATION

CROSS-REFERENCE TO RELATED APPLICATIONS

This application is a continuation of U.S. patent application Ser. No. 14/975,564, filed Dec. 18, 2015, entitled "MEDICAL COMMUNICATION PROTOCOL TRANSLATOR," which is a divisional of U.S. patent application Ser. No. 12/717,081, now U.S. Pat. No. 9,218,454, filed Mar. 3, 2010, and entitled "MEDICAL MONITORING SYSTEM," which claims a priority benefit to U.S. Provisional Application No. 61/209,147, filed Mar. 4, 2009, and entitled "PROXIMITY DISPLAY MONITOR," and to U.S. Provisional Application No. 61/296,439, filed Jan. 19, 2010, and entitled "MEDICAL MONITORING SYSTEM," the entire contents of each of which are hereby incorporated by reference herein.

BACKGROUND

Field of the Invention

This disclosure relates to systems, devices, and methods with applications in, for example, hospitals and other patient care facilities. For example, the systems, devices, and methods described herein can be used for acquiring physiological information from patients, analyzing the physiological information, and communicating the physiological information to clinicians and other systems or devices.

Description of the Related Art

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, SpO$_2$ level, pulse, and blood pressure, among others. Clinicians, including doctors, nurses, and certain other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as SpO2 and pulse rate in addition to advanced parameters, such as HbCO, HbMet and total hemoglobin (Hbt) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, Calif. (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index, signal quality, HbCO and HbMet among other parameters are also available from Masimo Corporation, Irvine, Calif. (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. Advanced physiological monitors and corresponding multiple wavelength optical sensors capable of measuring parameters in addition to SpO2, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Labs and incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index (PI), signal quality (SiQ), pulse variability index (PVI), HbCO and HbMet among other parameters are also available from Masimo.

SUMMARY OF THE INVENTION

Various medical monitoring devices, systems, and methods are described herein. In some embodiments, a medical monitoring device or system is capable of detecting the presence of a clinician and, for example, taking some action in response to detection of the clinician's presence. In some embodiments, a medical monitoring system is capable of detecting the location of a number of medical devices, clinicians, and/or patients in a hospital or other patient care facility. The detected locations can then be used to take some location-based action, such as, for example, changing the configuration of a medical device.

Various devices, systems and methods for facilitating communication between medical monitoring devices or systems using a medical communication protocol translator are described herein. A medical communication protocol translator can be configured to facilitate communication between medical devices that are programmed to communicate with different protocol formats. The medical communication protocol translator can receive an input message formatted according to a first protocol format from a first medical device and to output an output message formatted according to a second protocol format supported by a second medical device using a set of translation rules. For example, a medical communication protocol translator can receive an input message from a hospital information system formatted according to a first HL7 protocol format and output an output message formatted according to a second HL7 protocol format based on a comparison with the set of translation rules.

In some embodiments, a medical monitoring device or system is capable of collecting physiological parameter data from a number of patients, and using this data to simulate a variety of alarm condition detection criteria and/or alarm notification delay times. These simulated alarm condition detection criteria and/or alarm notification delay times can be analyzed and used to alter actual alarm condition detection criteria and/or alarm notification delay times that are used by, for example, bedside patient monitoring devices.

In certain embodiments, a medical patient monitoring device for monitoring physiological information includes an interface configured to receive physiological information from at least one patient. The device can further include a processor configured to perform a clinically-useful task based on the physiological information. The device can also include a detector for detecting the physical presence of a clinician token within a detection area in the vicinity of the medical patient monitoring device, where the clinician token is indicative of the identity of a clinician. Moreover, the processor can be configured to take a first predetermined action in response to detection of the clinician token, where the first predetermined action is associated with the identity of the clinician.

In certain embodiments, a clinical system for determining the physical locations of a plurality of medical devices includes multiple medical patient monitoring devices that are capable of collecting physiological information from multiple patients. The clinical system can further include a distributed network of detectors that are capable of detecting wireless signals from the medical patient monitoring devices. The clinical system can also include a location monitoring server communicatively coupled to the detectors that is capable of determining estimates of the physical locations of the medical patient monitoring devices based upon the wireless signals detected from the detectors.

In various embodiments, a method for facilitating communication between first and second medical devices within a medical information network includes receiving a first input message from a first medical device, where the first input is generated according to a first communication protocol. The input message can identify a second medical device as an intended recipient of the input message. The method can further include translating the input message into an output message by applying one or more translation rules. The method can also include providing the output message to the second medical device, which is configured to receive and process the output message.

In certain embodiments, a medical device message translator configured to facilitate communication between first and second medical devices within a medical information network includes a communication interface module configured to receive a first input message from a first medical device, the first medical device having generated the input message according to a first communication protocol. The input message can identify a second medical device as an intended recipient of the input message. The translator can further include a rules module configured to store one or more predetermined translation rules and a translation module configured to translate the input message into an output message by applying one or more translation rules retrieved from the rules module. The second medical device can be configured to receive and process the output message.

In various embodiments, a method for converting messages communicated between medical devices and a hospital or clinical information system includes receiving an input message from a hospital information system that includes electronic patient medical records, where the content of the input message is formatted according to a first set of formatting rules allowed under a medical electronic communication protocol. The method can further include comparing the input message to a set of transformation rules and generating an output message, where the content of the output message is re-formatted according to a second set of formatting rules allowed under the medical electronic communication protocol. The transformation rules can control the re-formatting of the content of the output message so as to comply with the second set of formatting rules. The method can also include outputting the output message to a medical device.

In various embodiments, a method of providing field-customizable transformation of input and output medical messages belonging to a common medical electronic communication protocol but having different formats includes receiving an input message from a first medical device, the content of the input message being formatted according to a first set of formatting rules. The method can further include determining an intended recipient medical device from the input message. The method can also include comparing the input message to a set of transformation rules and changing the formatting of the input message to reflect a second set of formatting rules expected by the intended recipient medical device based on the comparison of the input message to the set of transformation rules. Moreover, the method can also include generating an output message, the content of the output message being formatted according to the second set of formatting rules, and outputting the output message to the intended recipient medical device.

In certain embodiments, a system for facilitating communication of medical messages between a hospital information system and a patient monitor includes a hospital information system having an electronic medical records database configured to store electronic medical records of patients. The system can further include a patient monitor configured to monitor at least one physiological condition of a patient. The system can also include a transformation module configured to be communicatively coupled between the hospital information system and the patient monitor. The transformation module can be configured to receive an input message from one of the hospital information system or the patient monitor, the content of the input message being formatted according to a first set of formatting rules; compare the input message to a set of transformation rules; and generate an output message, the content of the output message being re-formatted according to a second set of formatting rules, where the transformation rules control the re-formatting of the content of the output message so as to comply with the second set of formatting rules.

In certain embodiments, a system for facilitating communication of medical messages between medical devices over a network includes a first medical device configured to transmit and receive medical messages, the first medical device configured to be communicatively coupled to a network. The system can further include a second medical device configured to transmit and receive medical messages, the second medical device configured to be communicatively coupled to the network. The system can also include a transformation module configured to be communicatively coupled between the first medical device and the second medical device. The transformation module can be configured to receive an input message from the first medical device, where the content of the input message is formatted according to a first set of formatting rules, and to compare the input message to a set of transformation rules. The transformation module can also be configured to generate an output message, where the content of the output message is re-formatted according to a second set of formatting rules, and where the transformation rules control the re-formatting of the content of the output message so as to comply with the second set of formatting rules. Moreover, the transformation module can be configured to output the output message to the second medical device.

In various embodiments, a method of defining formatting of medical communications under a medical electronic communication protocol includes compiling format transformation software, installing the format transformation software, and updating a set of transformation rules within a user-configurable file without recompiling the format transformation software.

In certain embodiments, a method for analyzing physiological parameter monitoring data includes receiving physiological parameter data from multiple patients. The method can further include receiving first physiological parameter alarm data from the patients that is indicative of alarm conditions experienced by the patients that were detected based upon a first alarm criteria. The method can also include generating second physiological parameter alarm data using a processor, where the second physiological parameter alarm data is indicative of simulated alarm conditions that are detected based upon a second alarm criteria. Moreover, the method can include comparing the first and second physiological parameter alarm data using a processor. In certain embodiments, a computer-readable medium includes instructions that, when read by a computer, cause the computer to perform this method for analyzing physiological parameter monitoring data.

In various embodiments, a method for analyzing physiological parameter monitoring data includes receiving physiological parameter data from multiple patients. The method can further include receiving first physiological parameter alarm notification data indicative of physiological parameter alarm notifications generated based upon a first alarm notification delay time. The method can also include generating second physiological parameter alarm notification data using a processor, where the second physiological parameter alarm notification data is indicative of simulated physiological parameter alarm notifications generated based upon a second alarm notification delay time. Moreover, the method can include comparing the first and second physiological parameter alarm notification data.

BRIEF DESCRIPTION OF THE DRAWINGS

Various embodiments will be described hereinafter with reference to the accompanying drawings. These embodiments are illustrated and described by example only, and are not intended to limit the scope of the disclosure.

FIG. 9 is a screen shot of an example user interface for monitoring patients in the clinical network environment of FIG. 6;

FIGS. 21A-F, FIGS. 22A-E, and FIGS. 23A-C illustrate proximity display embodiments that advantageously provide user proximity feedback;

FIGS. 21A-F illustrate a proximity display embodiment utilizing a virtual rotating triangular solid for proximity feedback;

FIGS. 22A-E illustrate a proximity display embodiment utilizing a virtual rotating cube for proximity feedback;

FIGS. 23A-C illustrate proximity display embodiment utilizing a virtual rotating planar solid for proximity feedback;

FIG. 25A illustrates an example input message received by the translation module;

FIG. 25B illustrates a message header segment of the input message of FIG. 19A that has been parsed into fields;

FIG. 25C illustrates an encoded version of the parsed message header segment of FIG. 25B;

FIG. 25D illustrates an example output message of the translation module based on the input message of FIG. 25A;

FIG. 32 illustrates an example report with a table showing how simulated alarm criteria affect alarm detection events;

FIG. 34 illustrates an example report with a table showing how simulated alarm criteria affect the number of alarm detection events as well as how the simulated alarm criteria affect, for example, false negatives and false positives;

FIGS. 36A-B, FIGS. 37A-F, FIGS. 38A-B, FIGS. 39A-B, FIGS. 40A-B, FIG. 41, FIG. 42, and FIGS. 43A-B illustrate proximity displays that provide advantageous features in multi-user patient-monitoring environment;

FIGS. 36A-B illustrate displays having layout zones;

FIGS. 37A-F illustrate displays that vary layouts and font sizes according to the number of installed parameters;

FIGS. 38A-B illustrate displays having parameter wells;

FIGS. 39A-B illustrate displays that enlarge alarming parameters;

FIGS. 40A-B illustrates displays of trend graphs having colored alarm zones;

FIG. 41 illustrate a display that inverts arrow keys to match the cursor;

FIG. 42 illustrates a display having user-selectable jump-screens; and

FIGS. 43A-B illustrate trend graph displays.

DETAILED DESCRIPTION

In various embodiments, physiological monitoring systems are systems that monitor physiological signals generated by a medical patient and process the signals to determine any of a variety of physiological parameters of the patient. For example, in some cases, a physiological monitoring system can determine any of a variety of physiological parameters of a patient, including respiratory rate, inspiratory time, expiratory time, i:e ratio (e.g., inspiration-to-expiration ratio), inspiratory flow, expiratory flow, tidal volume, minute volume, apnea duration, breath sounds, rales, rhonchi, stridor, and changes in breath sounds such as decreased volume or change in airflow. In addition, in some cases the physiological monitoring system monitors other physiological sounds, such as heart rate to help with probe-off detection, heart sounds (e.g., S1, S2, S3, S4, and murmurs), and changes in heart sounds such as normal to murmur or split heart sounds indicating fluid overload. Moreover, the physiological monitoring system may use a second probe over the chest for better heart sound detection, keep the user inputs to a minimum (for example, only input height), and use a Health Level 7 (HL7) interface to automatically input demography.

A physiological monitoring system of certain embodiments includes one or more patient monitoring devices connected to a shared network using open architecture communications standards. The patient monitoring devices of certain embodiments include a physiological monitor coupled with a network interface module. The physiological monitor includes one or more sensors and a sensor processing module for processing signals from the sensors. The network interface module receives physiological information from the sensor processing module and transmits this information over the shared network. The network interface module may connect to a variety of physiological monitors. In addition, the network interface module of various implementations is a portable bedside device assigned exclusively to one medical patient.

In certain embodiments, the network interface module facilitates establishing a network connection directly with end users over the shared network. These end users, including doctors, nurses, and other hospital staff, may receive physiological information, alarms, and alerts from the network interface module on an electronic device, such as a pager, PDA, laptop, computer, computer on wheels (COW), or the like.

Figure 1:
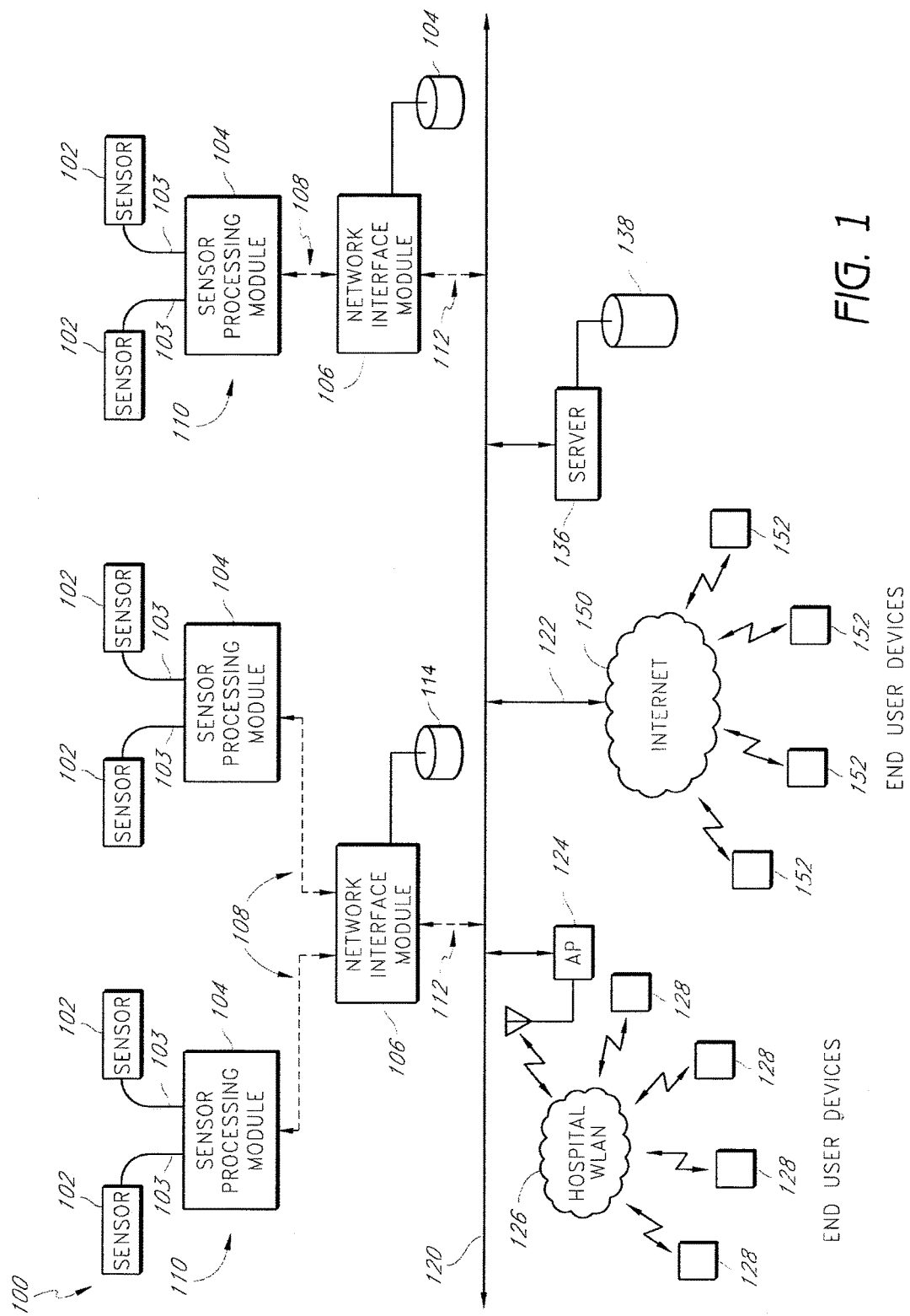
FIG. 1 is an exemplary block diagram showing a physiological monitoring system according to an embodiment of the present invention.

Referring to FIG. 1, certain embodiments of a physiological monitoring system 100 (e.g., alarm notification system) include an open network architecture using "off-the-shelf" hardware and communication protocols. This architecture in various implementations is a shared, or open, network includes multiple patient monitoring devices 110, a network bus 120 (e.g., an Ethernet backbone), and a hospital WLAN 126. In addition, the shared network may further include a connection 122 to the Internet 150, to end user devices 152 over the Internet 150, and to end user devices 128 over the hospital WLAN 126. The physiological monitoring system 100 of certain embodiments is therefore an enterprise system that achieves a cost-effective replacement for currently available patient monitoring systems.

The physiological monitoring system 100 includes a plurality of bedside devices, e.g., patient monitoring devices 110. The patient monitoring devices 110 of various embodiments include sensors 102, one or more sensor processing modules 104, and a communications module, e.g., network interface module 106. In the depicted embodiment, two patient monitoring devices 110 are shown. One patient monitoring device includes one set of sensors 102, one sensor processing module 104, and one network interface module 106. The other patient monitoring device 110 includes two sets of sensors 102, two sensor processing modules 104, and one network interface module 106.

In certain embodiments, each patient monitoring device 110 is used by one medical patient. The patient monitoring devices 110 form a network of patient monitoring devices 110, each of which can communicate with clinicians and other end users over a shared network, including a hospital network 126 and network interfaces to the Internet 150.

One or more sensors 102 of the patient monitoring device 110 are attached to a medical patient. These sensors 102 may include ECG sensors, acoustic sensors, pulse oximeters, and other types of sensors. The sensors 102 obtain physiological information from a medical patient and transmit this information to the sensor processing module 104 through cables 103 or through a wireless connection (not shown). In certain embodiments, the physiological information includes one or more physiological parameters or values and waveforms corresponding to the physiological parameters.

The sensor processing module 104 receives physiological information from the sensors 102. The sensor processing module 104 of certain embodiments includes a circuit having a processor, input ports for receiving the physiological information, software for processing the physiological information in the processor, an optional display, and optionally an input device (e.g., a keyboard). In addition, the sensor processing module 104 contains one or more output ports, such as serial ports. For example, an RS232, RS423, or autobaud RS232 (serial interface standard) port or a universal serial bus (USB) port may be included in the sensor processing module 104.

In certain embodiments, the sensor processing module 104 generates waveforms from signals received from the sensors 102. The sensor processing module 104 may also analyze single or multiparameter trends to provide early warning alerts to clinicians prior to an alarm event. In addition, the sensor processing module 104 in certain embodiments generates alarms in response to physiological parameters exceeding certain safe thresholds.

Example alerts include no communication with pulse oximeter, alarm silenced on pulse oximeter, instrument low battery (pulse oximeter), and transmitter low battery. Example alarms include $SpO_2$ levels and alarms, high and low $SpO_2$, high and low PR, HbCO level and alarms, HbMET level and alarms, pulse rate and alarms, no sensor, sensor off patient, sensor error, low perfusion index, low signal quality, HbCO, HbMET, PI trend alarm, and desat index alarm.

The network interface module 106 in the depicted embodiment is connected to one or more sensor processing modules 104 through one or more connectors 108, which may be serial connectors corresponding to the serial ports in the sensor processing modules 104. Dashed lines on the connector 108 indicate that the network interface module 106 of certain embodiments is not permanently attached to the sensor processing modules 104. In alternative embodiments (not shown), however, the network interface module 106 is contained within a sensor processing module 104.

The network interface module 106 in various implementations includes a processor, an input port (such as a standard RS232 serial port), a network output port such as an Ethernet port, and software which enables the network interface module 106 to act as a network-communications enabled device. In addition, the network interface module 106 includes a storage device 114, which may be included within the network interface module 106 or attached separately to the network interface module 106.

The network interface module 106 manages the connectivity overhead for initiating and maintain connectivity with end user devices over the shared network. In certain embodiments, the network interface module 106 manages connectivity by acting as a microserver or web server. In such instances, the network interface module 106 is a network connection enabled device. As a web server, the network interface module 106 establishes direct connections to the Internet 150, such that an end user may access web pages stored on the storage device 114 of the network interface module 106. In one embodiment, the network interface module 106 therefore does not require a separate server for connecting to the Internet 150. In one embodiment, the network interface module 106 connects to the Internet 150 directly through a modem, such that the connection 122 includes a modem. In managing connectivity over the shared network, the network interface module 106 may also perform security management functions, such as user authentication.

In certain embodiments, the network interface module 106 sends data over the shared network through an access point 124 or other wireless or wired transmitter. Alternatively, the network interface module 106 may communicate physiological information directly to end users over the Internet 150. End users such as clinicians carrying notifier devices, e.g., end user devices 128, 152 connected to the hospital WLAN 126 may receive real-time viewing of physiological patient parameters and waveforms on demand or in the event of an alarm or alert. Real-time or slightly delayed transmission of physiological information in certain embodiments comports with standards for alarm latency in compliance with Joint Commission on Accreditation of Healthcare Organizations (JCAHO) standards for effective alarm response. The network interface module 106 of certain embodiments therefore adds functionality equivalent to a central nurses' station.

In certain embodiments, the network interface module 106 performs context management. In one embodiment, context management includes associating context information with physiological information to form a contextual data package. Context information may include several categories of information, including the categories of context information related to the network interface module 106, context information related to the medical patient, context information related to usage of the network interface module 106, and context information related to a network connection. Within one or more of these context categories, context information might include a patient name, a patients' unique hospital identification number, patient location, an identification number for a network interface module 106, time stamps for events occurring in the physiological monitoring system 100, environmental conditions such as changes to the state of the network and usage statistics of the network interface module 106, and identification information corresponding to the network link (e.g., whether the network connection is WiFi or Ethernet). In one embodiment, the context information in the contextual data package may include all of or any subset of context information from one or more of the context categories.

The network interface module 106 receives context information, for example, by a nurse entering the information in the network interface module 106 or from a server 136. In one embodiment, by receiving this information (including, e.g., patient identification number and location), the network interface module 106 becomes exclusively assigned to the medical patient. The network interface module 106 transmits or communicates the contextual data package to clinicians during an alarm or alert, upon clinician request, or on a scheduled basis. In addition, the network interface module 106 may transmit a continuous stream of physiological information to clinicians.

By optionally connecting to multiple sensor processing modules 104 in certain embodiments, the network interface module 106 is able to associate patient context information and other context information with multiple sensor processing modules 104. Consequently, context can be created for one or more sensor processing modules 104 in addition to context being created for the network interface module 106.

In addition to transmitting the contextual data package, the network interface module 106 in one embodiment stores the contextual data package in the storage device 114. The storage device 114 may be a flash memory, a hard disk drive, or other form of non-volatile or volatile memory. In certain embodiments the storage device 114 acts as a flow control buffer. The network interface module 106 uses the storage device 114 acting as a flow control buffer to perform flow control during communications, as explained more fully below in connection with FIG. 3.

In some implementations, a server 136 may optionally be included in the physiological monitoring system 100. The server 136 in these implementations is generally a computing device such as a blade server or the like. In certain embodiments, the server 136 is an appliance server housed in a data closet. In other embodiments, the server 136 is a server located at a central nurses' station, such as a workstation server.

The server 136 receives contextual data packages from a plurality of network interface modules 106 and stores the contextual data package in a storage device 138. In certain embodiments, this storage device 138 therefore archives long-term patient data. This patient data may be maintained even after the patient is discharged. In storing patient data, the server 136 may act as an interface between the shared network and an external electronic medical record (EMR) system.

The server 136 may also store data concerning user interactions with the system and system performance metrics. Integrated into the server 136 of certain embodiments is a journal database that stores every alert and alarm or a subset of the alerts and alarms as well as human interaction in much the same way as an aviation "black box" records cockpit activity. The journal is not normally accessible to the clinical end user and, without technical authorization, cannot be tampered with. In addition, the server 136 may perform internal journaling of system performance metrics such as overall system uptime.

In one embodiment, the journaling function of the server 136 constitutes a transaction-based architecture. Certain transactions of the physiological monitoring system 100 are journaled such that a timeline of recorded events may later be re-constructed to evaluate the quality of healthcare given. These transactions include state changes relating to physiological information from the patient monitoring devices 100, to the patient monitoring devices 110, to the hospital WLAN 126 connection, to user operation, and to system behavior. Journaling related to the physiological information received from a physiological monitor in one embodiment includes recording the physiological information itself, recording changes in the physiological information, or both.

The server 136 in certain embodiments provides logic and management tools to maintain connectivity between network interface modules 106, clinician notification devices such as PDAs and pagers, and external systems such as EMRs. The server 136 of certain embodiments also provides a web based interface to allow installation (provisioning) of software rated to the physiological monitoring system 100, adding new devices to the system, assigning notifiers (e.g., PDAs, pagers, and the like) to individual clinicians for alarm notification at beginning and end of shift, escalation algorithms in cases where a primary caregiver does not respond to an alarm, interfaces to provide management reporting on the alarm occurrence and response time, location management, and internal journaling of system performance metrics such as overall system uptime (see, e.g., FIG. 5 and accompanying description).

The server 136 in certain embodiments also provides a platform for advanced rules engines and signal processing algorithms that provide early alerts in anticipation of a clinical alarm. The operating system on the server 136 in one embodiment is Linux-based for cost reasons, though a Microsoft-based or other operating system may also be used. Moreover, the server 136 is expandable to include data storage devices and system redundancy capabilities such as RAID (random array of independent disks) and High Availability options.

In another embodiment (not shown), end user devices 128, 152 include one way POCSAG Pagers having a 2 line display with audible and vibrate mode, of suitable size and durability for severe mechanical environments typical of hospital general floor settings. In yet another embodiment, the end user devices 128, 152 include two way paging systems, such as Motorola Flex and WLAN pagers. One advantage of two-way paging is the ability to confirm message receipt and the ability to remotely silence alarms. Wireless PDAs may also be used by end users based on ruggedness and acceptable form factors as determined by an end user. An example of such a device is the Symbol Technology MC50 PDA/Barcode Scanner.

Figure 2:
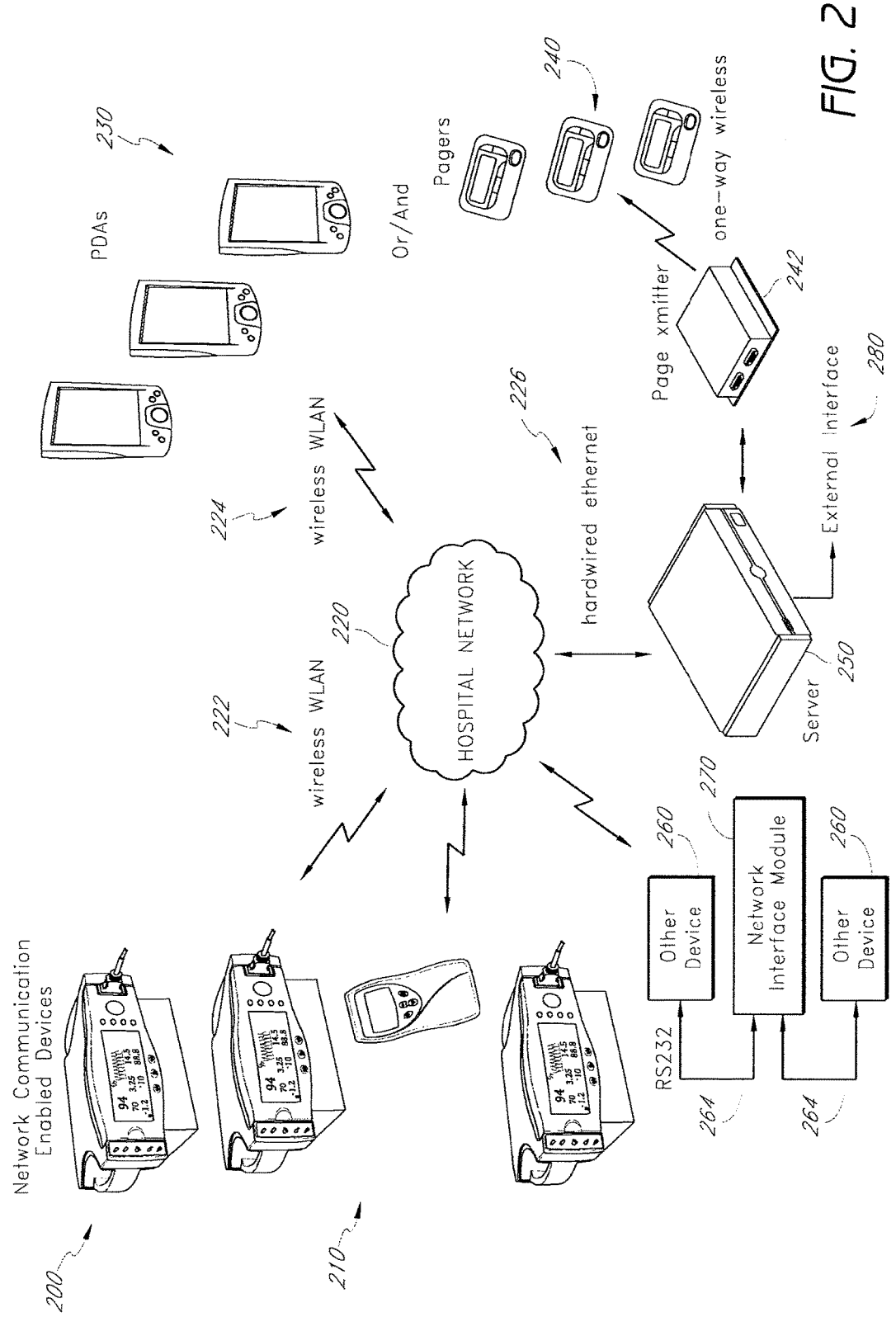
FIG. 2 is an exemplary block diagram showing another embodiment of a physiological monitoring system.

FIG. 2 depicts another embodiment of the physiological monitoring system 200 of the present invention. The physiological monitoring system 200 includes network communications enabled devices 210. The network communications enabled devices 210 are connected directly to a hospital network 220 through a wireless connection. In certain embodiments, the network communications enabled devices 210 include sensors and sensor processing modules, similar to the sensors 102 and sensor processing modules 104 of FIG. 1. Certain of these network communications enabled devices 210 are bedside devices, and others are handheld or otherwise patient-worn devices that may be used by an ambulatory (mobile) patient.

The hospital network 220 transmits physiological information and context information to clinician notifier devices, including pagers 240, PDAs 230, and the like. In certain embodiments, the hospital network 220 utilizes a server 250 to transmit contextual data packages to a page transmitter 242, which further transmits the data to one-way wireless pagers 240. An external interface 280 may be coupled with the server 250. The external interface 280 could include one or more of the following: enterprise paging, nurse call systems, wide area paging systems, enterprise clinical and patient information systems, and third party monitoring and surveillance systems.

Certain other devices 260, such as some patient monitoring equipment, are not network communications enabled devices. That is, these other devices 260 are unable to connect to a network unaided. In the depicted physiological monitoring system 200, example devices 260 that are not network communications enabled are connected to a network interface module 270. The network interface module 270 is connected to the non-network communication enabled other devices 260 through RS232 cables 264. Such a connection is a standardized serial connection found on many devices. Because the network interface module 270 has an RS232 port, the network interface module 270 can allow non-network communication enabled patient monitoring devices to connect directly to the hospital network 220 and also to the Internet.

Moreover, by connecting to one or more other devices 260 in some embodiments, the network interface module 270 is able to associate patient context information and other context information with one or more other devices 260. Consequently, context can be created for one or more other devices 260 in addition to context being created for the network interface module 270.

Figure 3:
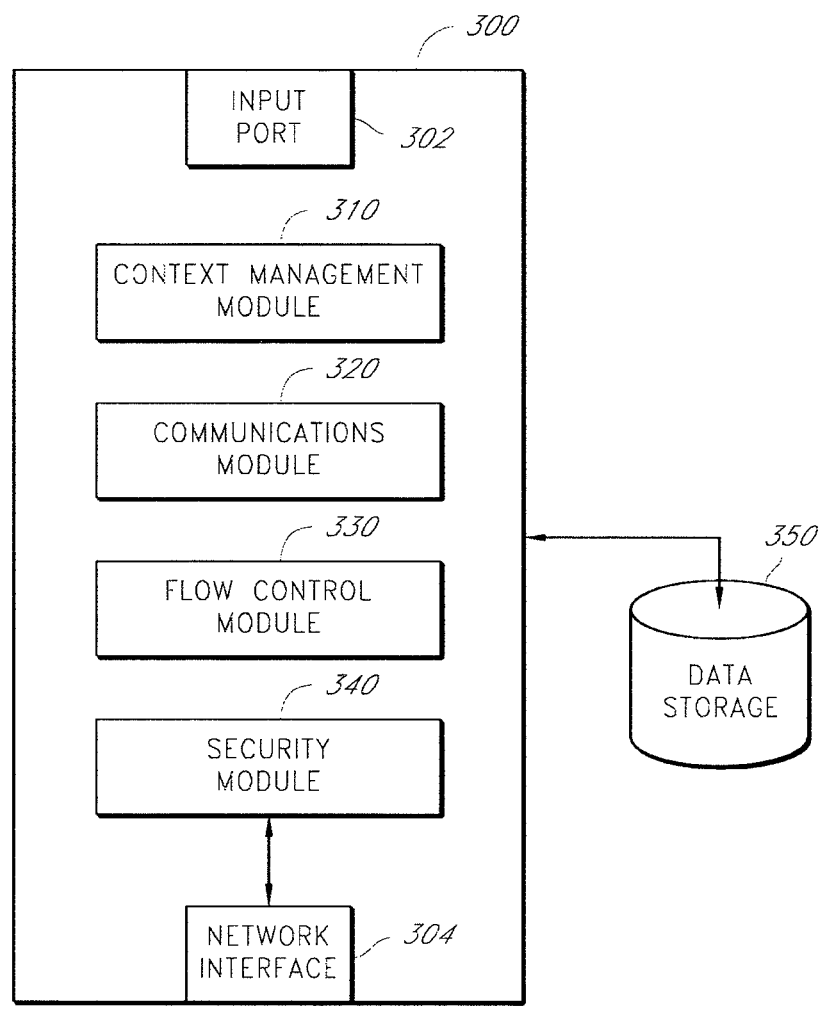
FIG. 3 is an exemplary block diagram showing a network interface module according to an embodiment of the present invention.

FIG. 3 depicts a network interface module 300 in accordance with certain embodiments of the present invention. The network interface module 300 in the depicted embodiment includes an input port 302, which in certain embodiments is a serial port for facilitating a connection to a sensor processing module. The network interface module 300 also includes a network interface 304, which may be a wired interface (e.g., Ethernet) or a wireless interface such as WiFi, Bluetooth, or the like. Alternatively, the network interface module 104 may communicate through a cable TV interface or other type of interface. Such a CTV interface provides a subcarrier bi-directional communications capability that would simultaneously co-exist with video formats.

The network interface module 300 also communicates with a storage device 350. While in the depicted embodiment the storage device 350 is shown as separate from the network interface module 300, in some implementations the storage device 350 is part of the network interface module 300. In addition, though not shown, the network interface module 300 may include a processor for implementing communications program code. Similarly, though not shown, the network interface module 300 may include an input device for a nurse to input context information and a display for receiving output from the network interface module 300.

The network interface module 300 can be integrated into handheld, portable or stationary patient monitoring platforms or instruments or contained in an accessory package with an RS 232 input for general interface to such devices. In another embodiment, (not shown) active RFID tag capabilities are included with the network interface module 106, with the clinician devices (e.g., notifier devices), or with both so that either a patient or a clinician can be located when an event occurs or on request. When operating on a shared network, the network interface module 106 is also compliant with to the open architecture communications standards of IEEE 802.1X (security and authorization), IEEE 802.3 (Ethernet), and WiFi (IEEE 802.11 a, b, g, e, i wireless protocols).

A context management module 310 in the network interface module 300 manages context data. In one embodiment, the context management module 310 receives context information, such as the context information described in connection with FIG. 1 above. In one embodiment, a nurse or other clinician enters context information, such as patient name, identification number, and location, into the network interface module 300 via a keyboard or other input device (not shown) when the patient is admitted to the hospital or assigned a particular bed in the hospital. In other embodiments, the context management module 310 receives the context information from a server, such as the server 136 of FIG. 1.

The context management module 310 associates the context information with physiological information received from a sensor processing module. In certain embodiments, the context management module 310 performs this association when an alarm condition occurs. In such instances, the context management module 310 may create a contextual data package including a snapshot of historical physiological information together with the context information. In other embodiments, the context management module 310 performs an association continuously, and the network interface module 300 sends continuous or scheduled contextual data packages to end users. In addition, the context management module 310 or other modules in the network interface module 300 store the contextual data package in the storage device 350.

The communications module 320 uses the network interface 304 to communicate with a network. In certain embodiments, the communications module 320 possesses the functionality of a web server. As a web server, the communications module 320 enables the network interface module 300 to communicate with a hospital network and the Internet directly, without using a server. Consequently, other devices such as physiological monitoring devices that are not network connection enabled may connect with the network interface module and thereby become network enabled. The network interface module 300 manages the connectivity overhead for initiating and maintaining connectivity, manages context information (e.g., any of the context information described above in connection with FIG. 1), and provides a web server for displaying patient information on web-enabled devices. In one embodiment, a communications protocol based on XML technologies allows bedside devices to interface to a multitude of target end user platforms including PDAs, computer on wheels (COW), Tablet PCs, IP cell phones (smartphones), and fixed PCs.

In certain embodiments, the communications module 320 uses standard communications protocols to communicate with a network. Some examples of standard communications protocols include Ethernet, WiFi (WLAN), Bluetooth, and the like. By using standard communications protocols, the communications module 320 is able to send and receive data over a shared network or open network architecture. However, the communications module 320 may also be used on a proprietary network using proprietary protocols.

In embodiments where the network interface module 300 communicates over a shared network rather than a proprietary network, the network interface module 300 shares network resources with other devices on the network. In some cases, high-volume network traffic affects the reliability of network communications. Consequently, certain implementations of the network interface module 300 include a flow control module 330. The flow control module 330 verifies that transmitted data was received by an end user. In the event that the end user did not receive the data, the flow control module 330 resends the data stored in the storage device 350. In certain embodiments, the storage device 350 therefore acts as a flow control buffer.

A security module 340 manages user access to the network interface device 300 and to data stored in the storage device 350. In certain embodiments, the security module 340 determines whether a user attempting to connect to the network interface module 300 is authorized to do so. In one implementation, the security module 340 uses the standard IEEE.802.1X network access control protocol to manage authentication. The network interface module 106 in certain embodiments provides security and encryption to meet the Health Insurance Portability and Accountability Act (HIPAA) requirements.

In certain embodiments, the network interface module 300 incorporates all or a portion of the functionality specified by the IEEE 1073 standard and the most recent update to the IEEE 1073 standard, namely the IEEE 11703 standard, both of which are hereby incorporated by reference. In certain embodiments, the context management module 310, the communications module 320, the flow control module 330, and the security module 340 also incorporate functionality specified in the IEEE 1073 and 11703 standards. By using standard protocols, the network interface module 300 may be used to enable network communication for a wide variety of physiological monitoring devices.

Figure 4:
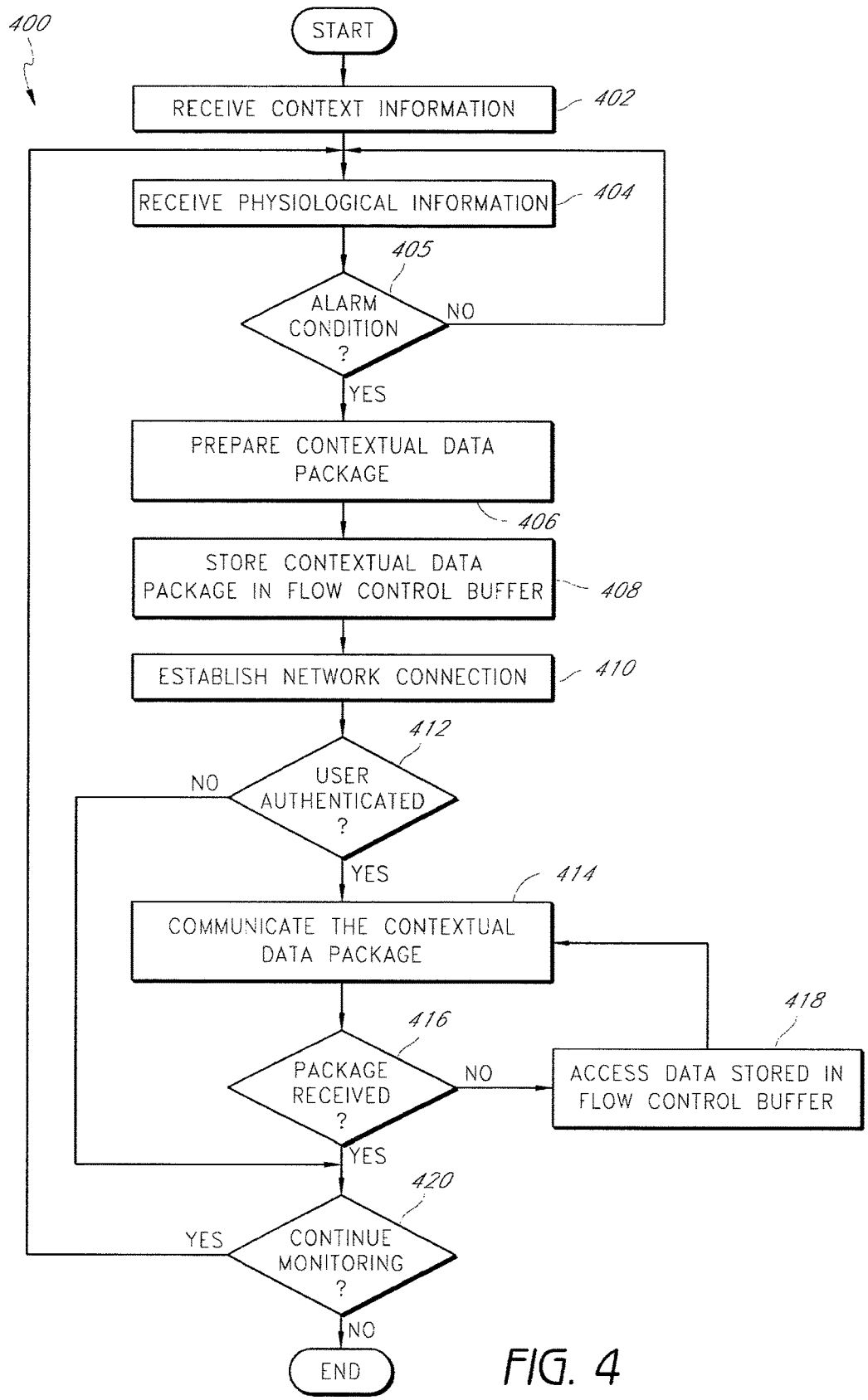
FIG. 4 is an exemplary flowchart diagram showing a process for context-based communication of physiological information according to an embodiment of the present invention.

FIG. 4 depicts a process 400 for context-based communication of physiological information according to an embodiment of the present invention. In certain embodiments, the process 400 is performed by any of the network interface modules described above in connection with FIGS. 1-3. In addition, the process 400 in certain embodiments may be performed by any of the physiological monitoring systems described in connection with FIGS. 1, 2, and 5.

The process 400 begins by receiving context information at 402. In one embodiment, a device such as a network interface module receives the context information once, such as in an initialization step. The process 400 then receives physiological information at 404. In certain embodiments, the process 400 continues to receive physiological information throughout the remaining steps of the process 400. Alternatively, the process 400 may receive physiological information 400 for a portion of the process 400.

At 405, the process 400 determines whether an alarm condition or alert has occurred. If an alarm condition or alert has occurred, the process 400 proceeds to 406. However, if an alarm condition or alert has not occurred, the process 400 loops back to 404. In one embodiment, the looping back of the process 400 to 404 represents that a network interface module continually receives physiological information until an alarm condition or alert occurs. In certain embodiments (not shown), the process 400 may continue to receive physiological information even when an alarm condition or alert occurs.

At 406 the process 400 prepares a contextual data package. The contextual data package may include context information and a snapshot of physiological information. In one embodiment, the snapshot of physiological information includes the physiological information that gave rise to an alarm or alert. In one embodiment, the snapshot of physiological information includes information both before and after the occurrence of an alarm or alert. The contextual data package is stored in a flow control buffer at 408.

At 410, the process 400 establishes a network connection. In one embodiment, establishing a network connection at 410 includes connecting a network interface module to an end user device, such as a notifier device assigned to a nurse during his or her work shift. The process 400 then determines at 412 whether the user of the device (e.g., the nurse) has been authenticated. If the user has not been authenticated, the process 400 proceeds to 420. On the other hand, if the user has been authenticated, the process 400 proceeds to 414.

The process 400 at 414 communicates the contextual data package to the user. At 416, the process 400 determines whether the contextual data package was received. If the contextual data package was received, the process 400 proceeds to 420. Otherwise, the process 400 proceeds to 418, where the process 400 accesses data stored in the flow control buffer. In one embodiment, the data accessed by the process 400 is equivalent to or substantially equivalent to the contextual data package communicated to the user at 414.

The process 400 then loops back to 414, where the process 400 communicates (e.g., resends) the contextual data package to the user, and then at 416 re-verifies that the package was received. The process 400 in some implementations continues to loop between steps 414, 416, and 418 until the contextual data package was received. Thus, steps 414, 416, and 418 in certain embodiments constitute flow control performed by the process 400. These flow control steps allow the process 400 to overcome network transmission errors which may occur in shared networks.

If the contextual data package was received, the process 400 evaluates whether to continue the monitoring of physiological information at 420. If the process 400 determines to continue monitoring, the process loops back to 404, where the process 400 continues to receive physiological information. If, however, the process 400 determines not to continue monitoring, the process 400 ends.

In various embodiments of the process 400, the contextual data package or the physiological information alone is transmitted to the user even in the absence of an alarm condition. In still other embodiments, fewer than all of the steps are performed, or the steps are performed in different order. For instance, the process 400 may only perform the steps of receiving physiological information at 404, preparing a contextual data package at 406, establishing a network connection at 410, and communicating the contextual data package to the user at 414.

Figure 5:
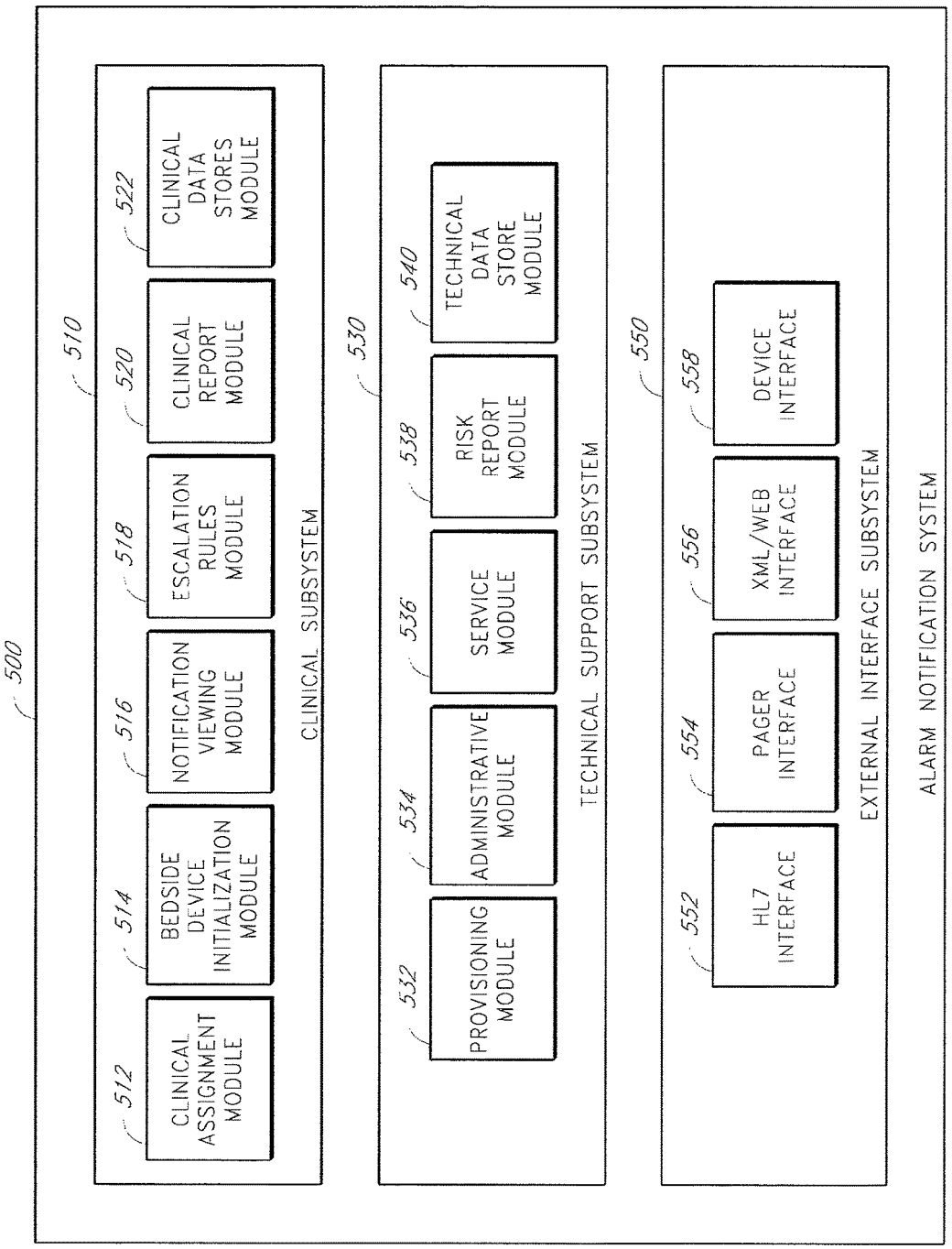
FIG. 5 is an exemplary block diagram showing an alarm notification system according to an embodiment of the present invention.

FIG. 5 depicts an alarm notification system 500 in accordance with certain embodiments of the present invention. A clinical subsystem 510 defines the major software components of alarm notification system 500 including a clinical assignment module 512, a bedside device initialization module 514, a notification and viewing module 516, an escalation rules module 518, a clinical report module 520, and a clinical data stores module 522. An authentication feature is built into mobile computing devices in compliance with HIPAA and hospital IT policies.

The clinical assignment module 512 has an assignment function. A nursing supervisor assigns individual nurses to specific patients at the start of each shift and upon admission of new patients. Shift assignments take place at change of shift during a "report" transition exercise where individual nurses and nursing supervisor from previous shift "hand off" patients to the next shift. The report can be either formal where all nurses attend or informal dependent on hospital nursing service policies and procedures. The clinical assignment module 512 provides an intuitive interface that allows a listing of available nurses to be assigned individual patients. The major user of this module is the unit clerk as assigned by the nursing supervisor. A nurse can be assigned one or more patients or all patients. An alternative work flow is self assignment where individual nurses assign patients themselves in which case they perform functions of the unit clerk. In the self assignment model, a default is implemented where any unassigned patient is either assigned to all nurses or the nursing supervisor.

The bedside device initialization module 514 has bedside devices, such as the network interface modules described above, that are sometimes set up by an aide to the nurse. In the case where the nurse performs this task, she or he performs the functions of the nursing aide. Work flow includes delivering a device to bedside, applying sensors, initializing the device, and setting patient context, such as name, ID and location.

The notification and viewing module 516 assigns a wireless notification device, such as a one-way pager, PDA, IP telephone, COW, or Tablet to individual nurses. The device becomes associated with her or him. Alarms are routed to the notification device based on the clinical assignment module 512. Non-dedicated notifier solutions such as hospital owned paging systems issued to nurses have unknown latency characteristics. A general purpose interface is available at the server with a latency of less than 1 second upon receipt from the bedside device and is time stamped upon presentation to the server external interface and stored in a journaling system within the server. An additional interface for mobile computing platforms such as PDA, COWS, and Tablets allows viewing of current and trend data for an individual patient.

The escalation rules module 518 has a rules engine that actuates an escalation policy defined by the hospital. The escalation rules module 518 provides alternative routing of alarms to alternative and additional clinical users in the event an alarm is not responded to or persists for a predefined (e.g., by a policy) period of time. The escalation rules module 518 in certain embodiments routes alarms to an emergency response team.

The clinical report module 520 provides predefined formatted reports on the clinical data from which to determine physiologic condition and/or progress. More than one report may be dependent on end user needs. Reports are not time critical views of individual patients and may be remotely viewed by clinicians who have alarm notification system 500 privileges and have been authenticated by the alarm notification system 500. These reports are web browser views that allow clinicians to set viewing parameters such as time and parameter scales and alarm review.

The clinical data stores module 522 provides data storage and database resources to store information as known to those skilled in the art.

Further shown in FIG. 5, a technical support subsystem 530 is isolated from the clinical subsystem 510 in compliance with HIPAA and as such does not allow viewing or access to any patient information with the exception of the risk report module 538. The technical support subsystem 530 includes a provisioning module 532, an administration module, a service module 536, a risk report module 538, and a technical data store module 540.

The provisioning module 532 provides provisioning, which is the initial installation of the system and first customer use. The primary user of the provisioning module 532 is the field installer. The provisioning module 532 contains all the start up scripts and system configurations to bring the system from shipping boxes to full alarm notification system 500 functionality. Provisioning includes steps to configure individual devices, notifiers such as pagers, PDA, COW, Tables and IP telephone at the customer site, preferably by wireless means (e.g., Bluetooth).

The administrative module 534 provides a system interface for the application administrator to set up users, set policies for various actor privileges such as a nurses aide being able to set or change alarms, set up allowed device connection identifications, and other general systems administrative duties typical of IT systems.

The service module 536 provides interfaces for various technical support actors including remote service, IT Service, and Biomed Service. Each of these actors may perform each others' functions. Interfaces allow the service actors to access system performance data to access performance, for example, data traffic, device assets connected, software version management, CPU loading, network loading, etc. and execute remote technical service procedures, for example, resetting a printer queue, repartition of disk, uploading software patches, etc. The service module 536 includes a full journaling function that stores every user interaction or a portion of user actions that can be captured by the system, especially changes in default values or alarm settings.

The risk report module 538 provides summary reports on alarm occurrences, duration of alarm, clinical response time to alarms and other statistical data to determine overall effectiveness of clinical response to alarms in compliance with JCAHO, other regulatory bodies, and internal quality assurance committees.

The technical data stores module 540 has the same characteristics as the clinical data stores module 522 except that the technical data stores module 540 is used for technical data. The technical data stores module 540 may or may not share the same physical and logical entity as the clinical data stores module 522.

Additionally shown in FIG. 5, an external interface subsystem 550 provides interfaces to bedside devices and external systems such as electronic medical records, admit discharge, transfer systems, POCSAG pager systems, middleware engines such as Emergin, and Web/XML enabled devices such as wireless PDAs, COWs and Tablet PCs. The external interface subsystem 550 has an HL7 interface 552, a pager interface 554, an XML/Web interface 556, and a device interface 558.

The HL7 interface 552 provides a bi-directional interface to electronic medical records (EMR) and supports both push and pull models. The push model is when a bedside nurse initiates data transfer. The pull model is when an EMR system polls the alarm notification system 500 server. The pager interface 554 provides output to external paging system. Message latency is identified to an end user for any user-owned paging solution. This same output can be used for middleware alarm notification systems such as Emergin. The XML/Web interface 556 provides bi-directional interface with mobile computing platforms such as wireless PDA, COWs, Tables, and Web-enabled IP phones. Mobile computing platforms support Web Browser XML applications. The device interface 558 provides a bi-directional interface to bedside devices as well as to other devices enabled by the communications module or accessory. Application Programmer Interface (API) capability is an option for interfacing to other bedside devices.

The major end users of the alarm notification system 500 system (not shown or described for simplicity) include hospital electronic medical records, admit discharge transfer, pharmacy, clinical information, patient flow tracking and others. Actors, e.g., users of the alarm notification system 500, including clinical actors and technical support actors. The clinical actors include nursing supervisors, unit clerks, nursing aides, nurses, rapid response teams and respiratory therapists.

A nursing supervisor assigns individual nurses to specific patients at the beginning of each shift. Shift can vary according to hospital staffing policies. A unit clerk takes direction from the nursing supervisor, typically inputs assignments into system and monitors overall system. A unit clerk may not be available for all shifts. A nursing aide takes assignments from nurse or nursing supervisor, typically applies bedside device sensor, initializes the bedside device and sets alarms to default values. A nurse has primary responsibility for individual patient care and primary response to alarms. The nurse is assigned by nursing supervisor to more than one patient dependent on her/his skills and patient needs and is not always assigned the same patient. Nursing aides are not found in all hospitals.

A rapid response team responds to clinical emergencies initiated by either a bedside nurse or a nursing supervisor. The team supports more than one care unit and has one or more members depending on shift. Rapid Response Teams may not be implemented in all hospitals. A respiratory therapist has responsibilities for management of respiratory care for more than one patient and usually more than one care unit. Respiratory therapists are not found in some international settings.

Clinical actor performance substitution allows a high capability actor to assume the roles of other actors. Alarm notification system 500 allows mechanisms for such performance. For example, a nursing supervisor may perform functions of a unit clerk nursing aide, a nurse and a rapid response team. A nurse may perform functions of a unit clerk, a nursing aide and a rapid response team. In some international markets a nurse may perform the functions of a respiratory therapist.

The technical support actors include field installers, application administrators, remote services, IT engineers, biomedical engineers and risk managers. A field installer provisions the system for initial installation, installs components, and validates that the installation and configuration meet a purchasing contract. An application administrator sets up and maintains user accounts and systems defaults. A remote service provides remote diagnostics and system maintenance over a remote link, such as dial up and VPN. An IT engineer provides network support services if the system is integrated with the hospital IT network. A biomedical engineer provides bedside and system primary service. A risk manager reviews reports for quality and risk mitigation purposes. Technical support actors may also fill in for other actors. For example, an IT engineer, a biomedical engineer, or a remote service can perform the functions of an application administrator. An IT engineer or a biomedical engineer can perform each other's functions.

In certain embodiments, systems and methods are provided for rapidly storing and acquiring physiological trend data. For instance, physiological information obtained from a medical patient can be stored in a round-robin database. The round-robin database can store the physiological information in a series of records equally spaced in time. Parameter descriptors may be used to identify parameter values in the records. The parameter values can be dynamically updated by changing the parameter descriptors to provide for a flexible database. In addition, the size of files used in the database can be dynamically adjusted to account for patient condition.

Additionally, in certain embodiments, medical data obtained from a clinical network of physiological monitors can be stored or journaled in a journal database. The medical data can include device events that occurred in response to clinician interactions with one or more medical devices. The medical event data may also include device-initiated events, such as alarms and the like. The medical data stored in the journal database can be analyzed to derive statistics or metrics, which may be used to improve clinician and/or hospital performance.

As used herein the terms "round-robin database" and "RRDB," in addition to having their ordinary meaning, can also describe improved database structures having unique characteristics and features disclosed herein. Sometimes these structures are referred to herein as dynamic RRDBs or adaptive RRDBs.

Figure 6:
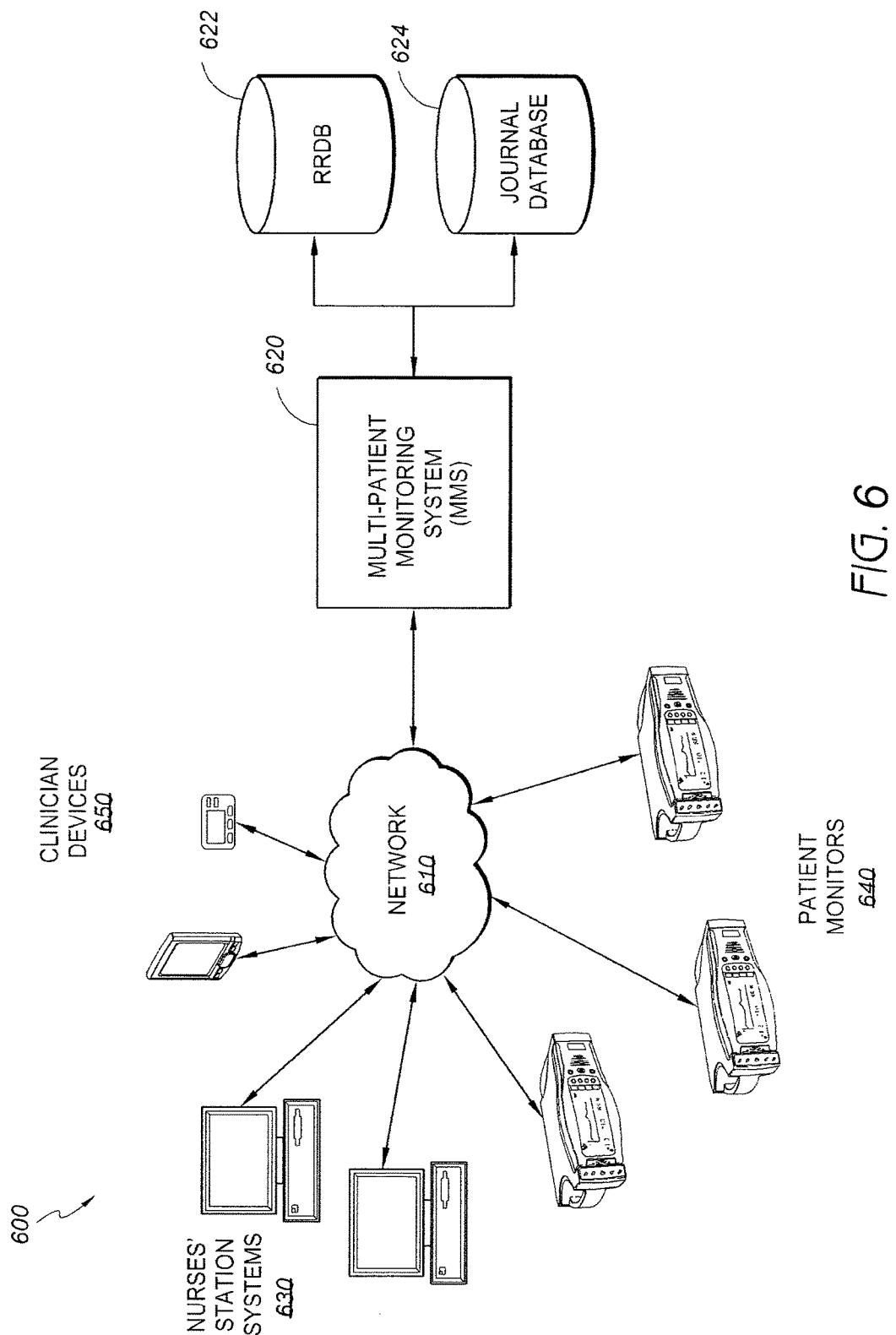
FIG. 6 is a block diagram illustrating an embodiment of a clinical network environment.

FIG. 6 illustrates an embodiment of a clinical network environment 600. The clinical network environment 600 includes a multi-patient monitoring system (MMS) 620 in communication with one or more patient monitors 640, nurses' station systems 630, and clinician devices 650 over a network 610. In certain embodiments, the MMS 620 provides physiological data obtained from the patient monitors 640 to the nurses' station systems 630 and/or the clinician devices 650. Additionally, in certain embodiments, the MMS 620 stores physiological information and medical event information for later analysis.

The network 610 of the clinical network environment 600 can be a LAN or WAN, wireless LAN ("WLAN"), or other type of network used in any hospital, nursing home, patient care center, or other clinical location. For ease of illustration, the remainder of this specification will describe clinical environments in the context of hospitals; however, it should be understood that the features described herein may also be employed in other clinical locations or settings. In some implementations, the network 610 can interconnect devices from multiple hospitals or clinical locations, which may be remote from one another, through the Internet, a leased line, or the like. Likewise, the various devices 620, 630, 640, and 650 of the clinical network environment 100 may be geographically distributed (e.g., among multiple hospitals) or co-located (e.g., in a single hospital).

The patient monitors 640 may be point-of-care (POC) instruments or the like that monitor physiological signals detected by sensors coupled with medical patients. The patient monitors 640 may process the signals to determine any of a variety of physiological parameters. One example of a physiological parameter is blood oxygen saturation ($SpO_2$). Other examples of physiological parameters are described below with respect to FIG. 7.

The patient monitors 640 can provide the physiological information to the MMS 620. The patient monitors 640 can also provide information on medical events, such as alarms, to the MMS 620. Alarms can be triggered, for example, in response to a physiological parameter falling outside of a normal range. Alarms can also include alerts regarding equipment failures, such as a probe-off condition where a sensor has fallen off of a patient. Other examples of medical events are described below with respect to FIG. 7.

In various embodiments, the patient monitors 640 provide the physiological information and medical events to the MMS 620. The MMS 620 is described in greater detail below. In some implementations, the patient monitors 640 may provide at least some of this information directly to the nurses' station systems 630 and clinician devices 650.

The nurses' station systems 630 can be desktop computers, laptops, work stations, or the like that are located at a nurses' station. One or more nurses' station computers 630 can be located at a single nurses' station. The nurses' station computers 630 can receive and display physiological information and alarm data received from the MMS 620 (or monitors 640). In certain embodiments, the nurses' station computers 630 use a graphical user interface (GUI) that provides a streamlined, at-a-glance view of physiological and medical information. An example of this GUI is described below with respect to FIG. 9.

The clinician devices 650 can include any of a variety of devices used by clinicians, such as pagers, cell phones, smart phones, personal digital assistants (PDA), laptops, tablet PCs, personal computers, and the like. The clinician devices 650 are able to receive, in some embodiments, physiological information and alarms from the MMS 620 (or monitors 640). Physiological and alarm data can be provided to a particular clinician device 650, for example, in response to an alarm. The clinician devices 650 can, in some instances, receive values and waveforms of physiological parameters.

The MMS 620 in certain embodiments includes one or more physical computing devices, such as servers, having hardware and/or software for managing network traffic in the network 610. This hardware and/or software may be logically and/or physically divided into different servers 620 for different functions, such as communications servers, web servers, database servers, application servers, file servers, proxy servers, and the like.

The MMS 620 can use standardized protocols (such as TCP/IP) or proprietary protocols to communicate with the patient monitors 640, the nurses' station computers 630, and the clinician devices 650. In one embodiment, when a patient monitor 640 wishes to connect to the MMS 620, the MMS 620 can authenticate the patient monitor 640 and provide the monitor 640 with context information of a patient coupled to the monitor 640. Context information can include patient demography, patient alarm settings, and clinician assignments to the patient, among other things. Examples of context information are described herein. The MMS 620 may obtain this context information from the nurses' station systems 630 or other hospital computer systems, where patient admitting information is provided.

Upon connecting to a patient monitor 640, the MMS 620 may receive physiological information and medical events from the patient monitors 640. The MMS 620 may provide at least a portion of the physiological information and events to the nurses' station systems 630 and/or clinician devices 650. For example, the MMS 620 may provide physiological data and alarms for a plurality of patient monitors 640 to a nurses' station system 630, where nurses can evaluate the data and/or alarms to determine how to treat patients. Similarly, the MMS 620 may send wireless pages, emails, instant messages, or the like to clinician devices 650 to provide clinicians with physiological data and alarms.

Advantageously, in certain embodiments, the MMS 620 can store physiological information obtained from the patient monitors 640 in a round-robin database (RRDB) 624. The RRDB 622 of various embodiments includes a streamlined database structure that facilitates rapidly storing and retrieving patient data. The RRDB 622 can therefore be used in certain embodiments to rapidly provide physiological trend data to the nurses' stations 630 and to the clinician devices 650. Thus, for example, if a clinician desires to see a patient's physiological trends over a certain time period, such as the past hour, the clinician can use a nurses' station computer 630 or clinical device 650 to query the MMS 620. The MMS 620 may then obtain physiological information corresponding to the desired time period from the RRDB 622. Advantageously, the RRDB 622 can enable faster acquisition of trend data then is possible with relational databases currently used by hospital monitoring systems. Additional uses and optimizations of the RRDB 622 are described below.

In certain embodiments, the MMS 620 also archives or stores information about medical events in a journal database 624. The medical events can include events recorded by devices such as the patient monitors 640, nurses' station systems 630, and clinician devices 650. In particular, the medical events can include device events that occur in response to a clinician's interaction with a device, such as a clinician-initiated deactivation of an alarm. The medical events can also include device events that occur without a clinician's interaction with the device, such as the alarm itself. Additional examples of medical events are described below with respect to FIG. 7.

The MMS 620 may analyze the medical event information stored in the journal database 624 to derive statistics about the medical events. For example, the MMS 620 can analyze alarm events and alarm deactivation events to determine clinician response times to alarms. Using these statistics, the MMS 620 may generate reports about clinician and and/or hospital performance. Advantageously, in certain embodiments, these statistics and reports may be used to improve the performance of clinicians and hospitals.

For instance, in certain situations, the reports might help hospitals discover the cause of issues with patient monitors 640. The following example scenario can illustrate potential benefits of such a report. $SpO_2$ alarm levels tend to be different for adults and neonates. However, some clinicians may not know this and may modify neonate $SpO_2$ monitors to include adult alarm levels. These changes can result in many false alarms, which may cause clinicians to become frustrated and avoid using the patient monitors 640. By journaling medical events such as clinician alarm changes, it can be determined by an analysis of the journaled data that clinicians were inappropriately adjusting alarm settings on neonate monitors. A hospital could then use this information to take corrective action, such as by fixing the alarm limits and training the clinicians.

Although not shown, administrative devices may be provided in the clinical network environment 600. The administrative devices can include computing devices operated by hospital administrators, IT staff, or the like. Using the administrative devices, IT staff may, for example, promulgate changes to a plurality of patient monitors 640, nurses' station systems 630, and the MMS 620. The administrative devices may also allow IT staff to interface third-party systems with the MMS 620, such as electronic medical record (EMR) systems. The third party systems may be used, for instance, to change alarm settings on a plurality of monitors from an administrative device. Actions performed by administrators, IT staff, and administrative devices in general may also be journaled in the journal database 624.

Figure 7:
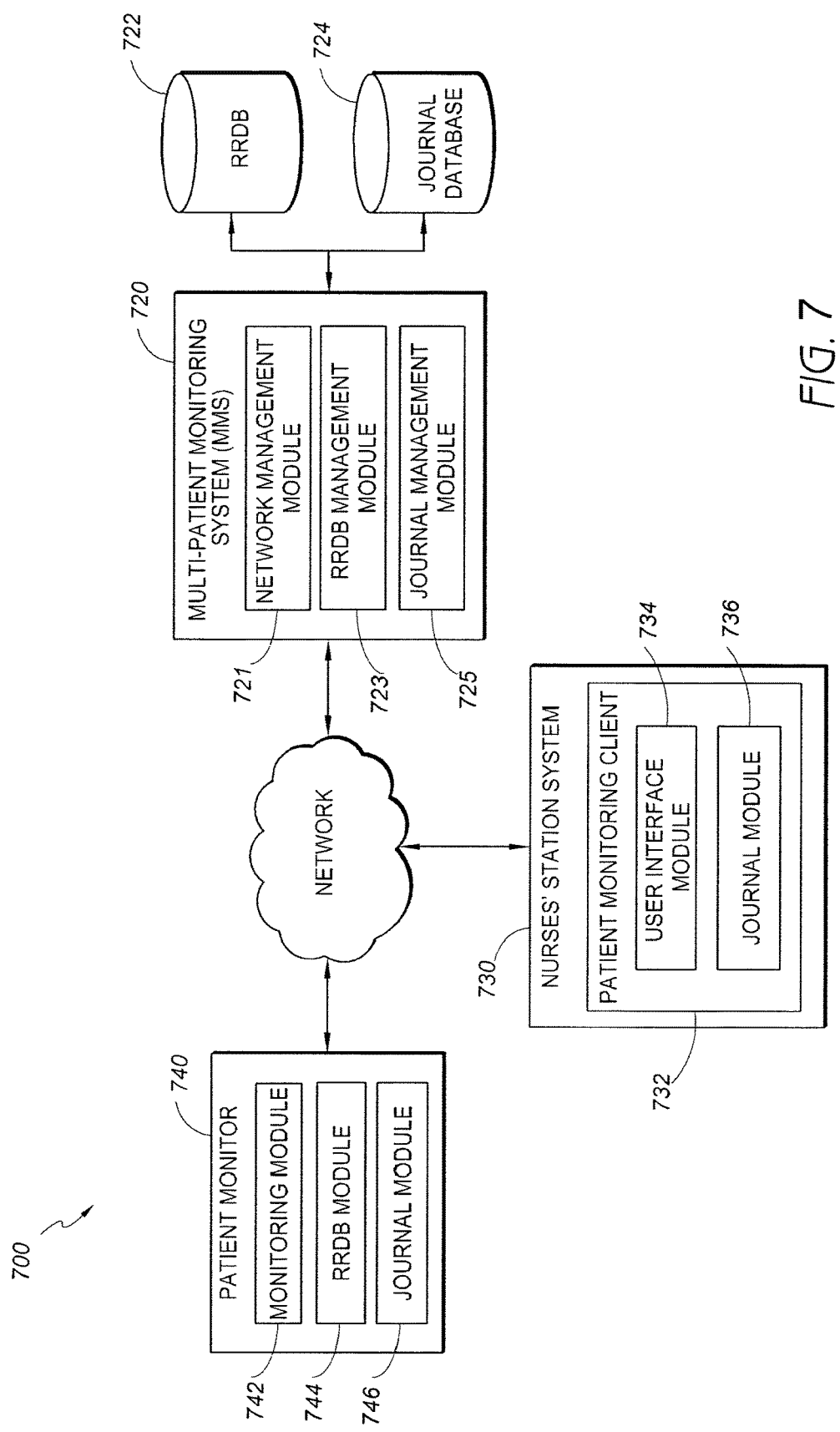
FIG. 7 is a block diagram illustrating a more detailed embodiment of the clinical network environment of FIG. 6.

FIG. 7 illustrates a more detailed embodiment of a clinical network environment 700. The clinical network environment 700 includes a network 710, a patient monitor 740, a nurses' station system 730, an MMS 720, an RRDB 722, and a journal database 724. These components may include all the functionality described above with respect to FIG. 6. One monitor 740 and nurses' station system 730 are shown for ease of illustration. In addition, although not shown, the clinician devices 750 described above may also be included in the clinical network environment 700.

The depicted embodiment of the patient monitor 740 includes a monitoring module 742, an RRDB module 744, and a journal module 746. Each of these modules may include hardware and/or software. Other components, such as a communications module, are not shown but may be included in the patient monitor 740 in various implementations.

The monitoring module 742 can monitor physiological signals generated by one or more sensors coupled with a patient. The monitoring module 742 may process the signals to determine any of a variety of physiological parameters. For example, the monitoring module 742 can determine physiological parameters such as pulse rate, plethysmograph waveform data, perfusion index, and values of blood constituents in body tissue, including for example, arterial carbon monoxide saturation ("HbCO"), methemoglobin saturation ("HbMet"), total hemoglobin ("HbT" or "SpHb"), arterial oxygen saturation ("$SpO_2$"), fractional arterial oxygen saturation ("$SpaO_2$"), oxygen content ("$CaO_2$"), or the like.

In addition, the monitoring module 742 may obtain physiological information from acoustic sensors in order to determine respiratory rate, inspiratory time, expiratory time, inspiration-to-expiration ratio, inspiratory flow, expiratory flow, tidal volume, minute volume, apnea duration, breath sounds, rales, rhonchi, stridor, and changes in breath sounds such as decreased volume or change in airflow. In addition, in some cases the monitoring module 742 monitors other physiological sounds, such as heart rate (e.g., to help with probe-off detection), heart sounds (e.g., S1, S2, S3, S4, and murmurs), and changes in heart sounds such as normal to murmur or split heart sounds indicating fluid overload. Moreover, the monitoring module 742 may monitor a patient's electrical heart activity via electrocardiography (ECG) and numerous other physiological parameters.

In some implementations, the patient monitors 740 may also determine various measures of data confidence, such as the data confidence indicators described in U.S. Pat. No. 7,024,233 entitled "Pulse oximetry data confidence indicator," the disclosure of which is hereby incorporated by reference in its entirety. The patient monitors 740 may also determine a perfusion index, such as the perfusion index described in U.S. Pat. No. 7,292,883 entitled "Physiological assessment system," the disclosure of which is hereby incorporated by reference in its entirety. Moreover, the patient monitors 740 may determine a plethysmograph variability index (PVI), such as the PVI described in U.S. Publication No. 2008/0188760 entitled "Plethysmograph variability processor," the disclosure of which is hereby incorporated by reference in its entirety. The parameters described herein are merely examples, and many other parameters may be used in certain embodiments.

In certain embodiments, the RRDB module 744 receives physiological information from the monitoring module 742 and transmits the physiological information over the network 710 to the MMS 720. In response, the MMS 220 may store the physiological information in the RRDB 722. Advantageously, in certain embodiments, the RRDB module 744 associates the physiological information with parameter descriptors prior to transmittal to the MMS 720. The parameter descriptors may be identifiers that the RRDB module 744 associates with each measured physiological parameter value. The MMS 720 may use these parameter descriptors to identify the types of measured parameters received from the RRDB module 744.

The parameter descriptors may be descriptors generated according to a markup language specification, such as an extensible markup language (XML) specification. As such, the parameter descriptors may include tags that enclose measured physiological values. These tags may be machine readable or human readable. For instance, the tags may include numerical identifiers (e.g., "0017") or descriptive identifiers, such as "SPO2" or "SPHB." A simplified example stream of physiological information from an $SpO_2$ sensor and an SpHb sensor associated with parameter descriptors might be as follows: <SPO2>96</SPO2> <SPHB>14.1</SPHB> <SPO2>97</SPO2> <SPHB>14.0</SPHB>, and so on.

In one embodiment, the RRDB module 744 may have stored (e.g., in a data file) a set of predefined parameter descriptors available for the patient monitor 740. These parameter descriptors may correspond to possible parameters that may be measured by the patient monitor 740. The parameter descriptors transmitted by the RRDB module 744 may depend on the particular subset of parameters measured by the patient monitor 740.

If an additional (or different) parameter is subsequently measured by the patient monitor 740, the RRDB module 740 may dynamically update the parameter descriptors that are sent to the MMS 720. Likewise, if the patient monitor 740 ceases to measure one of the parameters, the RRDB module 744 may cease to transmit the corresponding parameter descriptor to the MMS 720.

The patient monitor 740 also includes a journal module 746 in the depicted embodiment. The journal module 740 may record medical events related to the patient monitor 740. These medical events can include clinician-initiated events, such as changes to alarm settings (e.g., maximum and minimum permitted parameter values), types of parameters monitored/sensors connected to the patient monitor 740, and the like. The journal module 746 may record these events by, for example, acting as a key logger or the like to record button presses of a clinician. The journal module 746 may also include current-sense circuitry to detect when sensors or cables are connected to the monitor 740, and so forth. The medical events may also include non-clinician initiated events, such as alarms and alerts. The medical events can also include events from administrative devices (not shown), such as EMR updates to alarm settings across the network 710.

The journal module 746 may log these events locally at the patient monitor 740. In addition, or instead of logging the events locally, the journal module 746 may transmit information about the events to the MMS 720. In turn, the MMS 720 can store the event information in the journal database 724.

The nurses' station system 730 is shown in the depicted embodiment having a patient monitoring client 732. The patient monitoring client 732 can enable the nurses' station system 730 to receive and display physiological information and alarm information. The patient monitoring client 732 includes a user interface module 734. The user interface module 734 may include, for example, software for displaying physiological information, patient information, and medical event information for a plurality of patient monitors 740. The user interface module 734 may also allow clinicians to admit and discharge patients, remotely modify device alarm limits, and the like. An example user interface that may be generated by the user interface module 734 is described below with respect to FIG. 9.

The patient monitoring client 732 further includes a journal module 736. The journal module 736 may include software for recording medical events related to the patient monitoring client 732. For example, the journal module 736 may record which clinicians login to and logoff of the patient monitoring client 732 and when these events occur; admit and discharge events; and other clinician keystrokes, mouse clicks, and interactions with the patient monitoring client 732. The journal module 736 may log this event information locally at the nurse's station system 730 and/or transmit the event information to the MMS 720.

As shown, the MMS 720 may include a network management module 721, an RRDB management module 723, and a journal management module 725, each of which may include one or more software components. In one embodiment, the network management module 721 receives messages containing physiological information and medical event data from the patient monitor 740. The network management module 721 can provide at least a portion of this data to the nurses' station system 730 and clinician devices 650 of FIG. 6. The network management module 721 can also provide the physiological information to the RRDB management module 723 and provide the medical event data to the journal management module 725.

In certain embodiments, the RRDB management module 723 stores the physiological information received from the patient monitor 740 in the RRDB 722. When the patient monitor 740 initially connects to the MMS 720, or at another time, the RRDB management module 723 can create one or more RRDB files in the RRDB 722 corresponding to the patient monitor 740. The contents of this file or files may depend on the type of patient monitor 740, which may be defined by the patient monitor's 740 serial number, model number, vendor identifier, combinations of the same, or the like. Specific examples of the structure and contents of RRDB files are described in US Patent Publication 2009/0119330, the entire contents of which are hereby incorporated by reference herein.

The RRDB management module 723 can also provide physiological trend data stored in the RRDB to the network management module 721 for transmittal to monitors 740, nurses' station systems 730, and/or clinician devices. The RRDB management module 723 may also provide physiological data from the RRDB 722 to the journal management module 725 for purposes described below with respect to FIG. 8B.

The journal management module 725, in certain implementations, receives medical event data from the monitor 740 and the nurses' station system 730 and stores this data in the journal database 724. In an embodiment, the journal database 724 is a relational database; however, other structures may be used. Each entry of event data may have a corresponding time stamp that indicates when an event occurred. This time stamp may be provided by the journal modules 746 or 736 or by the journal management module 725. The journal management module 725 may also store event counters in the journal database 724 that reflect a number of times medical events occurred. For example, counters could be stored that count how many alarms occurred within a period of time or how many times a clinician logged on or logged off of a network device.

Advantageously, the journal management module 725 may, in certain embodiments, analyze the medical data in the journal database 724 to determine statistics or metrics of clinician and/or hospital performance. The journal management module 725 may provide an interface to users of the nurses' station system 730 or another computing device to access these statistics. In one example embodiment, journal management module 725 can analyze alarm events and alarm deactivation events to determine clinician response times to alarms. The journal management module 725 may further determine the clinician response times in nurses' day and night shifts. The journal management module 725 may generate reports of these statistics so that hospital administrators, for example, may determine which shifts perform better than others.

More generally, the journal management module 725 may generate reports about clinician and and/or hospital performance by analyzing various statistics derived from data in the journal database 724. One example of a report is a monitoring report card, which grades a given hospital against other hospitals (or nurses' station against nurses' station, and the like) based at least partly on the derived statistics. Advantageously, hospital administrators, clinicians, and the like may use these statistics and reports to improve the clinician and hospital performance.

Some or all of the features of the clinical network environment 700 may be adapted in certain embodiments. For instance, either or both of the journal modules 746 or 736 may perform some or all of the functions of the journal management module 725. Likewise, one or more journal databases 724 may be stored at the patient monitor 740 and/or nurses' work station 730. Similarly, the RRDB module 724 may perform some or all of the functions of the RRDB management module 723, and an RRDB 722 may be stored at the patient monitor 740. In addition, in some implementations, the clinician devices 650 of FIG. 6 may have RRDB and/or journal modules as well. Many other adaptations, configurations, and combinations may be made in other embodiments. Additional information regarding embodiments of the RRDM can be found in US Patent Publication 2009/0119330.

Figure 8A:
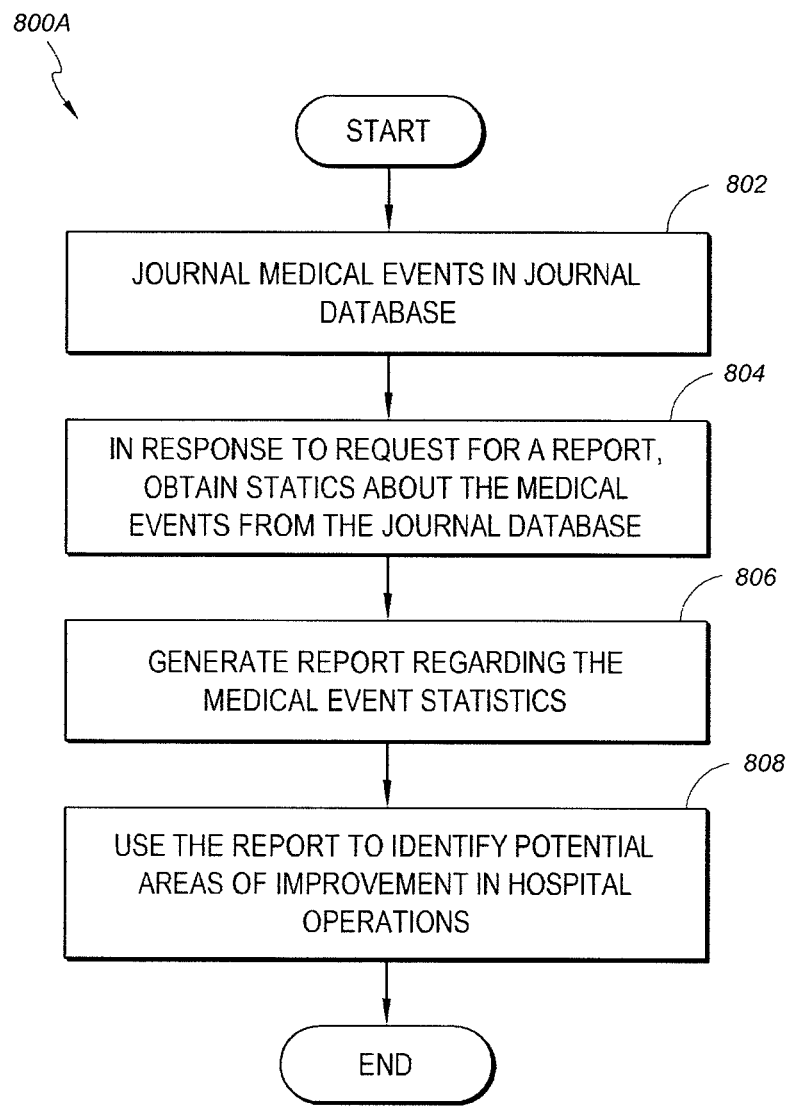
FIG. 8A is a flow chart illustrating an embodiment of a process for journaling medical events in a journal database.

FIG. 8A illustrates an embodiment of a process 800A for journaling medical events in a journal database. In one embodiment, the process 800A may be implemented by any of the MMS's described above (e.g., the MMS 620 or 720). In particular, the process 800A may be implemented by the journal management module 725. Alternatively, at least some of the blocks may be implemented by the journal modules 736, 746. Advantageously, in certain embodiments, the process 800A facilitates the generation of reports based on the journaled data.

At block 802, medical events are journaled in a journal database. In response to requests for report from a user (e.g., a clinician), at block 804 statistics about the medical events are obtained from the journal database. The statistics may include the type, frequency, and duration of medical events, the identity of clinicians or patients associated with the events, alarm response times, combinations of the same, and the like.

A report is generated at block 806 regarding the medical event statistics. At block 808, the report is used to identify potential areas of improvement in hospital operations. For example, the report can be a "monitoring report card" that assigns scores to the hospital or clinicians of the hospital based on their performance.

Figure 8B:
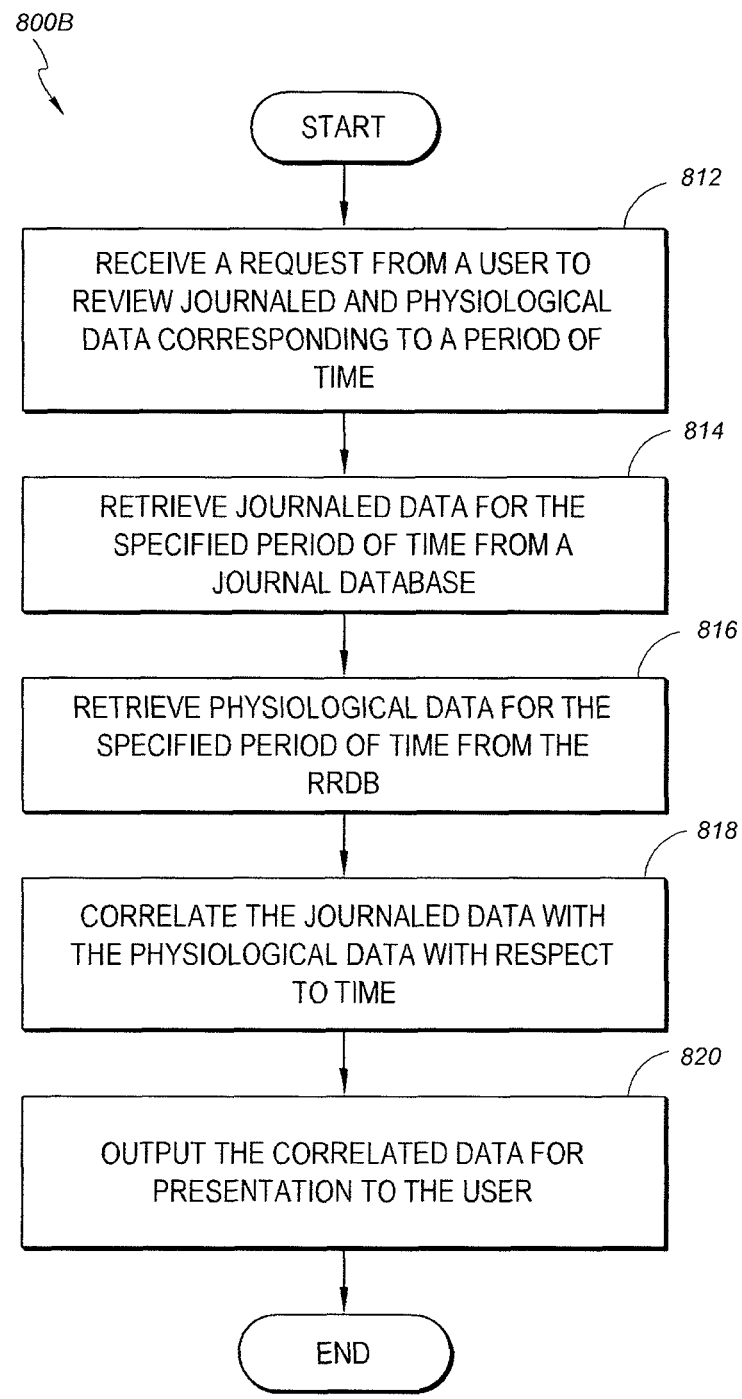
FIG. 8B is a flow chart illustrating an embodiment of a process for correlating data from the journal database and the round-robin database.

FIG. 8B illustrates an embodiment of a process 800B for correlating data from a journal database and an RRDB. In one embodiment, the process 800B may be implemented by any of the MMS's described above (e.g., the MMS 620 or 720). In particular, the process 800B may be implemented by the RRDB module 723 and journal management module 725. Alternatively, at least some of the blocks may be implemented by the RRDB module 744 and journal modules 736, 746. Advantageously, in certain embodiments, the process 800B enables physiological information from the RRDB and medical events to be correlated in time. Such a reconstruction of events and physiological data can be akin to aviation "black box" technology, allowing the user to replay clinical actions leading up to medical incidents.

At block 812, the request is received from a user to review journaled and physiological data corresponding to a period of time. The user may be a clinician, hospital administrator, or the like, who wishes to determine the cause of a problem in the healthcare of a patient. For instance, the user may wish to determine why clinicians failed to respond when a patient's $SpO_2$ dropped below safe levels.

At block 814, journaled data is retrieved for the specified period of time from a journal database. This block may be performed by the journal management module 725. At block 816, physiological data for the specified period of time is retrieved from an RRDB. This block may be performed by the RRDB management module 723. The journal data is correlated with the physiological data with respect to time at block 818. This correlation may include reconstructing a timeline of medical events, with values of physiological parameters (optionally including waveforms) provided in the correct time sequence on the timeline. In some embodiments, to facilitate this coordination between the RRDB management module 723 and the journal management module 725, timestamps in each database 722, 724 may be synchronized when the data is stored.

The correlated data is output for presentation to the user at block 820. The output may include, for example, a graphical view of medical events superimposed on physiological information (e.g., a waveform), or the like. Many display formats may be used for the correlated data.

Figure 9:
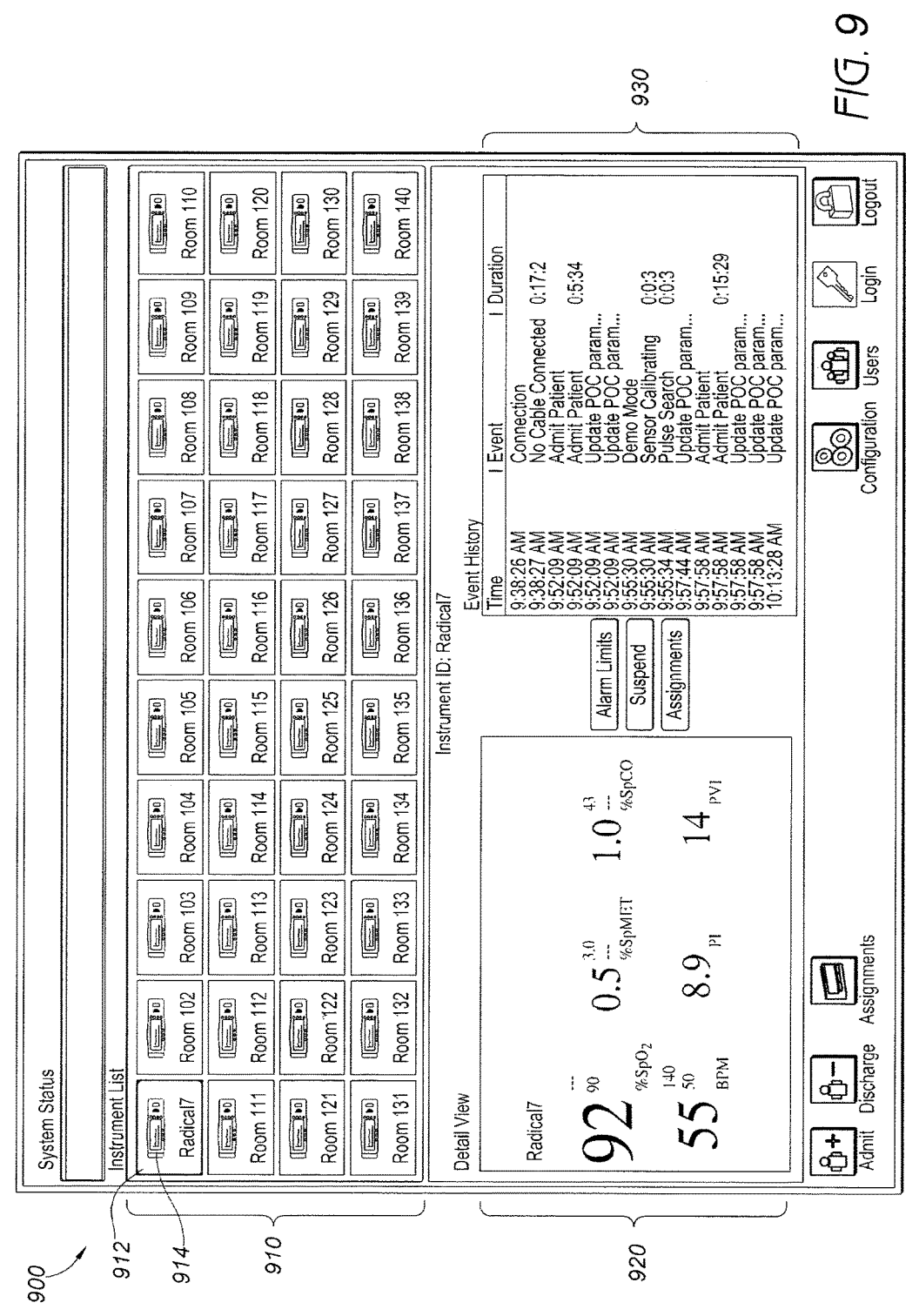

FIG. 9 illustrates an example graphical user interface (GUI) 900 for monitoring patients. The GUI 900 can be provided on a nurses' station system or the like. The GUI 900 can also be displayed on a clinician device.

The GUI 900 includes several display areas. In the depicted embodiment, the GUI 900 includes a patient status display area 910. The patient status display area 910 shows the status of multiple patients in a hospital or other clinical location. In an embodiment, patient status display area 910 depicts patient status for patients in a hospital department. Advantageously, in certain embodiments, the patient status display area 910 provides an "at-a-glance" view of multiple patients' health status.

The patient status display area 910 includes a plurality of patient status modules 912. Each patient status module 912 can correspond to a patient monitor that can be coupled to a medical patient. Each patient status module 912 can display a graphical status indicator 914. An example graphical status indicator 914 is shown in the screens 900 as a miniature patient monitor icon. The graphical status indicator 914 can selectively indicate one of several states of a patient monitor. In one embodiment, four possible patient monitor states can be depicted by the graphical status indicator 914. These include an alarm condition, a no alarm condition, patient context information status, and connection status.

In various implementations, the graphical status indicator 914 changes color, shape, or the like to indicate one of the different patient monitor states. For example, if an alarm condition is present, the graphical status indicator 914 could turn red to signify the alarm. If there is no context information available for the patient (see FIG. 1), then the graphical status indicator 914 could turn yellow. If the device is not connected to the patient or the network, then the graphical status indicator 914 could turn gray. And if there is no alarm condition, if there is context information, and if the patient monitor is connected to the patient and the network, then the graphical status indicator 914 could turn green. Many other colors, symbols, and/or shapes could be used in place of or in combination with the above-described embodiments.

Advantageously, the graphical status indicator 914 shows at a glance the status of a patient monitor. Thus, in the patient status display area 910, several graphical status indicators 914 corresponding to several patients show an at-a-glance view for the patient monitors corresponding to these patients. A clinician can therefore readily see the needs that a patient might have with regards to alarms, connection status, and context information.

Currently available graphical user interfaces for nurses' station computers tend to show a plurality of wave forms or changing physiological parameter numbers for each patient. This method of displaying patient information can be cluttered, confusing, and even hypnotic in some situations. Nurses working on a night shift, for instance, may find it difficult to concentrate on an alarm when several other patients' indicators on the display have changing numbers, changing waveforms, or the like. In contrast, in the graphical interface herein described, when the graphical status indicator 914 indicates an alarm condition, this alarm condition can stand out and be immediately recognized by the clinician.

Moreover, the graphical status indicator 914 simplifies the first level of analysis that nurses tend to perform. In currently available devices, nurses often have to analyze waveforms at the nurses' station to determine the health status of a patient. However, using the screens 900, a nurse need not interpret any waveforms or changing parameters of the patient, but instead can rely on the graphical status indicator 914 that indicates the presence of an alarm.

In certain embodiments, the patient status modules 912 can be selected by a single mouse click or the like. Selecting a patient status module 912 in one embodiment can bring up a patient monitor view area 920. The patient monitor view area 920 shows a view of a patient monitor corresponding to a selected patient status module 912. In certain implementations, the patient monitor view area 920 can show a view of the screen from the actual patient monitor device at the bedside of the patient. Thus, a clinician can readily recognize the physiological parameters of the patient in a format that the clinician is likely familiar with. The patient monitor view area 920 is currently receiving physiological information from a patient.

A history view area 930 in certain implementations can show medical event data corresponding to a selected patient monitor status module 912. This medical event data can be obtained from a journal database for inclusion in the GUI 900. The historical view 930 can show, for example, when a sensor was connected or disconnected from a patient, when alarms were active, and when a patient was admitted to the hospital or department. Although not shown, the history view area 930 can also be configured to show trend data obtained from an RRDB instead of, or in addition to, the journaled data.

Transmission of Patient Information to Remote Devices

In some embodiments, the patient monitoring devices described herein are capable of transmitting patient information to one or more remote devices for review by a clinician. For example, such remote devices can include remote computers, smart phones, PDAs, etc. This is useful because it enhances the ability of a clinician to monitor a patient's condition remotely. For example, the clinician need not be at the patient's bedside or even at a hospital or other patient care facility in order to effectively monitor the patient's condition.

In some embodiments, any of the information collected by a patient monitoring device (e.g., the patient monitoring devices described herein) can be transmitted to a remote device. Such information can include, for example, values, trend data, etc. for a medical parameter (e.g., blood oxygen saturation, pulse rate, respiration rate, etc.). It can also include video of the patient and/or audio from the patient and/or the patient's room. For example, video cameras and/or microphones can be provided in the patient's room. In some embodiments, a video camera and/or microphone is incorporated with, for example, a medical monitoring device, such as those described herein. The video camera can image the patient using visible light when the ambient light in the patient's room is of sufficient intensity. The video camera can also be capable of detecting, for example, infrared light when the patient's room is too dark to provide video of acceptable quality using visible light. The video camera can also include an infrared illumination source to illuminate the patient and/or his or her surroundings. In some embodiments, the video camera includes an ambient light sensor that can be used to automatically switch the video camera into infrared mode when the ambient light falls below some threshold. The light sensor can also be used for switching on an infrared illumination source if one is included.

The transmission of patient information (e.g., medical parameter data, video/audio of the patient, etc.) can be made using, for example, one or more communication networks (e.g., computer networks such as LANs, WLANs, the Internet, etc., telephone networks, etc.). In some embodiments, one or more communication networks that are entirely or partially physically located in a hospital or other patient care center can be used. In some embodiments, external communication networks can be used to reach remote devices throughout the world. Thus, clinicians can remotely obtain a vast amount of information regarding the condition of their patients regardless of the clinician's location. In some embodiments, the clinician may also have the capability to directly communicate with the patient. For example, a patient monitoring device could include a speaker for broadcasting audio from the clinician's remote device to the patient. Similarly, a patient monitoring device could include a display for showing video from the clinician's remote device (e.g., video teleconferencing). In this way, the exchange of information can be bidirectional to allow the clinician to directly interact with the patient.

Hospital Systems with Location Awareness of Devices and Clinicians

Advanced monitoring systems are capable of displaying many different physiological parameters in many different formats. One possible drawback to this substantial performance capability and display flexibility is that excessive information may be presented to the caregivers that use these systems. These caregivers may include physicians, respiratory therapists, registered nurses, and other clinicians whose uses of the monitoring systems may vary from the taking of routine vital signs to the diagnosis and treatment of complex physiological conditions to clinical research and data collection.

Patient monitoring devices, such as those described herein, may include a keyboard, touchscreen, or other input device to allow a clinician to interact with the device. Such user interface devices can be used to allow a clinician to input login information, such as, for example a username and password. In some cases, a monitoring device may require a clinician to login to the device, for example, before permitting access to one or more of the functions offered by the device, and/or before permitting access to certain information available at the device. The nurses' station, or central monitoring station, as described herein, is an example of one such monitoring device that may require a clinician to login in order to use it. Bedside patient monitors may require a clinician to login before initializing monitoring of a new patient. Even where a clinician is not required to login to a patient monitoring device before using it, the device may still require some type of interaction with an input device in order to cause it to take a particular action from amongst a set of available actions offered by the patient monitoring device.

For example, user input may be required in order to configure a patient monitoring device in a desired manner. In some embodiments, a clinician may use an input device to change the content offered on the display of the patient monitor device, or the formatting of the content, to suit his or her preferences. In some instances, a nurse may use the input device to manually configure the central monitoring station to display only monitoring information for those patients that are assigned to that particular nurse rather than displaying, for example, all the patients on the entire floor. A clinician may also use an input device to alter patient monitoring settings such as, for example, options for calculating physiological parameter values from raw data, alarm types, physiological parameter alarm limits (e.g., alarm thresholds), etc.

Given the time demands placed on clinicians in busy hospitals, this process of manually interacting with a patient monitoring device by, for example, physically manipulating an input device can be burdensome, especially when it may need to be repeated over and over throughout the day. In some cases, the time required to manually interact with a patient monitor device in order to access a particular function or configure the device can even jeopardize a patient's well-being in particularly urgent circumstances. For at least the foregoing reasons, it would be advantageous for hospital equipment, such as bedside patient monitors, central monitoring stations, and other devices, to have the capability to automatically detect the presence of a clinician, and to, for example, take some predetermined action based on the identity of the clinician whose presence is detected.

In some embodiments, a proximity display monitor advantageously adapts an advanced monitoring system to various user needs and preferences by adapting the display to the current observer according to, for example, preference, priority, or user acknowledgement. Accordingly, displayed parameters and formats may be chosen by default according to a predefined user class or customized for particular individuals or groups of individuals. One method of identifying persons in the vicinity of a proximity display is by an ID tag or other token. The ID tag may communicate the user to the proximity display monitor via radio-frequency identification (RFID) or wireless radio transmission as examples. If multiple users are in range of a proximity display monitor, a priority scheme or a user acknowledgment may be used to determine which users are accommodated.

In some embodiments, a proximity display monitor has a monitor and an interconnected sensor, the sensor transmits optical radiation into a tissue site and generates a sensor signal responsive to the optical radiation after attenuation by pulsatile blood flow within the tissue site. The monitor may compute physiological parameters responsive to the sensor signal and utilize a proximity display to show the physiological parameters on screen according to a display preference associated with a user in proximity to the monitor. A display can be incorporated with the monitor so as to present the physiological parameters for viewing by a caregiver. A transceiver can be incorporated with the monitor and may be responsive to an identification signal. The identification signal can correspond to a caregiver. A transmitter carried by the caregiver can send the identification signal over a range, for example, approximating the distance from the monitor that a person can reasonably view the display. A preferred screen can present the physiological parameters on the display according to the display preference associated with the caregiver as indicated by the identification signal.

In some embodiments, a proximity display monitor comprises a monitor having a display and a wireless transceiver. The wireless transceiver can be responsive to identification signals which indicate the proximity to the monitor of any users, who have corresponding display preferences. Preferred screens may present the physiological parameters on the display according to the display preferences.

In some embodiments, a proximity display monitor has an optical sensor attached to a fleshy tissue site. A sensor signal may be responsive to optical radiation transmitted by the sensor and detected by the sensor after absorption by pulsatile blood flow within the tissue site. The sensor signal can be communicated to a monitor, which processes the sensor signal so as to derive physiological parameters responsive to constituents of the pulsatile blood flow. The identity of a user in proximity to the monitor can be wirelessly signaled to the monitor. A screen preference, for example, can be determined from the user identity and used to display the physiological parameters on a monitor display.

In some embodiments, a proximity display monitor comprises a processor and a display. The processor can be responsive to a sensor signal generated from optical radiation transmitted into a fleshy tissue site and detected after attenuation by pulsatile blood flow within the tissue site. The processor can be configured to calculate a plurality of physiological parameters indicative of constituents of the pulsatile blood flow. The display may provide a visual representation of the physiological parameters values for viewing by proximate users. A wireless communications means can determine the identities of proximate users. Screen preference means may present the physiological parameters on the display. A lookup table means can relate the user identities to the screen preferences.

Figure 10:
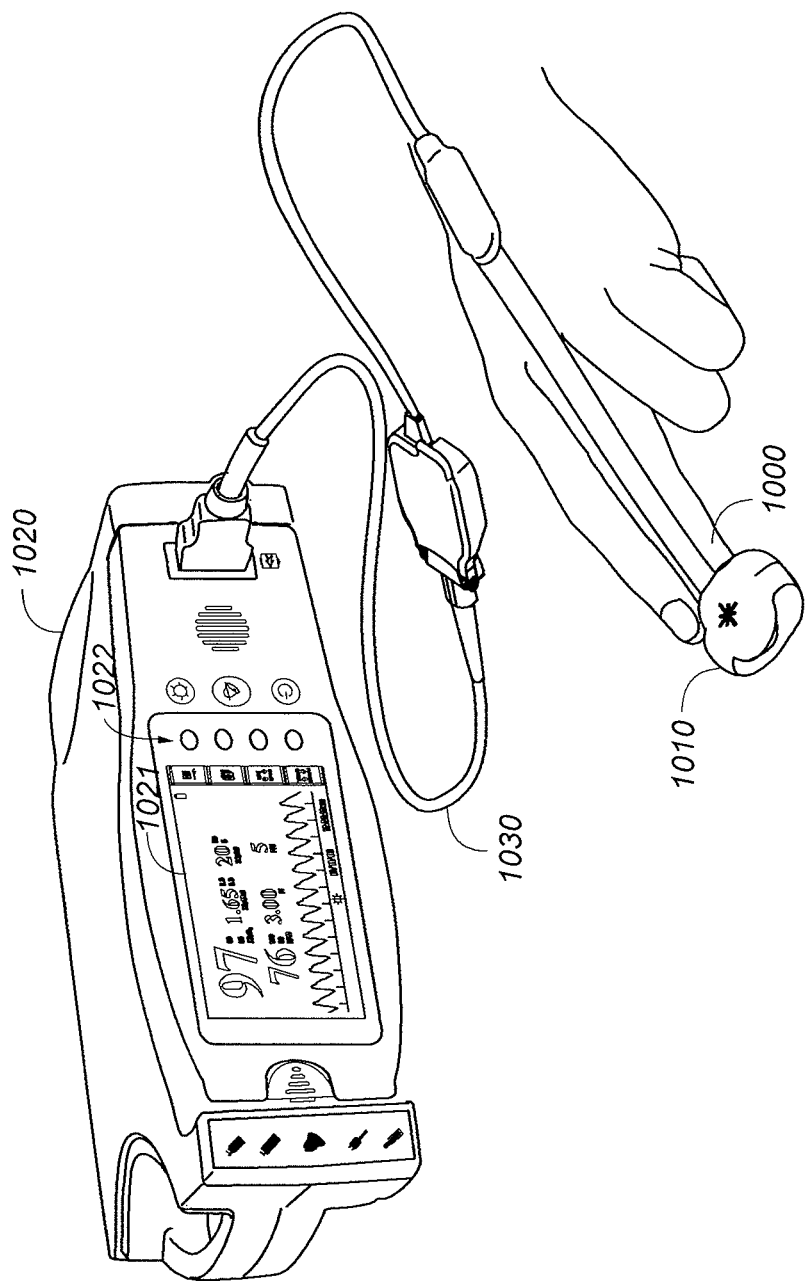
FIG. 10 is a perspective view of an advanced patient-monitoring system.

FIG. 10 illustrates a physiological measurement system having a noninvasive sensor 1010 attached to a tissue site 1000, a patient monitor 1020, and an interface cable 1030 interconnecting the monitor 1020 and the sensor 1010. The physiological monitoring system may incorporate pulse oximetry in addition to advanced features, such as a multiple wavelength sensor and advanced processes for determining physiological parameters other than or in addition to those of pulse oximetry, such as carboxyhemoglobin, methemoglobin and total hemoglobin, as a few examples. The patient monitor 1020 has a proximity display 1021 that presents measurements of selected physiological parameters and that also provides visual and audible alarm mechanisms that alert a caregiver when these parameters are outside of predetermined limits. The patient monitor 1020 also has keys 1022 for controlling display and alarms functions, among other items. The proximity display 1021 and keys 1022 provide a user interface that organizes many parameters so that a caregiver can readily ascertain patient status using, for example, a portable, handheld device.

Figure 11:
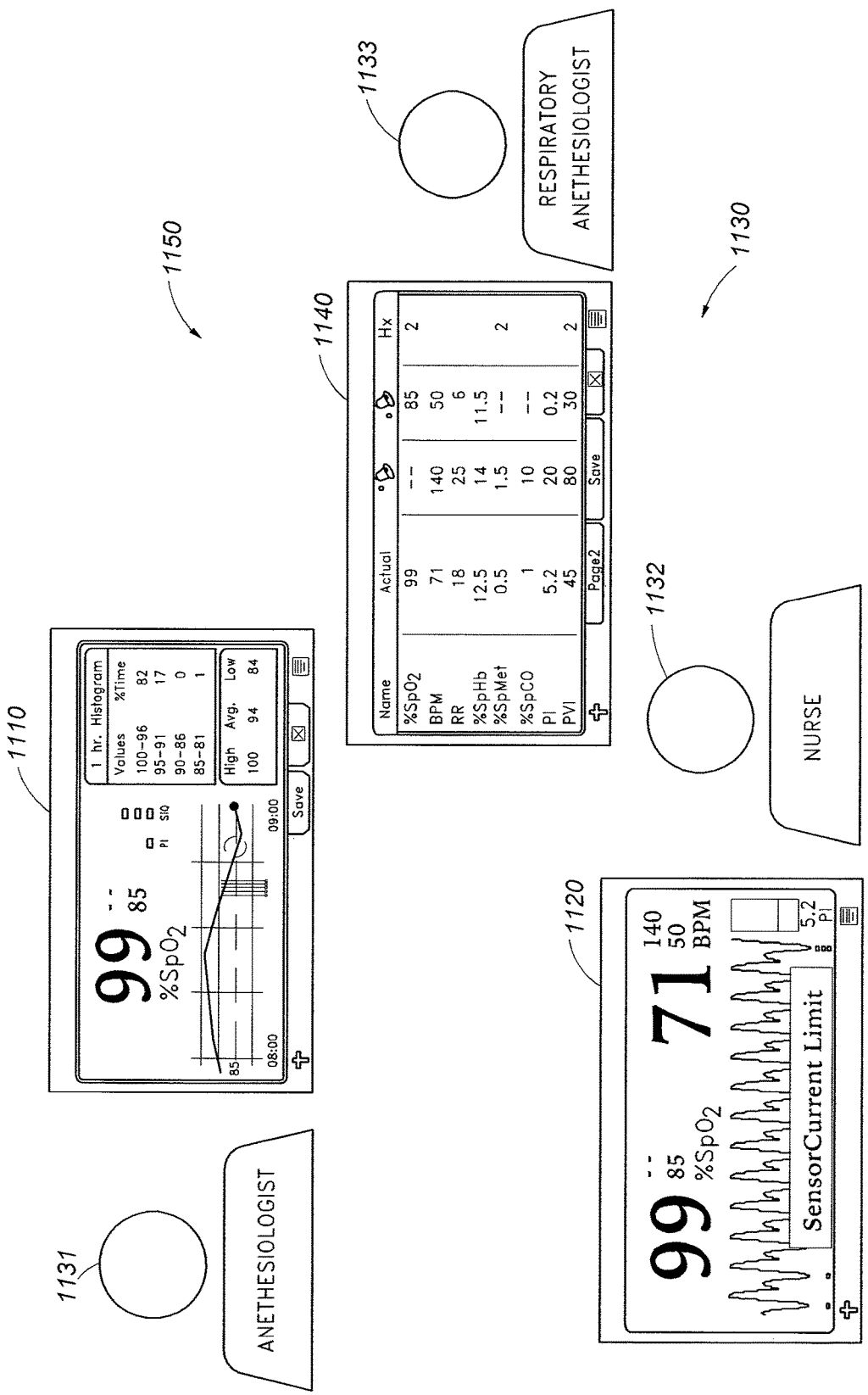
FIG. 11 illustrates a proximity display in a multi-user environment.

FIG. 11 illustrates various screens 1150 for a proximity display 1021 (FIG. 10) advantageously configured to respond to the presence of a particular user 1130 and to that user's display preference. Users may be any of various caregivers such as treating physicians or attending nurses. In an embodiment, the proximity display 1021 (FIG. 10) may also respond to any of a particular group of users.

As described with respect to FIG. 13, below, the presence or proximity of a particular user or group of users to the monitor 1020 (FIG. 10) may be determined by a user wearing an RFID (radio frequency identification) tag or other wireless communications. Then, a particular screen or screens can be presented on the display according to a predetermined display preference associated with the user. In this manner, a proximity display 1021 (FIG. 10) is tailored to the preferences of monitor users. An "RFID tag" or simply "tag" can include any wireless communication device that can remotely identify a proximate user to a monitor. Tags include, but are not limited to, devices in the form of badges, tags, clip-ons, bracelets or pens that house an RFID chip or other wireless communication components. Tags also encompass smart phones, PDAs, pocket PCs and other mobile computing devices having wireless communications capability.

As shown in FIG. 11, by example, an anesthesiologist 1131 proximate the monitor is identified and the display is changed to a screen 1110 showing pulse rate trend. When a nurse 1132 is proximate the monitor, the display is changed to a screen 1120 showing pulse oximetry parameters, a plethysmograph and alarm limits. When a respiratory therapist 1133 is proximate the monitor, the display is changed to a screen 1140 showing pulse oximetry, abnormal hemoglobin and perfusion indices.

In some embodiments, a proximity display monitor responds to the departure of all proximate users by automatically dimming the display to a reduced brightness setting. This feature advantageously avoids disturbance of a patient who is sleeping or attempting to sleep. In some embodiments, a proximity display monitor responds in a similar manner by automatically silencing pulse "beeps" and other non-critical sounds when there are no proximate users.

Figure 12:
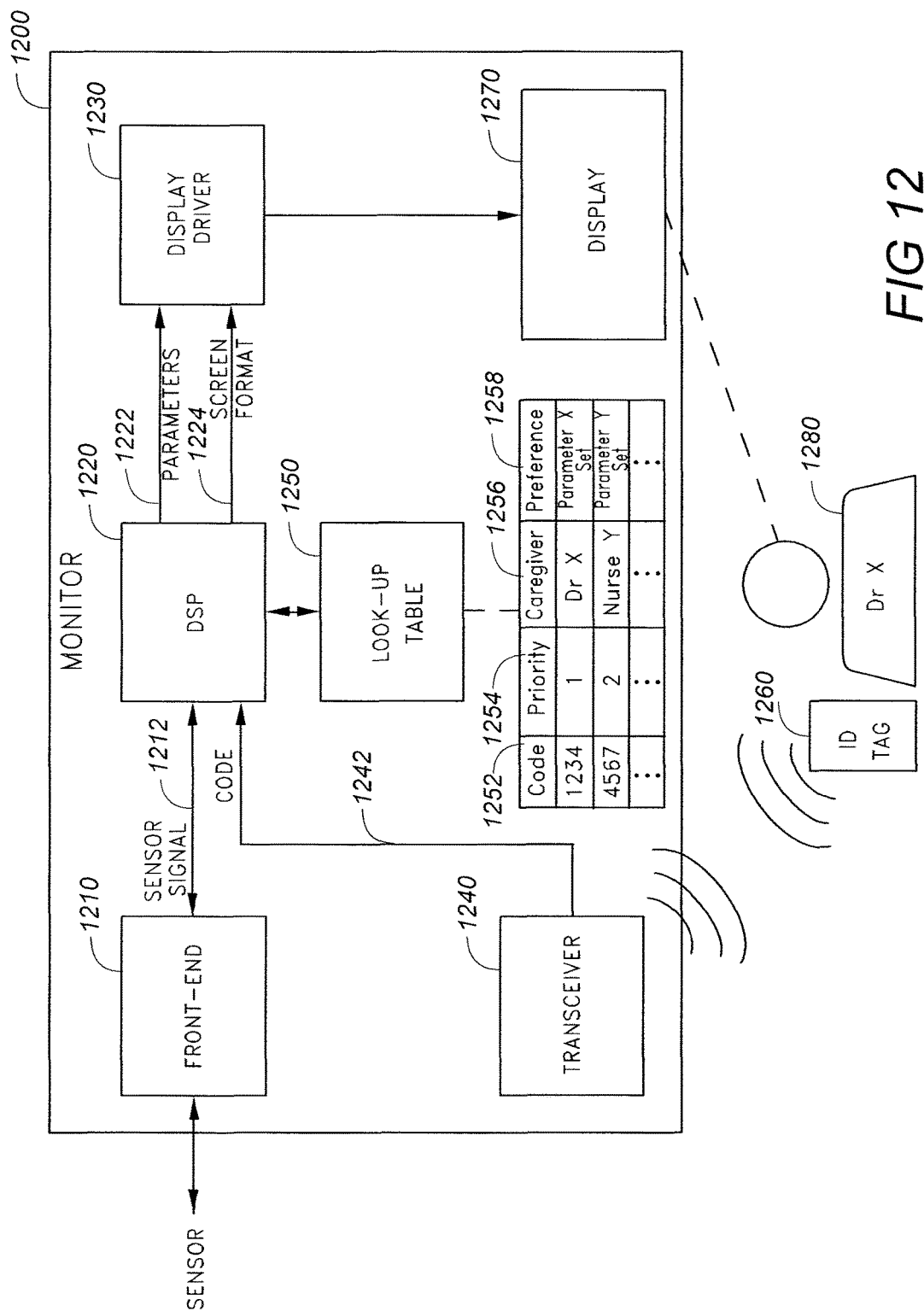
FIG. 12 is a general block diagram of a proximity display monitor.

FIG. 12 illustrates a proximity display monitor 1200 that responds to a nearby user 1280 so as to display calculated parameters according to a user display preference. As shown in FIG. 12, the proximity display monitor 1200, in some embodiments, has a front-end 1210 that interfaces with an optical sensor (not shown). The optical sensor generates a sensor signal responsive to pulsatile blood flow with a patient tissue site. An optical sensor is described in U.S. patent application Ser. No. 11/367,013 titled Multiple Wavelength Sensor Emitters, cited above. The front-end 1210 conditions and digitizes the sensor signal 1212, which is input to a digital signal processor (DSP) 1220. The DSP 1220 derives physiological parameters 1222 according to the sensor signal 1212. The calculated parameter values are communicated to a display driver 1230, which presents the parameters on the display 1270 according to a predetermined format. A monitor having a front-end and DSP is described in U.S. patent application Ser. No. 11/366,208 titled Noninvasive Multi-Parameter Patient Monitor, cited above.

Also shown in FIG. 12, the proximity display monitor 1200 has a transceiver or receiver 1240, a lookup table 1250 and display preferences 1258. The user 1280 has an ID tag 1260 that identifies the user 1280 to the transceiver 1240. When the user 1280 is in the vicinity of the proximity display monitor 1200, the ID tag 1260 is able to communicate with the transceiver 1240 so as to identify the user 1280. In an embodiment, the transceiver 1240 is an RFID reader and the ID tag 1260 has an embedded RFID chip containing a user code 1252. In another embodiment, the transceiver 1240 complies with one or more short-range wireless communications standards, such as Bluetooth®. The user 1280 can initiate communications with the proximity display monitor 1200 by, for example, pressing a button or similar initiator on the ID tag 1260, and a user code 1252 is transmitted to the transceiver 1240. The transceiver 1240 communicates the user code 1252 to the DSP 1220. The DSP can access the lookup table 1250 so as to derive a display preference 1258 from the received user code 1252. The display preference 1258 indicates the display parameters 1222 and screen format 1224, which are communicated to the display driver 1230.

Further shown in FIG. 12, in some embodiments, the lookup table 1250 relates the user code 1252 to a caregiver ID 1256 and a priority 1254. When multiple users are in the vicinity of the proximity display monitor 1200, the priority 1254 determines which display preference 1258 is used to configure the display 1270.

Figure 13:
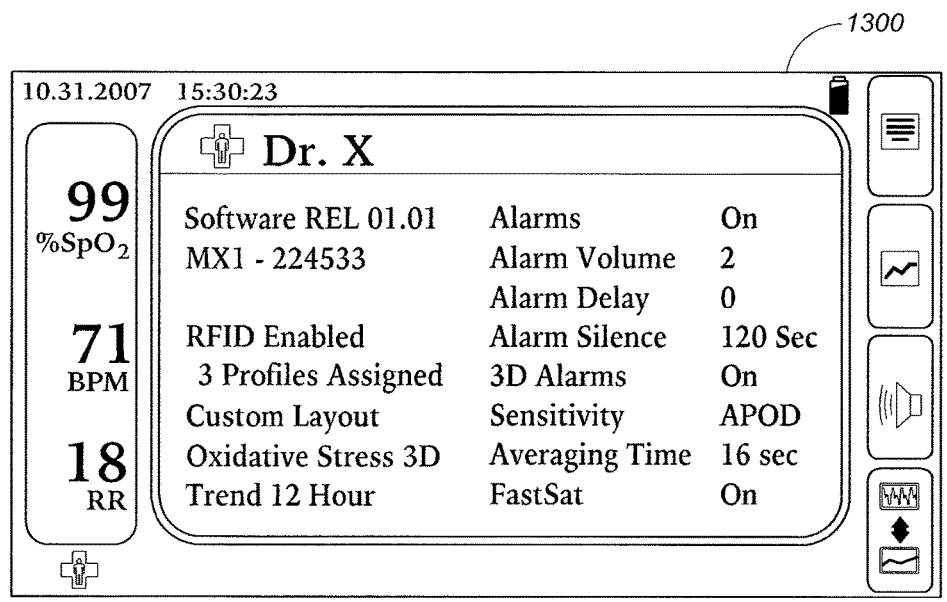
FIG. 13 illustrates a user display preference screen.

FIG. 13 illustrates a display preference screen 1300, which provides information for a particular row of the look-up table 1250 (FIG. 12). A setup or registration procedure allows users to specify one or more profiles including, for example, a display preference and various options for calculating parameters and triggering alarms.

Figure 14:
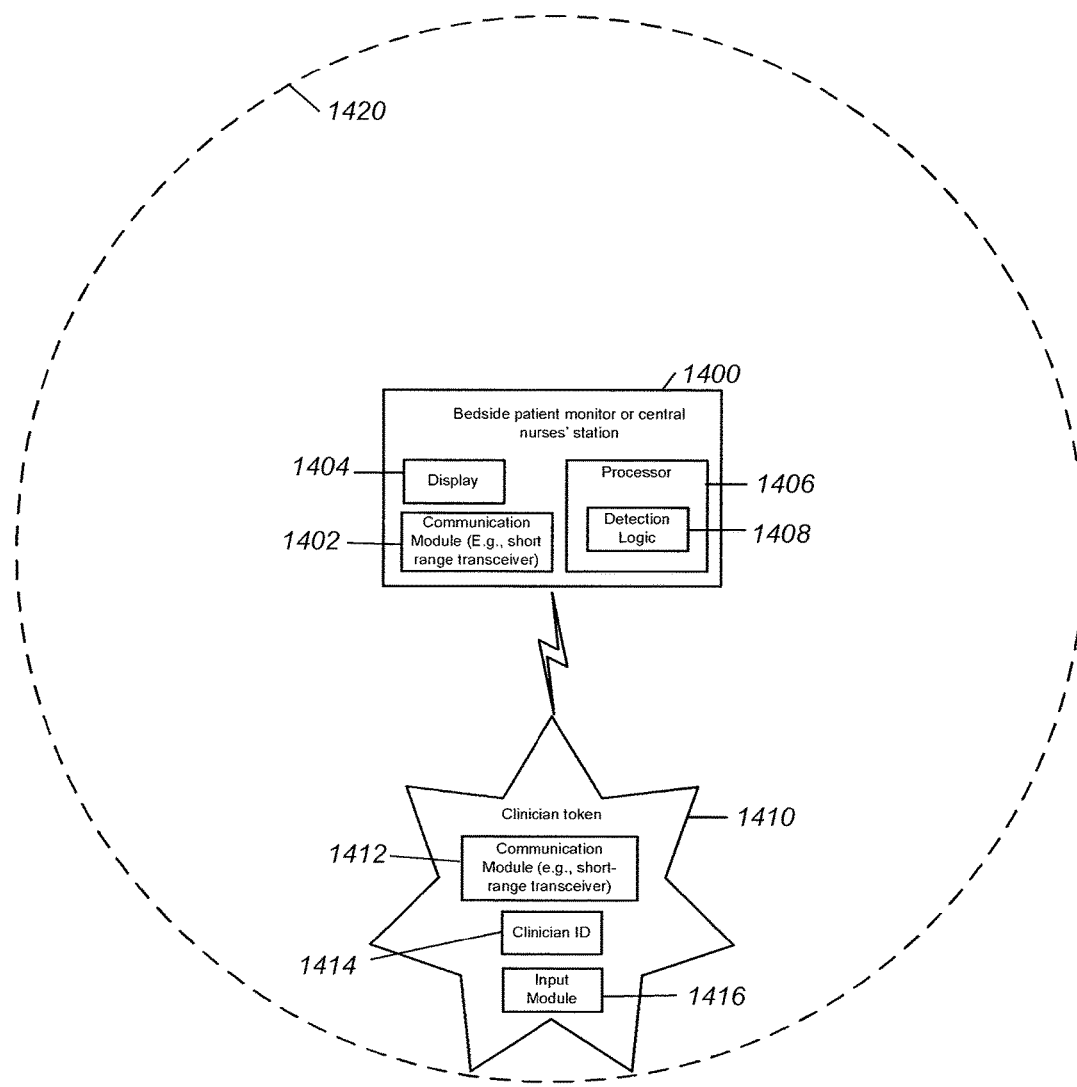
FIG. 14 is a schematic diagram of a patient monitoring device that is capable of automatically detecting the presence of a clinician token.

FIG. 14 is a schematic diagram of a patient monitoring device 1400 that is capable of automatically detecting the presence of a clinician token 1410. In some embodiments, the clinician token 1410 is a portable item meant to be, for example, worn or carried by a clinician throughout the day. The patient monitoring device 1400 is able to recognize the presence of the clinician based upon the presence of that clinician's token.

The patient monitoring device 1400 includes a detector such as, for example, a communication module 1402. The patient monitoring device 1400 also includes a display 1404, and a processor 1406. The processor 1406 can be used, for example, for carrying out clinically-useful tasks on the basis of physiological information collected from one or more patients (e.g., calculating physiological parameter values, determining alarm conditions, outputting physiological information via a clinician user interface, notifying a clinician of an alarm condition, etc.) The patient monitoring device 1400 can also include other modules to assist in the monitoring of patients, as described herein (e.g., an interface for receiving physiological information from a medical sensor or computer network, a user interface for facilitating interaction with a clinician, etc.). In some embodiments, the communication module 1402 is a transmitter, a receiver, or a transceiver. Other types of communication modules can also be used. In some embodiments, the communication module 1402 is a short-range transceiver. The short range transceiver can be, for example, a Bluetooth-enabled transceiver. Bluetooth is a wireless protocol for exchanging data between devices over relatively short distances. The communication module 1402 can also be an infrared transceiver, an RFID tag, or any other means of communication (e.g., short-range communication).

The communication module 1402 is capable, in some embodiments, of detecting signals from a remote device within a detection area 1420. The size of the detection area of 1420 can be determined by, for example, the power levels of communication signals from the communication module 1402. The size of the detection area 1420 may also be affected by the surroundings of the patient monitoring device 1400. In some embodiments, the detection area 1420 is configured to have a radius of 30 feet or less. In some embodiments, the radius of the detection area 1420 is 20 feet or less. In some embodiments, the radius is 10 feet or less, while in some embodiments, the radius is 5 feet or less, or 3 feet or less.

The clinician token 1410 can likewise include a communication module 1412, which can be, for example, a transmitter, a receiver, or a transceiver, though other types of communication modules may also be used. As is the case with the patient monitoring device 1400, the communication module 1412 included with the clinician token 1410 may be a short range transceiver, such as, for example, a Bluetooth transceiver. The patient monitoring device 1400 is capable of detecting the presence of a clinician based on, for example, recognition of one or more communication signals from a clinician token 1410. A communication signal from the clinician token 1410 may come, for example, in response to a communication initiated by the patient monitoring device 1400, or the communication signal from the clinician token 1410 may be initiated by the clinician token itself. Many different methods can be used for initiating, for example, wireless communication between remote devices.

The clinician token 1410 may also carry information, for example, in a memory. The memory may be, for example, volatile or nonvolatile memory. The information may be hardwired into the clinician token 1410 or programmable. In some embodiments, the clinician token 1410 includes a clinician ID 1414 that is unique to the clinician to whom the clinician token 1410 is assigned. The clinician token 1410 may also include other information such as, for example, a clinician's login information (e.g., user name and password), a code or other indicator for initiating a predetermined action to be performed by the patient monitoring device 1400 upon recognition of the clinician's presence (logging in the clinician, setting configuration preferences of the patient monitoring device 1400, enabling a function, etc.).

The clinician token 1410 may also include an input module 1416 that allows the clinician to cause the communication module 1412 to remotely communicate with, for example, the patient monitoring device 1400, or some other device that forms a part of the hospital's patient monitoring network. For example, the input module 1416 may include one or more buttons, or other input devices, that allow the clinician to initiate a communication with the patient monitoring device 1400 for the purpose of having that device recognize the clinician's presence. In addition, the clinician may use the input module 1416 to, for example, call in an emergency response team if the clinician discovers that a particular patient is in need of emergency attention, or to silence a monitoring alarm. The input module 1416 can also be used for other purposes, depending upon the application.

In some embodiments, the clinician token 1410 is a cell phone, notebook computer, PDA device, headset, etc., any one of which may be, for example, Bluetooth-enabled. In some embodiments, the clinician token 1410 is the pager, or other notification device, used to notify clinicians of physiological parameter alarm conditions, as described herein. In some embodiments, the clinician token 1410 is an active or passive RFID tag. An active RFID tag may be WiFi-enabled, for example. In some embodiments, the clinician token 1410 is a barcode (e.g., two-dimensional or three-dimensional). In some embodiments, the clinician token 1410 is a part of the clinician's body. For example, the clinician token 1410 may be a fingerprint, a retina, the clinician's face, etc. In such embodiments, the clinician ID 1414 is actually a unique biometric signature of the clinician. The communication module 1402 may be selected based upon the type of clinician token 1410 with which it is to communicate. For example, the communication module 1402 in the patient monitoring device 1400 may be an RFID interrogator, a barcode scanner, a fingerprint scanner, a retina scanner, a facial recognition device, etc.

In some embodiments, the clinician token 1410 is advantageously a consumer device that can be registered with the patient monitoring device 1400 but that has no prior connection or relationship with, for example, the patient monitoring device 1400, a patient monitoring system, the hospital, etc. For example, the clinician token 1410 can be a consumer device that is not designed specifically for the purpose of communicating with the patient monitoring device 1400, or any other device configured to be able to detect the presence of the clinician token. Many clinicians will already own, for example, a cell phone which is carried on the clinician's person throughout the day for the clinician's personal use. In some embodiments, the clinician's personal electronic device can function as the clinician token 1414, for example, after a registration process that will be described herein. This can be advantageous because it does not require investment on the part of the hospital or other caregiver facility to provide each clinician with a special-purpose clinician token 1410. Nevertheless, in some embodiments, the clinician token 1410 is a special-purpose device provided to the clinician for the primary purpose of operating with, for example, patient monitoring devices (e.g., 1400) having presence detection functionality.

In some embodiments, the clinician token 1410 is capable of responding to, for example, interrogation from a patient monitoring device only with a fixed response signal (e.g., a clinician ID 1414). In some embodiments, however, the clinician token 1410 is capable of transmitting multiple, and/or variable, signals and information to the patient monitoring device 1400. The clinician token 1410 may include a processor capable of executing, for example, software applications that allow the clinician token 1410 the capability of a variety of intelligent communications with the patient monitoring device 1400.

In some embodiments, a registration process is completed before the clinician token 1410 is used with the patient monitoring device 1400 to implement presence detection functionality. For example, during a registration process, the clinician token 1410 may be endowed with a unique clinician ID 1414 assigned to a particular clinician. This clinician ID may be stored in a database that is, for example, accessible by the patient monitoring device 1400 such that the patient monitoring device 1400 can determine the identity of the clinician based upon the clinician ID 1414 stored in the clinician token 1410. The clinician ID 1414 can also be associated in the database with, for example, the clinician's assigned login information for accessing the patient monitoring device 1400.

The database can also store an indication of the action, or actions, that the clinician desires a particular patient monitoring device to take upon detection of the clinician's presence. The database can store the clinician's configuration preferences for the patient monitoring device. For example, the particular physiological parameters and other monitoring information that are shown on the display 1404 of the patient monitoring device 1400 may be configurable. In the case of bedside patient monitors, for example, the display 1404 may be capable of showing numerical indicators of a particular physiological parameter, graphical indicators of the physiological parameter, visual alarms, multiple physiological parameters simultaneously, signal quality of physiological parameter signals from a patient sensor, etc. The clinician's configuration preferences can indicate to the monitoring device 1400 what type of information to display and how to format the displayed information. The clinician's configuration preferences for the patient monitoring device 1400 can also include patient monitoring settings such as, for example, physiological parameter alarm limits.

In the case of, for example, a central monitoring station, such as the type described herein, the clinician's configuration preferences may likewise include the type and display format of a physiological parameter, or other monitoring information, that is shown for each of the patients being monitored at the central monitoring station. In addition, the clinician's configuration preferences can include a fixed or dynamic list of patient rooms, or patient names, to be displayed at the central monitoring station. These rooms, or patients, can be those currently assigned to that particular clinician, for example. In general, however, the clinician's configuration preferences that are associated with the clinician ID 1414 can include any configurable feature, aspect, or function of the patient monitoring device 1400.

The database can associate with the clinician ID 1414 a particular action that the clinician may wish to initiate upon entering the detection area 1420 of the patient monitoring device 1400. Examples of such actions that can be initiated automatically upon detection of the clinician's presence are described herein. In addition, in some embodiments, the database can also associate with the clinician ID 1414 a priority level. The priority level can indicate which clinician should be given priority access to a medical monitoring device 1400, for example, when multiple clinicians are detected in the detection area 1420 simultaneously.

In some embodiments, the clinician's assigned login information, monitoring device configuration preferences, list of actions to automatically initiate upon recognition of the clinician's presence, priority level, and/or other information can be stored by the clinician token 1410 itself. In such embodiments, this information may be transmitted directly to the patient monitoring device 1400 by the clinician token 1410 as opposed to the patient monitoring device 1400 obtaining the information from a database using the clinician ID 1414 stored on the token 1410. Other methods can also be used in order to associate, for example, a clinician ID 1414 with a predetermined action (e.g., logging in, configuration change, etc.) that the clinician wishes the patient monitoring device 1400 to take or assume when the clinician is in the detection area 1420 of the device 1400.

In some embodiments, once a registration process is complete, the patient monitoring device 1400 is capable of detecting the presence of a particular clinician based upon the clinician's token 1410, and of taking, for example, a clinician-specific action based upon recognition of the clinician's presence. In some embodiments, the processor 1406 of the patient monitoring device 1400 is configured to execute detection logic 1408 for determining when a clinician token 1410 is or is not present in the detection area 1420 of the monitoring device 1400. In some embodiments, the detection logic 1408 is a set of rules or other criteria that must be satisfied before a clinician token 1410 is determined to be present in the detection region 1420, or before some clinician-specific action is performed.

Figure 15:
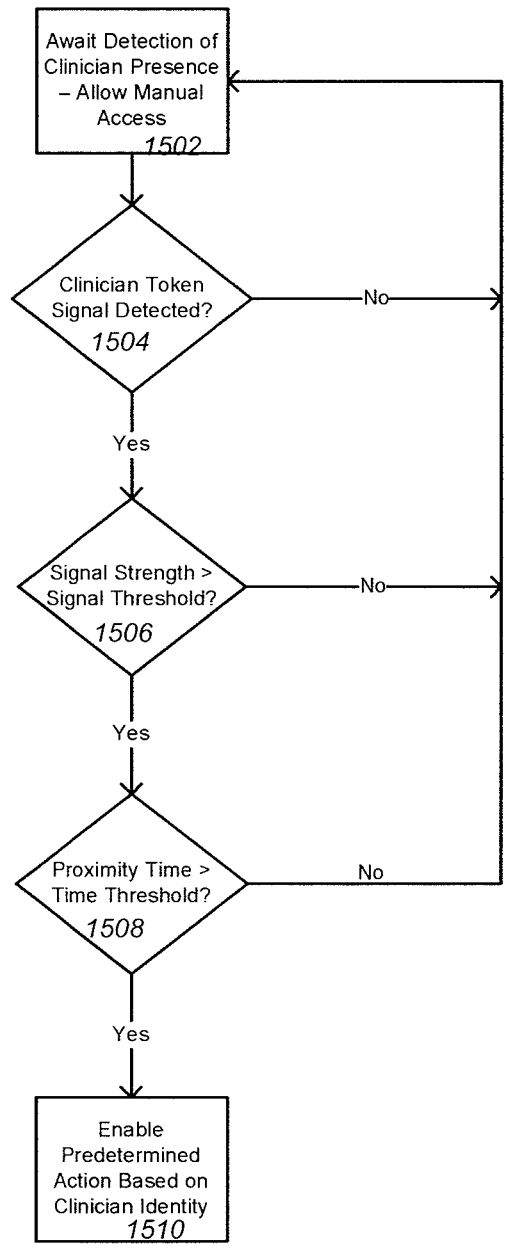
FIG. 15 is a flowchart illustrating detection method for detecting the presence of a clinician token within the detection region of a patient monitoring device.

FIG. 15 is a flowchart illustrating detection method 1500 for detecting the presence of a clinician token (e.g., 1410) within the detection region of a patient monitoring device. The detection method 1500 can begin, for example, at a waiting state 1502 where the patient monitoring device 1400 has not detected the presence of a clinician. In the waiting state 1502, the patient monitoring device 1400 can allow manual access, for example, to the features and information that can be provided by the device 1400. In the waiting state 1502, the patient monitoring device can also allow manual configuration of the device, or interaction with the device, by a clinician using an input device such as a keyboard, mouse, or touchscreen. Thus, the waiting state 1502 advantageously allows clinicians who may not have an assigned clinician token 1410 to nevertheless use and interact with the patient monitoring device 1400.

At decision block 1504, the processor 1406 executes the detection logic 1408 to determine whether a signal is detected from a clinician token 1410. For example, in some embodiments, the communication module 1402 of the patient monitoring device 1400 may, for example, continuously, or periodically, transmit a clinician token discovery signal. At decision block 1504, the processor 1406 can determine whether a response has been received from a clinician token 1410 to the patient monitoring device's discovery signal. Alternatively, or additionally, the clinician token 1410 can be configured to, for example, continuously, or periodically, transmit a discovery signal which the patient monitoring device 1400 can detect. Response signals from the clinician token 1410 can include, for example, the clinician ID 1414 or other information. If no signal is detected from a clinician token 1410, then the detection method 1500 returns to the waiting state 1502. If, however, a signal from a clinician token 1410 is detected, then the detection method 1500 can proceed to the next decision block 1506.

At decision block 1506, the processor 1406 executes the detection logic 1408 to determine whether the detected signal from the clinician token 1410 exceeds a signal strength threshold value. This test can be useful, for example, as an estimate of the physical distance between the clinician token 1410 and the patient monitoring device 1400. For example, the patient monitoring device 1400 may be configured such that whether or not a detection event occurs, and/or the particular predetermined action it takes upon detection of a clinician, is dependent upon the estimate of the physical distance between the clinician and the patient monitoring device 1400. This may be useful, for example, in the case of a central monitoring station that is near a high traffic area where many clinicians regularly pass by. In such situations it may be advantageous to set the signal strength threshold used in decision block 1506 at a relatively high level so as to limit the clinician detection events to situations where a clinician is a relatively small distance away from the central monitoring station. Thus, the signal strength threshold can be configurable based, for example, upon a desired physical distance from a clinician token 1410 before recognizing a clinician presence detection event. If the signal strength of the signal detected from a clinician token 1410 is below the signal strength threshold used by the decision block 1506, then the detection method 1500 returns to the waiting state 1502. If, however, the signal strength exceeds the threshold, then the detection method 1500 can proceed to the next decision block 1508.

At decision block 1508, the processor 1406 executes the detection logic 1408 to determine whether the signal strength of the signal from the clinician token 1410 has exceeded the signal strength threshold for a proximity time that is greater than a time threshold. This test can be useful to avoid recognizing a clinician presence detection event in cases where a clinician passes nearby the patient monitoring device 1400 but does so only transiently, not remaining within the detection region 1420 for a long enough period of time to merit a clinician presence detection event. This test can likewise help eliminate false clinician presence detection events in high-traffic areas around a patient monitoring device 1400 where many different clinicians routinely and regularly pass by. The proximity time threshold used by the decision block 1508 can be configurable. In some embodiments, the proximity time threshold may be set at, for example, 1 second, 2 seconds, or 5 seconds. Other proximity times can also be used, however. If the proximity time for a detected clinician token 1410 does not exceed the proximity time threshold used by decision block 1508, then the detection method 1500 returns to, for example, the waiting state 1502. If, however, the proximity time of the clinician token 1410 exceeds the proximity time threshold, then the detection method 1500 can proceed to block 1510.

At block 1510, a clinician presence detection event is recognized. At such time, the patient monitoring device 1400 can enable or initiate, for example, some predetermined action based upon the clinician identity associated with the recognized clinician token 1410. For example, the patient monitoring device 1400 can login the clinician, change a configuration setting, authorize some action or feature that is typically restricted absent the presence of a clinician, etc. In the detection method 1500 illustrated in FIG. 15, whether or not a clinician presence detection event occurs is dependent upon the signal strength of a signal from the clinician token 1410 as well as the length of time that the signal from the clinician token 1410 exceeds a signal strength threshold. In some embodiments, however, a clinician presence detection event can be recognized based only on signal strength from the clinician token 1410, or based only on the length of time that a signal is detected from a clinician token 1410.

In some embodiments, other factors can be included in the detection logic 1408, whether alone or in combination with signal strength from the clinician token 1410 and proximity time. For example, the recognition of a clinician presence detection event can be based, at least in part, on the identity of the clinician (some patient monitoring devices 1400 may only be accessible to certain clinicians). In addition, the recognition of a clinician presence detection event can be based upon the assigned priority of the clinician. For example, a nurse supervisor could be assigned a higher priority than other nurses on the shift such that the presence of the nurse supervisor will be recognized by a patient monitoring device 1400 even when the presence of another nurse has already been recognized by the device. The converse situation, however, may not result in a new clinician presence detection event; the detection of a lower priority clinician may not result in a detection event if the presence of a higher priority clinician has already been recognized by the patient monitoring device 1400. The priority level is one example of a tiebreaker criteria that can be used by the detection logic 1408 in the event that multiple clinician tokens meet the other requirements to initiate a clinician detection event at the same time. Other criteria can also be used in this tiebreaker role.

It should be appreciated that a wide variety of factors can be included in the detection logic 1408 depending upon the hospital, the type of medical equipment involved (e.g., patient monitoring equipment or some other type of medical device). In addition, such factors can be accounted for in the detection logic 1408 in a variety of ways. For example, the detection logic 1408 can determine when thresholds are exceeded, when a Boolean expression is true or false, when a fuzzy logic expression is true or false, when a mathematical equation is satisfied or not, when a compound rule is satisfied or not, etc.

When a clinician detection event has been realized according to, for example, the detection method 1500, the patient monitoring device 1400 can respond in a number of different ways. For example, the patient monitoring device 1400 can initiate a predetermined action based upon the identity of the clinician whose token has been detected in proximity to the monitoring device. In some embodiments, the predetermined action is that the patient monitoring device 1400 automatically logs the clinician in without requiring the clinician to, for example, physically interact with an input device. This process saves the clinician time and, in some cases, can also save patient lives. As described herein, the clinician's login information can be transmitted to the patient monitoring device 1400 from the clinician token 1410, or it can be retrieved from a database using the clinician ID 1414 from the token 1410.

In some embodiments, the patient monitoring device enables or disables a particular feature based upon detection of the clinician token 1410. For example, the patient monitoring device may enable/disable menus and buttons (e.g., alarm limit menu, alarm silence, all mute, etc.) based upon the credentials of the detected clinician. In some embodiments, the patient monitoring device 1400 begins transmission of patient monitoring information to a remote device upon detecting the presence of a clinician. For example, a bedside patient monitor capable of capturing breathing sounds from a patient could automatically begin transmission of those breathing sounds to the clinician's Bluetooth headset, which, incidentally, can serve as the clinician token 1410 as well. In other embodiments, the patient monitoring device 1400 could begin transmission of any type of monitoring information to a remote device via, for example, the Internet upon detecting the presence of a particular clinician. For example, the patient monitoring device 1400 can transmit the patient's oxygen saturation trend data to the clinician's computer for later analysis and diagnosis. The patient monitoring device 1400 can also transmit any other type of patient information (e.g., medical parameter values and/or trend data, video and/or audio from the patient's room, etc.)

to, for example, the clinician's computer, or some other device, in response to detection of the presence of some particular clinician in proximity to the patient monitoring device 1400.

Figure 16:
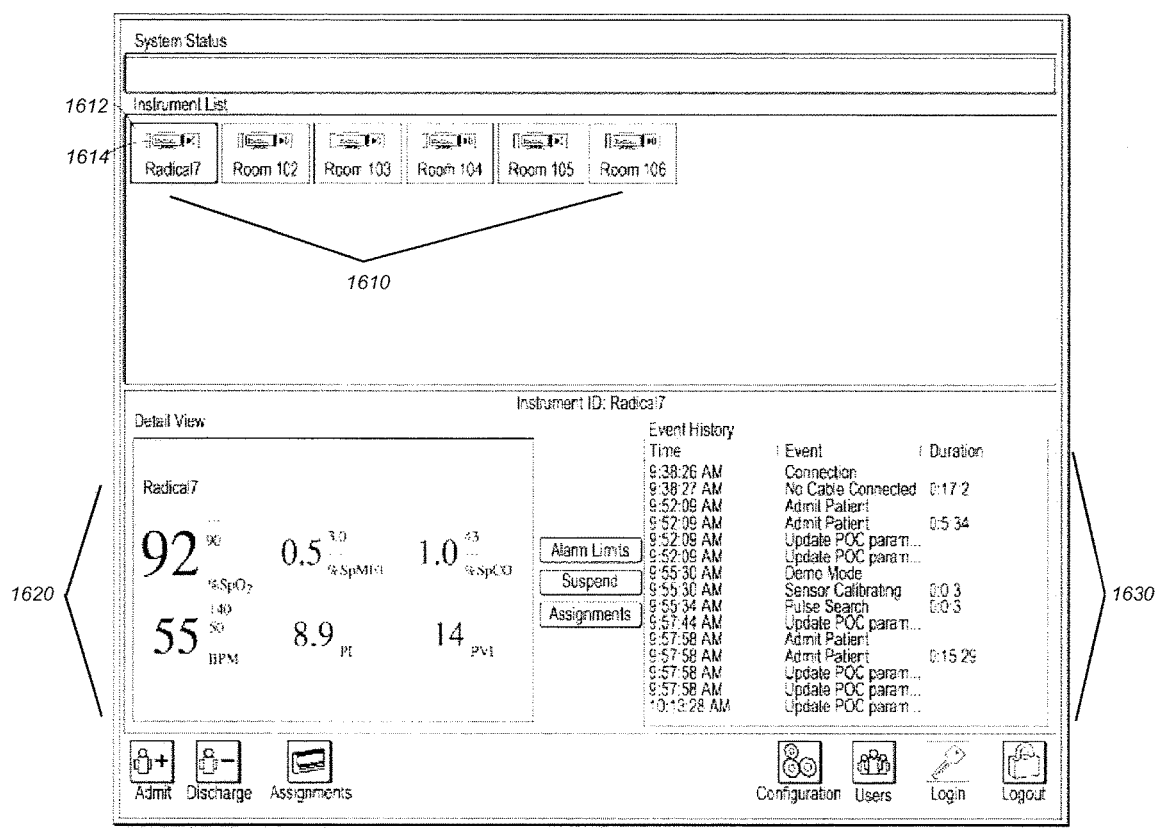
FIG. 16 illustrates an example graphical user interface of nurses' station or a central patient monitoring station.

In some embodiments, the patient monitoring device automatically updates its configuration based upon configuration preferences of a detected clinician. For example, the patient monitoring device 1400 could alter the content of the information it displays or the format of the information that it displays. These configuration changes can be made based upon settings that the clinician indicates during the registration process for the clinician token 1410. An example of such an embodiment is illustrated in FIG. 16. In some embodiments, a patient monitoring device changes the layout of a display screen (e.g., the number of parameters shown, the waveforms shown, trends, and other screen controls). Display layouts can be selected from predefined layouts, or a clinician can make a custom layout. The same is true of other configuration settings. Configuration settings can be associated with clinicians at an individual user or group level. A hierarchy of layouts modes can be established for layout conflicts.

The patient monitoring device 1400 can also update other configuration settings based upon registered preferences of the clinician. These can include physiological parameter alarm limits, alarm silence, all mute, averaging time, algorithm mode, etc., for example. In addition, the patient monitoring device 1400 could automatically create some type of report, such as a report of all alarm conditions that have been registered by that monitor over a predetermined period of time.

In addition, alarm annunciation and behavior can be altered in response to a clinician proximity detection event. For example, if the clinician is approaching a bedside patient monitoring device 1400 that is currently registering an alarm condition, the alarm can automatically be silenced in recognition that the clinician has entered within a certain radius of the monitoring device 1400. In some embodiments, the way that the patient monitoring device 1400 notifies of an alarm condition can be dependent upon the physical location of a clinician. For example, if the patient monitoring device 1400 detects an alarm condition while the clinician is already in proximity to the monitoring device, then it may emit no audible alarm or a lower-volume audible alarm. Alarm volume can also be adjusted in other ways based upon detected clinician presence. Similarly, in such a scenario, the patient monitoring device 1400 may be configured not to transmit an alarm to the central monitoring station. In some embodiments, a medical monitoring device does not notify or page other clinicians in case of an alarm if a clinician is already present. Alarm notification behavior of the medical monitoring device can be altered in a variety of ways based upon detected presence of a clinician. A medical monitoring device with clinician proximity awareness can allow a detected clinician to acknowledge his or her presence. As long as clinician presence is detected, the length of expiry of alarms can be changed (e.g., made longer).

In some embodiments, the patient monitoring device 1400 responds to detection of a clinician's presence by changing the language in which textual information is displayed by the monitoring device in accordance with language preferences of the clinician. In some embodiments, the patient monitoring device identifies and executes on-device confirmations that may be required for risk management based upon the detected clinician(s) in proximity to the monitoring device. In some embodiments, the patient monitoring device logs the number of clinician visits to a patient's bedside, the time of presence of each visit, the length of each clinician visit, the response time of clinicians to alarms, etc. A clinician may be permitted to chart parameters measured by the monitoring device to, for example, an electronic medical record with credentials based upon detection of clinician identity. Many other types of actions and/or configuration changes, or combinations of those described herein, can also be caused to automatically be initiated based upon the fact that a clinician has been detected in proximity to the patient monitoring device 1400.

FIG. 16 illustrates an example graphical user interface 1600 of nurses' station or central patient monitoring station. The graphical user interface 1600 includes features similar to those described with respect to FIG. 9. For example, the graphical user interface 1600 includes a patient status display area 1610. The patient status display area 1610 includes a plurality of patient status modules 1612, each having a graphical status indicator 1614. The graphical user interface 1600 also includes a patient monitor view area 1620 and a history view area 1630.

As illustrated in FIG. 9, the central patient monitoring station includes several patient status display areas, each showing monitoring information from a different patient. Unlike FIG. 9, however, which shows the status of a number of patients larger than a single nurse could possibly attend to individually, FIG. 16 shows only those patients assigned to a particular clinician. The display of the central patient monitoring station can be automatically updated from that of FIG. 9, for example, to that of FIG. 16 in recognition of the presence of a clinician. In this way, the clinician can quickly and conveniently check the status of each of his or her assigned patients at a glance by simply approaching the central patient monitoring station without having to actually physically interact with a central patient monitoring station. In addition, the proximity detection features described herein can be used to facilitate assignments of clinicians to patients at the nurses' station. For example, patients can be added to the view of FIG. 16 automatically if the clinician has been detected in proximity to the patient's bedside monitor within some predetermined period of time.

Figure 17:
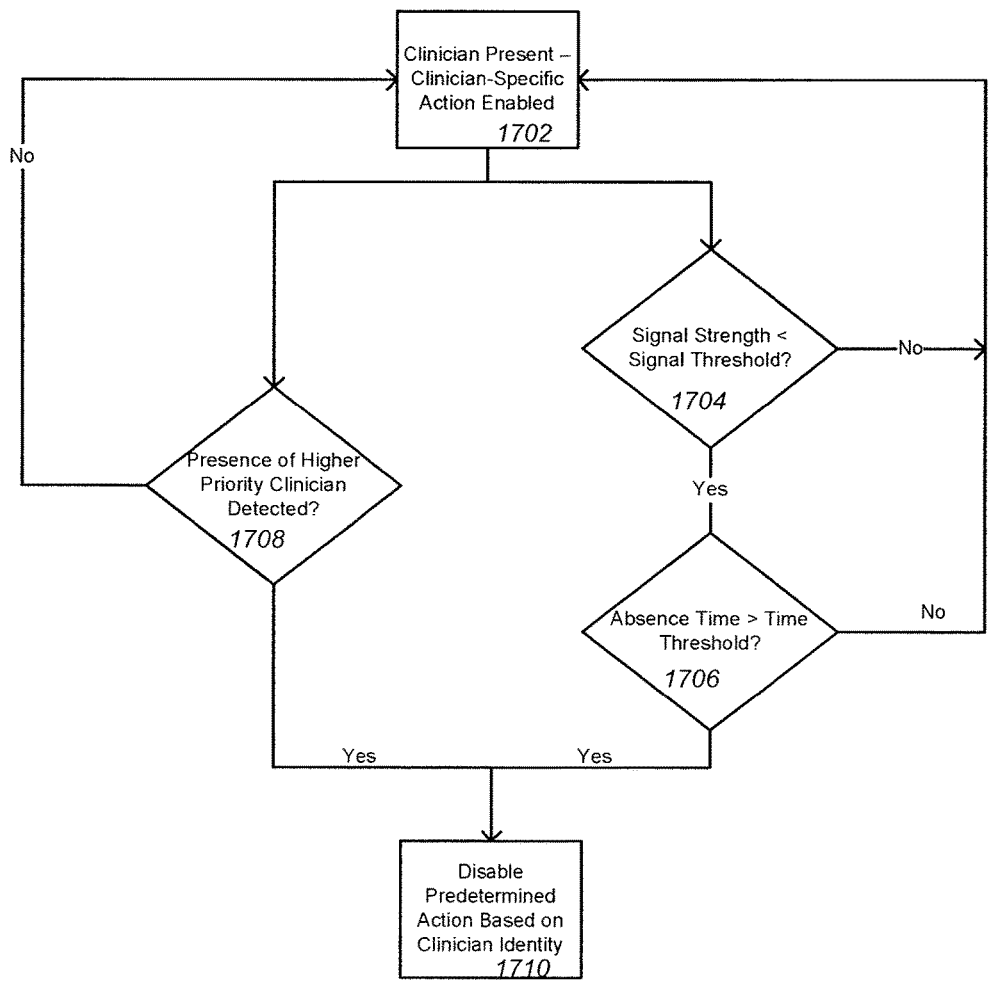
FIG. 17 is a flowchart illustrating a method for determining when to disable a clinician-specific action that had been previously enabled by a patient monitoring device based upon the detected presence of the clinician.

FIG. 17 is a flowchart illustrating a method 1700 for determining when to disable a clinician-specific action that had been previously enabled by a patient monitoring device 1400 based upon the detected presence of the clinician. The method 1700 begins at block 1702 where some clinician-specific action has been previously enabled, as described herein. The method 1700 then proceeds to decision block 1704 and decision block 1708. For example, the method 1700 may involve detecting whether a previously-detected clinician remains in proximity to a patient monitoring device while simultaneously detecting whether a higher priority clinician arrives in proximity to the patient monitoring device. For example, the process illustrated by decision block 1708 can generate an interrupt signal if the presence of a higher priority clinician is detected.

At decision block 1704, the processor 1406 executes the detection logic 1408 to determine whether the strength of a signal from the clinician token 1410 has fallen below a signal threshold. This threshold can be the same threshold as used by the decision block 1506 in FIG. 15. Alternatively, these two thresholds can be different to provide a degree of hysteresis in the detection system to guard against the situation where a clinician token 1410 could be recognized as switching between the present and absent states repeatedly in quick succession if the strength of the signal from the clinician token 1410 happens to be approximately equal to the selected threshold value. If the strength of the signal from the clinician token 1410 has not fallen below the signal threshold, then the method 1700 returns to block 1702 where the clinician-specific action remains enabled. If, however, the strength of the signal from the clinician token 1410 falls below the threshold used in decision block 1704, then the method 1700 proceeds to decision block 1706.

At decision block 1706, the processor 1406 executes the detection logic 1408 to determine whether the strength of the signal from the clinician token 1410 has fallen below the signal threshold for an absence time that is greater than a time threshold. Thus, the combination of decision blocks 1704 and 1706 determine whether the clinician token has been outside of a particular range for a particular amount of time. In some embodiments, this time threshold can be variable depending upon, for example, the content of information displayed by the medical monitoring device 1400. For example, if the monitoring device 1400 is displaying sensitive personal information, then the time threshold can be relatively short in order to protect the patient's confidentiality.

If the absence time does not exceed the time threshold used by the decision block 1706, then the method 1700 returns to block 1702 where the clinician-specific action remains enabled. If, however, the absence time exceeds the time threshold, then the method 1700 proceeds to block 1710. At block 1710, the clinician is recognized as no longer being in proximity to the patient monitoring device 1400. Therefore, the previously-enabled clinician-specific action is disabled. At such time, the patient monitoring device 1400 can return to a state similar to the waiting state 1502 described with respect to FIG. 15. In some embodiments, the action performed by the patient monitoring device 1400 at block 1710 can substantially reverse any action taken by the monitoring device at block 1510 in FIG. 15. For example, if the clinician was automatically logged in to the patient monitoring device 1400 when his or her presence was initially detected, then at block 1710, that clinician can be logged out. Similarly, if the configuration of the monitoring device 1400 was changed based upon the detected clinician's preferences, then, at block 1710, those configuration changes can be restored to, for example, a default state.

With reference now to the decision block 1708, the processor 1406 executes the detection logic 1408 to determine whether the presence of a higher priority clinician has been detected. The detection of such a clinician can proceed, for example according to the detection method 1500 described with respect to FIG. 15. As described herein, each clinician can be assigned a priority value that can act as a tiebreaker criteria to determine the presence of which clinician to recognize when more than one clinician is detected. If no higher priority clinician is detected at decision block 1708, then the method 1700 returns to block 1702. If, however, a higher priority clinician is detected at decision block 1708, then the method 1700 may proceed to block 1710 where the recognition of the presence of the previously-detected clinician is revoked, and the presence of the newly detected higher-priority clinician is recognized.

Figure 18:
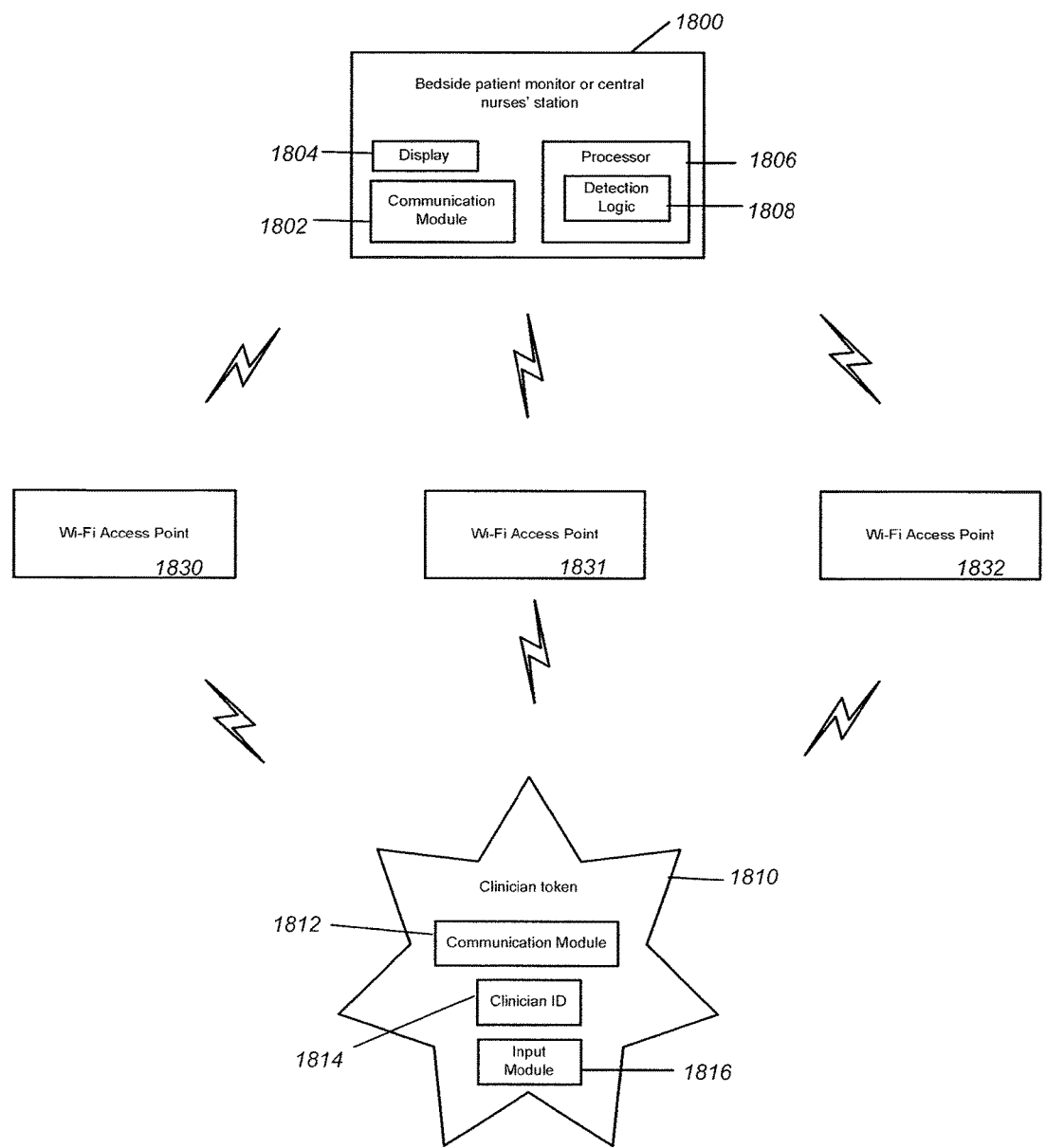
FIG. 18 is a schematic diagram of a system for enabling a patient monitoring device to automatically detect the presence of a clinician token.

FIG. 18 is a schematic diagram of a system for enabling a patient monitoring device 1800 to automatically detect the presence of a clinician token 1810. The patient monitoring device 1800 and the clinician token 1810 can be similar, for example, to the patient monitoring device 1400 and clinician token 1410 described herein with respect to FIG. 14 except as otherwise indicated. In the embodiment illustrated in FIG. 18, the patient monitoring device 1800 detects the presence of the clinician token 1810 with the assistance of, for example, one or more WiFi access points 1830-1832. The WiFi access points 1830-1832 can be advantageously distributed throughout the patient care environment where patient monitoring is occurring. The WiFi access points 1830-1832 can operate based on IEEE 802.11 standards, for example.

The communication module 1802 of the patient monitoring device 1800 can be, for example, a WiFi-enabled radio for communicating with the WiFi access points 1830-1832. In some embodiments, the clinician token 1810 is a WiFi-enabled RFID tag. By communicating with the WiFi access points 1830-1832, the patient monitoring device 1800 can triangulate its position relative to that WiFi access points. Likewise, the position of the clinician token 1810 can be triangulated. Thus, the distributed WiFi access points 1830-1832 can be used by, for example, the patient monitoring device 1800 in order to determine the approximate position of the clinician token 1810 with respect to the monitoring device 1800. In some embodiments, the patient monitoring device 1800 may also communicating directly with the clinician token 1810 in order to, for example, enhance the position approximation determined using the distributed WiFi access points 1830-1832.

Figure 19:
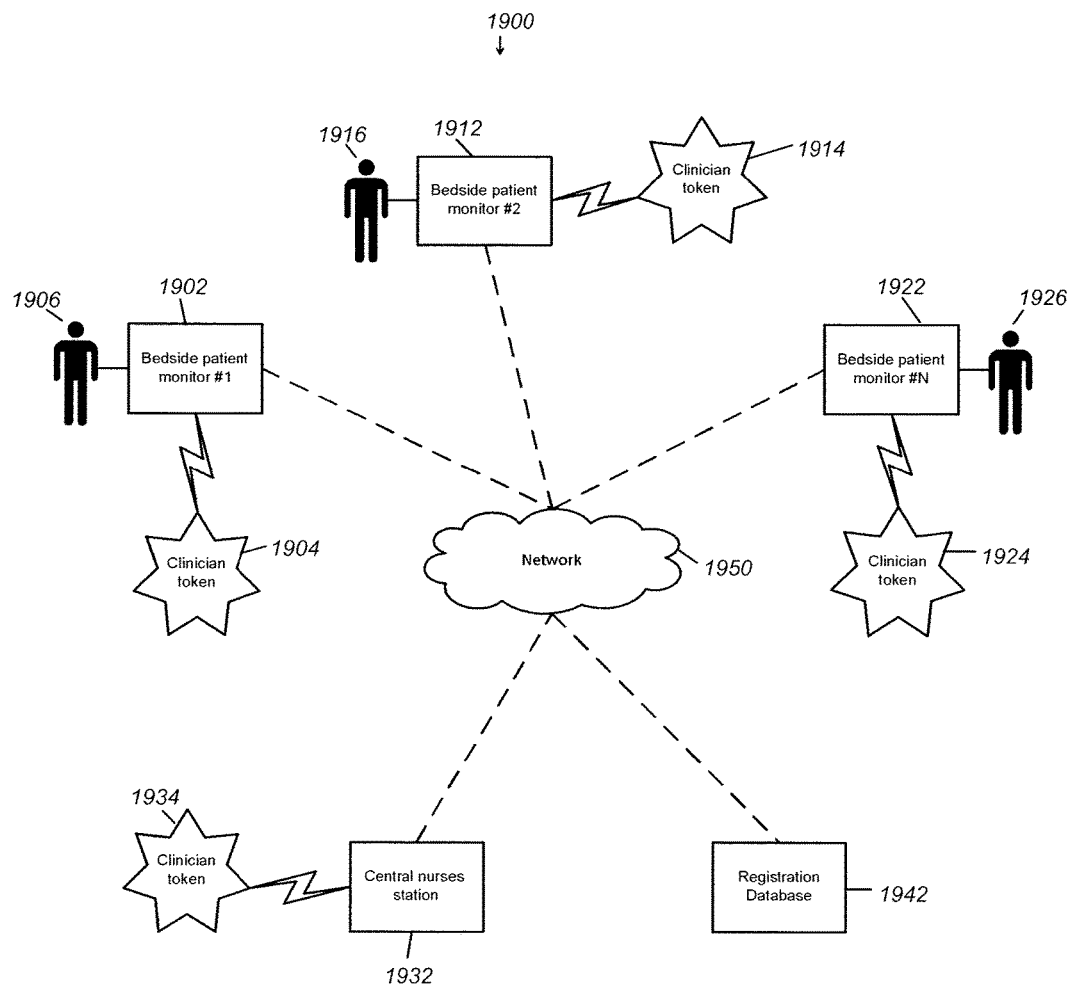
FIG. 19 is a schematic illustration of a patient monitoring device network having a clinician proximity awareness feature.

FIG. 19 is a schematic illustration of a patient monitoring device network 1900 having a clinician proximity awareness feature. The patient monitoring device network 1900 can be similar to those shown, for example, in FIGS. 1, 2, 6, and 7. The patient monitoring device network 1900 includes multiple bedside patient monitors 1902, 1912, 1922 for monitoring multiple patients 1906, 1916, 1926. In some embodiments, each of the bedside patient monitors 1902, 1912, 1922 is similar to those shown in, for example, FIG. 14 (1400) and FIG. 18 (1800). The bedside patient monitors 1902, 1912, 1922 are capable of detecting the presence of a clinician based upon the clinician tokens 1904, 1914, 1924. The clinician tokens 1904, 1914, 1924 can be similar, for example, to those shown in FIG. 14 (1410) and FIG. 18 (1810).

The patient monitoring device network 1900 also includes a nurses' station 1932 for remotely monitoring each of the patients 1906, 1916, 1926. The nurses' station, or central monitoring station, 1932 can be similar to those described herein. The patient monitoring device network 1900 may also include a registration database 1942. As described herein, the registration database 1942 can associate unique clinician IDs (e.g., 1414, 1814) carried by the clinician tokens 1904, 1914, 1924, 1934 with information for controlling the patient monitoring devices 1902, 1912, 1922, 1932 when the tokens are in the presence of those devices. For example, the registration database 1942 can associate each unique clinician ID with login information, configuration preferences, and predetermined actions for the monitoring devices to perform after recognizing the presence of a clinician.

In the illustrated patient monitoring device network 1900, each of the patient monitoring devices 1902, 1912, 1922, 1932 can communicate with one another via the network 1950. In some embodiments, the network 1950 uses open source communications standards in order to facilitate communication between various medical devices. Though not illustrated, the patient monitoring device network 1900 can also include WiFi access points, page transmitters, pagers, and other devices described herein.

Figure 20:
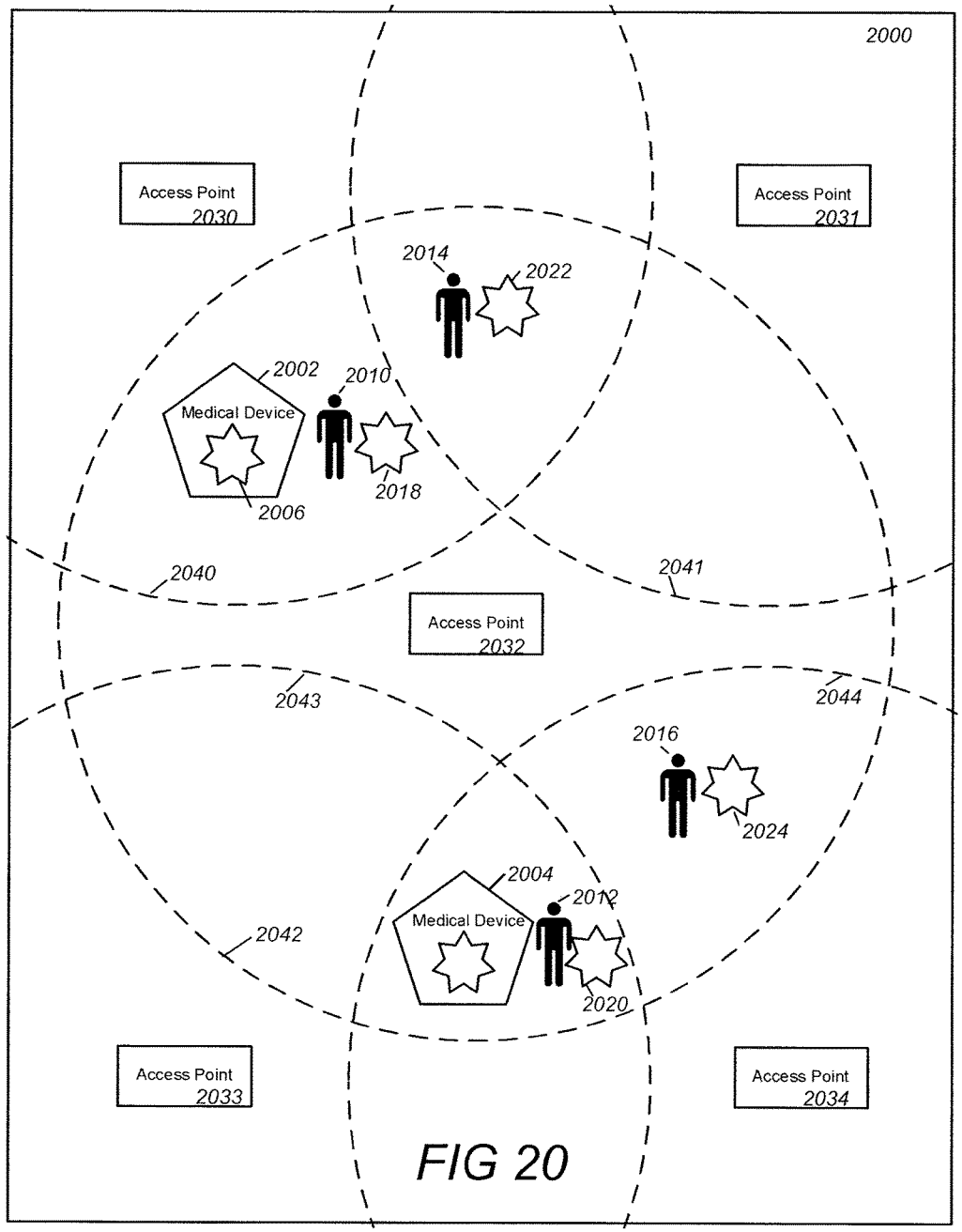
FIG. 20 is a schematic drawing of a hospital floor with distributed WiFi access points that can be used to estimate the physical locations of medical devices, patients, and clinicians.

FIG. 20 is a schematic drawing of a hospital floor 2000 with distributed WiFi access points 2030-2034 that can be used to estimate the physical locations of medical devices 2002, 2004, patients 2010, 2012, and clinicians 2014, 2016. The WiFi access points 2030-2034, or other detectors, can be distributed throughout the hospital floor, or other physical region, in order to provide WiFi coverage throughout the patient care area. In some embodiments, the WiFi access points 2030-2034 have respective coverage areas 2040-2044 that the overlap one another. In some embodiments, the WiFi access points 2030-2034 are populated densely enough so that at least three coverage areas 2040-2044 of the WiFi access points 2030-2034 overlap in substantially every portion of the hospital floor in which it is desired to track the positions of medical devices 2002, 2004, patients 2010, 2012, and clinicians 2014, 2016. The access points 2030-2034 can be mounted, for example, on or in walls, on or in ceilings, etc.

The medical devices 2002, 2004 can be similar to others described herein. For example, in some embodiments, the medical devices 2002, 2004 are patient monitoring devices. In some embodiments, the medical devices 2002, 2004 are fitted with tracking tags or tokens 2006, 2008. The tracking tags 2006, 2008 can be similar to the clinician tokens described herein. In some embodiments, the tracking tags 2006, 2008 are WiFi-enabled RFID tags, though other types of tracking tags may also be suitable. Each tracking tag 2006, 2008 can include an equipment ID.

As already discussed herein, the clinicians 2014, 2016 may carry clinician tokens 2022, 2024. The clinician tokens 2022, 2024 can be similar to those described herein. For example, in some embodiments, the clinician tokens 2014, 2016 are WiFi-enabled RFID tags. In some embodiments, each patient 2010, 2012 may also be fitted with a patient token 2018, 2020. The patient tokens 2018, 2020 can be similar to the clinician tokens described herein. In some embodiments, the patient tokens 2018, 2020 are WiFi-enabled RFID tags. These may be worn as bracelets, or otherwise suitably affixed to the patients. Each patient token 2018, 2020 can include a patient ID.

The distributed network of WiFi access points 2030-2034 can be used to communicate with the medical device tracking tags 2006, 2008, the clinician tokens 2022, 2024, and the patient tokens 2018, 2020 for the purpose of estimating the physical position of each of these tags and tokens in the hospital 2000. For example, the WiFi access points 2030-2034 can be used to triangulate the position of each tag or token.

While FIG. 20 illustrates a distributed network of WiFi access points 2030-2034 that can be used for detecting the positions of the tracking tags 2006, 2008, the clinician tokens 2022, 2024, and the patient tokens 2018, 2020, other devices can also be used for similar purposes. For example, in some embodiments, the WiFi access points 2030-2034 are eliminated and medical devices 2002, 2004 with short range transceivers, or other detectors, are used in their place to create an ad hoc network. Each medical device 2002, 2004 can serve as a node in the ad hoc network, and each node can share information about, for example, the patients 2010, 2012 and the clinicians 2014, 2016 around it. In some embodiments, the medical devices 2002, 2004 are Bluetooth-enabled, though other short range wireless communications standards can also be used.

If the hospital floor 2000 contains a number of medical devices that are arranged densely enough, then the distributed medical devices 2002, 2004 can serve as a network for tracking the location of, for example, Bluetooth-enabled medical device tracking tags 2006, 2008, patient tokens 2018, 2020, and clinician tokens 2022, 2024. In such an embodiment, the physical location of each tracking tag or token may only be identifiable if it is located within the range of a Bluetooth-enabled medical device. In addition, in some embodiments, the physical location of each tracking tag or token may not be able to be precisely identified, as each Bluetooth-enabled medical device may only be able to determine that the tracking tag or token is located somewhere within the medical device's detection area. Nevertheless, this level of tracking resolution may be sufficient in many cases.

In the embodiment illustrated in FIG. 20, a location monitoring server may be communicatively coupled to the WiFi access points 2030, 2034. The location monitoring server may be configured to track the estimated position of each medical device 2002, 2004, each patient 2010, 2012, and each clinician 2014, 2016. The location monitoring server may include a display to show this location information. In addition, the location monitoring server, or some other device, may execute logic that can be useful in enhancing features offered by the patient monitoring systems described herein. The location monitoring server may also be communicatively coupled to the medical devices 2002, 2004.

The system illustrated in FIG. 20 can be used, for example, to enhance the patient monitoring systems described herein. As already discussed, the patient monitoring systems described herein are capable of providing notifications to clinicians when, for example, a monitored patient's physiological parameter (e.g., SpO2, respiratory rate, etc.) triggers an alarm. In some embodiments, the clinician assigned to monitor the patient is notified first by, for example, a page, e-mail, text message, etc. If the first-notifying clinician does not respond within a set period of time, the patient monitoring system may be configured to execute an escalation algorithm whereby one or more additional clinicians are notified of the patient's alarm condition. In some embodiments, the clinician notifications that are sent out when an alarm condition exists can be controlled, at least in part, using location-based rules. For example, location-based rules can be used to determine which clinician is notified of an alarm condition initially, and which clinician, or clinicians, are notified if escalation becomes necessary. The location-based rules can receive as inputs information from the system illustrated in FIG. 20 regarding the physical locations of, for example, patients 2010, 2012 and/or clinicians 2014, 2016.

The location-based rules can be dependent upon, for example, the absolute or relative locations of the patient's 2010, 2012 and/or the clinicians 2014, 2016. For example, if the patient 2010 undergoes an alarm condition, that patient's previously assigned clinician can first be notified so long as he or she is present on the same floor of the hospital (or some other domain). In some embodiments, the clinician located the closest to the patient who is experiencing the alarm condition can be notified regardless of whether the clinician was previously assigned to the patient. In some embodiments, the closest clinician to the patient experiencing the alarm condition can be notified only after the regularly-assigned clinician fails to respond within a certain amount of time. In some embodiments, a nearby clinician is notified of the alarm condition if the alarm condition is particularly urgent and requires immediate attention. Many other location-based rules can also be implemented.

Location-based rules can also be used for controlling whether a clinician is permitted to deactivate an alarm. As disclosed herein, the clinician tokens 2022, 2024 may include an input module (e.g., 1416). One use for this input module is to remotely disable an alarm once the clinician has received notification of the alarm and is en route to the patient. However, in some embodiments, a location-based rule can be put into place that may prevent a clinician from remotely disabling an alarm if the clinician is, for example, more than some threshold distance away from the patient.

The location information provided by the system illustrated in FIG. 20 can also be used to provide alerts to clinicians when a patient 2010, 2012 strays more than some threshold distance from the monitoring device assigned to the patient. While some examples of location-based rules have been discussed in the context of patient monitoring systems, the information provided by the system illustrated in FIG. 20 can be used to implement a variety of location-based rules for many different kinds of medical devices. Such location-based rules can include, for example, any rule for determining an action to be performed where the selected action is dependent in whole, or in part, upon the estimated physical location of a device, clinician, and/or patient.

In some embodiments, location-based rules can also be provided for configuring the medical devices 2002, 2004 (e.g., to configure patient monitoring settings). For example, patient monitoring devices of the type described herein are sometimes configured with different physiological parameter alarm limits depending upon the patient ward that they are located in. For example, alarm limits for the pulse rates of neonates should generally be set differently than for the pulse rates of adults. Therefore, it may be desirable to provide a notification to a clinician if an attempt is made to monitor a patient located outside of the nursery using a monitoring device whose alarm limits have been set for neonates. This can be done since the location of the medical device can be detected by the system illustrated in FIG. 20. Other monitoring device configuration settings can also be recommended to clinicians, or automatically set, based upon the physical location of the monitoring device. In some embodiments, the configuration settings and techniques disclosed in US Patent Publication 2009/0275844, the entire contents of which are hereby incorporated by reference herein, can be controlled using the location-based rules described herein.

FIGS. 21A-F, FIGS. 22A-E, and FIGS. 23A-C illustrate proximity displays 2100, 2200, 2300 that feature a multi-sided animation that appears to rotate from a first screen to a preferred screen in response to user proximity. This feature advantageously provides feedback to the user that the monitor has received an identification signal from the user, as described above, and has recognized the user's presence. As examples, the multi-sided presentation may be any of a triangular-shaped, a cubic-shaped or a planar solid having multiple facets and a different screen preference on two or more of the facets. One of ordinary skill will recognize that many other rotating geometric shapes can provide similar user feedback, including un-faceted shapes such as a sphere or cylinder. These multi-sided presentations are described in further detail below.

FIGS. 21A-F illustrate a proximity display 2100 embodiment that utilizes a rotating triangular solid 2105 to depict transitions between multiple screens that correspond to different display preferences of monitor users that enter or exit proximity to the monitor. In particular, the triangular solid 2105 has a first side 2101, a second side 2102 and a third side 2103 configured to display different user preferences of patient monitoring information in response to user proximity to the display. Further, the triangular solid 2105 is shown to rotate during a transition between the sides 2101, 2102, 2103 so as to provide feedback to a proximate user.

As shown in FIG. 21A, the first side 2101 relating to a first user is shown in the display 2110. As shown in FIG. 21B, when a second user is proximate the display, the monitor identifies the second user, as described with respect to FIG. 7 below, and virtually rotates the triangular solid 2105 from the first side 2101 to the second side 2102. As shown in FIG. 21C, the display 2110 then shows the second side 2102, corresponding to the second user's display preference. As shown in FIG. 21D, when a third user enters proximity to the monitor, the monitor identifies the third user and virtually rotates the triangular solid 2105 from the second side 2102 to a third side 2103. As shown in FIG. 21E, the display 2110 then shows the third side 2103, corresponding to the third user's display preference. As shown in FIG. 21F, when the first user is again identified, the display 2110 virtually rotates the triangular solid back to the first side 2101. In this manner, the sides 2101, 2102, 2102 of the triangular solid 2105 are alternatively shown on the display 2110 according to different user preferences and based upon user proximity to the monitor. As described with respect to FIG. 13 if several users are in proximity to the monitor at once, then priority or acknowledgement schemes are utilized to determine which screen to display.

FIGS. 22A-E illustrate a proximity display 2200 embodiment that utilizes a rotating cube 2205 to depict transitions between multiple screens that correspond to different display preferences of monitor users that enter or exit proximity to the monitor. In particular, the cube 2205 has a first side 2201, a second side 2202 and a third side 2203 configured to display different user preferences of patient monitoring information in response to user proximity to the display. Further, the cube 2205 is shown to rotate during a transition between the sides 2201, 2202, 2203 so as to provide feedback to a proximate user, in a manner similar to that described in detail with respect to FIGS. 21A-F, above.

Figure 23C:
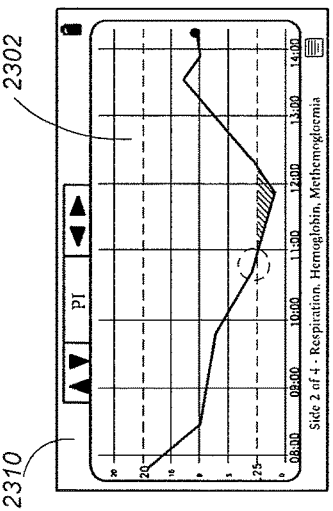
Figure 23B:
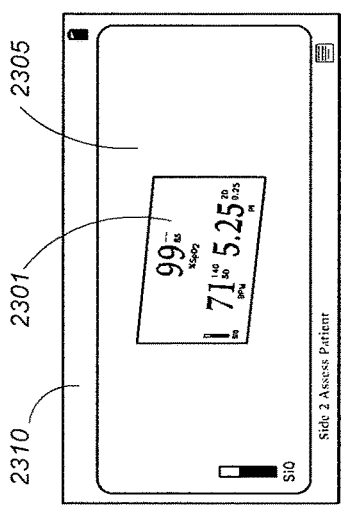
Figure 23A:
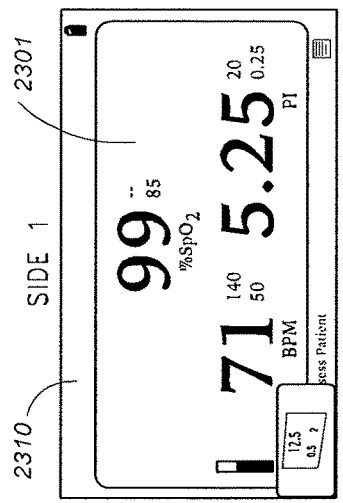

FIGS. 23A-C illustrate a proximity display 2300 embodiment that utilizes a rotating planar solid 2305 to depict transitions between multiple screens that correspond to different display preferences of monitor users that enter or exit proximity to the monitor. In particular, the planar solid 2305 has a first side 2301 and a second side 2302 configured to display different user preferences of patient monitoring information in response to user proximity to the display. Further, the planar solid 2305 is shown to rotate during a transition between the sides 2301, 2302 so as to provide feedback to a proximate user, in a manner similar to that described in detail with respect to FIGS. 21A-F and FIGS. 22A-E, above.

Although some features are described herein with respect to a bedside monitor, a proximity display is applicable to any monitoring device, medical or non-medical and at any location, such as at bedside or at central monitoring, such as a nurse's station. Further, a proximity display is applicable during physiological data collection or other monitor uses, such as historical data review, setting and verification of alarm limits and installation of software updates by medical personnel or equipment maintenance staff, to name a few.

Translation of Medical Communication Protocols to Facilitate Communication between Devices and Systems Healthcare costs have been increasing and the demand for reasonably-priced, high-quality patient care is also on the rise. Health care costs can be reduced by increasing the effectiveness of hospital information systems. One factor which may affect the efficacy of a health institution is the extent to which the various clinical computer systems employed at the health institution can interact with one another to exchange information.

Hospitals, patient care facilities, and healthcare provider organizations typically include a wide variety of different clinical computer systems for the management of electronic healthcare information. Each of the clinical computer systems of the overall IT or management infrastructure can help fulfill a particular category or aspect of the patient care process. For example, a hospital can include patient monitoring systems, medical documentation and/or imaging systems, patient administration systems, electronic medical record systems, electronic practice management systems, business and financial systems (such as pharmacy and billing), and/or communications systems, etc.

The quality of care in a hospital or other patient care facility could be improved if each of the different clinical computer systems across the IT infrastructure were able to effectively communicate with each other. This could allow for the exchange of patient data that is collected by one clinical computer system with another clinical computer system that could benefit from such patient data. For example, this may allow decisions relating to patient care to be made, and actions to be taken, based on a complete analysis of all the available information.

In current practice, individual clinical computer systems can be, and often are, provided by different vendors. As a result, individual clinical computer systems may be implemented using a proprietary network or communication infrastructure, proprietary communication protocols, etc.; the various clinical computer systems used in the hospital cannot always effectively communicate with each other.

Medical device and medical system vendors sometimes develop proprietary systems that cannot communicate effectively with medical devices and systems of other vendors in order to increase their market share and to upsell additional products, systems, and/or upgrades to the healthcare provider. Thus, healthcare providers are forced to make enterprise or system-wide purchase decisions, rather than selecting the best technology available for each type of individual clinical computer system in use.

One example where this occurs is in the area of life-saving technology available for patient monitoring. For example, many different bedside devices for monitoring various physiological parameters are available from different vendors or providers. One such provider may offer a best-in-class device for monitoring a particular physiological parameter, while another such provider may offer the best-in-class device for another physiological parameter. Accordingly, it may be desirable in some circumstances for a hospital to have the freedom to use monitoring devices from more than one manufacturer, but this may not be possible if devices from different manufacturers are incapable of interfacing and exchanging patient information. Accordingly, the ability to provide reasonably-priced, high-quality patient care can be compromised. In addition, since each hospital or patient care facility may also implement its own proprietary communication protocols for its clinical computer network environment, the exchange of information can be further hindered.

The Health Level Seven ("HL7") protocol has been developed to provide a messaging framework for the communication of clinical messages between medical computer systems and devices. The HL7 communication protocol specifies a number of standards, guidelines, and methodologies which various HL7-compliant clinical computer systems can use to communicate with each other.

The HL7 communication protocol has been adopted by many medical device manufacturers. However, the HL7 standard is quite flexible, and merely provides a framework of guidelines (e.g., the high-level logical structure of the messages); consequently, each medical device or medical system manufacturer or vendor may implement the HL7 protocol somewhat differently while still remaining HL7-compliant. For example, the format of the HL7 messages can be different from implementation to implementation, as described more fully herein. In some cases, the HL7 messages of one implementation can also include information content that is not included in messages according to another HL7 implementation. Accordingly, medical devices or clinical computer systems that are all HL7-compliant still may be unable to communicate with each other.

Consequently, what is needed is a module that can improve the communication of medical messages between medical devices or systems that use different allowed implementations of an established communication protocol (e.g., HL7), thereby increasing the quality of patient care through the integration of multiple clinical computer systems.

Figure 24A:
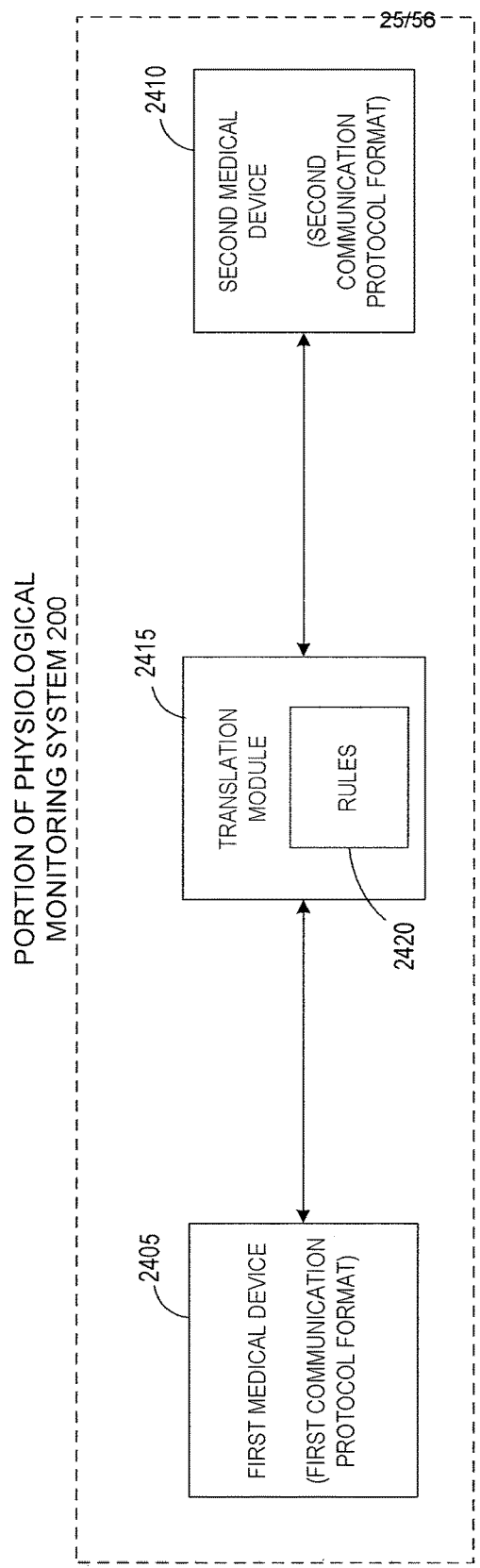
FIG. 24A illustrates a first medical device and a second medical device that communicate with one another via a translation module.

FIG. 24A illustrates a first medical device 2405 and a second medical device 2410 that communicate with one another via a translation module 2415. The first medical device 2405 is configured to transmit and receive messages according to a first allowed format or implementation of an accepted electronic medical communication protocol, while the second medical device 2410 is configured to transmit and receive messages according to a second allowed format or implementation of the electronic medical communication protocol. In some embodiments, the first and second protocol formats are different implementations of the HL7 communication protocol. Other electronic medical communication protocols besides HL7 can also be used.

The translation module 2415 receives input messages having the first protocol format from the first medical device 2405 and generates output messages to the second medical device 2410 having the second protocol format. The translation module 2415 also receives input messages having the second protocol format from the second medical device 2410 and generates output messages to the first medical device 2405 having the first protocol format. Thus, the translation module 2415 enables the first and second medical devices 2405, 2410 to effectively and seamlessly communicate with one another without necessarily requiring modification to the communication equipment or protocol implemented by each device.

In certain embodiments, the translation module 2415 determines the protocol format expected by an intended recipient of the input message based on, for example, the information in the input message or by referencing a database that stores the protocol format used by various devices, and then generates the output message based on the protocol format used by the intended recipient device or system. The output message can be generated based upon a comparison with, and application of, a set of translation rules 2420 that are accessible by the translation module 2415.

The translation rules 2420 can include rules that govern how to handle possible variations between formatting implementations within a common protocol. Examples of variations in formatting implementation of an electronic medical communication protocol include, for example, the delimiter or separator characters that are used to separate data fields, whether a particular field is required or optional, the repeatability of portions of the message (e.g., segments, fields, components, sub-components), the sequence of portions of the message (e.g., the order of fields or components), whether a particular portion of a message is included, the length of the message or portions of the message, and the data type used for the various portions of the message.

In certain embodiments, the translation rules 2420 define additions, deletions, swappings, and/or modifications that should be performed in order to "translate" an input message that adheres to a first HL7 implementation into an output message that adheres to a second HL7 implementation. The output message can have, for example, different formatting than the input message, while maintaining all, or a portion of, the substance or content of the input message.

In addition to translating between different implementations of a common electronic medical communication protocol (e.g., different formatting of HL7 messages), the translation module 2415 can also be configured to translate between input and output messages adhering to different communication protocols. In some embodiments, the translation module 2415 is capable of responding to and translating messages from, for example, one medical communication protocol to a separate medical communication protocol. For example, the translation module 2415 can facilitate communication between messages sent according to the HL7 protocol, the ISO 11073 protocol, other open protocols, and/or proprietary protocols. Accordingly, an input message sent according to the HL7 protocol can be translated to an output message according to a different protocol, or vice-versa.

The operation of the translation module 2415 and the translation rules 2420 will be described in more detail below. Various embodiments of system architectures including the translation module 2415 will now be described.

In certain embodiments, the first medical device 2405, the second medical device 2410, and the translation module 2415 are communicatively coupled via connection to a common communications network. In some embodiments, the translation module 2415 can be communicatively coupled between the first medical device 2405 and the second medical device 2410 (with or without a communications network) such that all messages between the first and second medical devices 2405, 2410 are routed through the translation module 2415. Other architectures are also possible.

The first and second medical devices 2405, 2410 and the translation module 2415 can be included in, for example, a portion of the physiological monitoring system 200 of FIG. 2 or the clinical network environment 600 of FIG. 6 described above. In certain embodiments, the portion of the physiological monitoring system 200 comprises a portion of a messaging sub-system of the physiological monitoring system 200 for supporting the exchange of data between the various clinical computer systems used in the hospital.

In certain embodiments, the translation module 2415 can facilitate communication across multiple networks within a hospital environment. In other embodiments, the translation module 2415 can facilitate communication of messages across one or more networks extending outside of the hospital or clinical network environment. For example, the translation module 2415 can provide a communications interface with banking institutions, insurance providers, government institutions, outside pharmacies, other hospitals, nursing homes, or patient care facilities, doctors' offices, and the like.

In some embodiments, the translation module 2415 of FIG. 24 can be a component of, for example, the patient monitoring system 200 described herein. For example, the translation module 2415 can be communicatively coupled with the hospital network 220 illustrated in FIG. 2. In such embodiments, the translation module 2415 can facilitate the exchange of patient monitoring information, including, for example, physiological parameter measurements, physiological parameter trend information, and physiological parameter alarm conditions between bedside medical monitor devices, nurses' monitoring stations, a Hospital or Clinical Information System (which may store Electronic Medical Records), and/or many other medical devices and systems. The translation module 2415 can enable seamless communication between different medical devices and systems, each of which may use a different implementation of an electronic medical communication protocol such as, for example, the HL7 communication protocol, within a clinical or hospital network environment.

In certain embodiments, the translation module 2415 can also facilitate communication between a first medical device that is part of the patient monitoring sub-system and a second medical device that is not part of, or is external to, the patient monitoring system 200. As such, the translation module 2415 can be capable of responding to externally-generated medical messages (such as patient information update messages, status query messages, and the like from an HIS or CIS) and generating external reporting messages (such as event reporting messages, alarm notification messages, and the like from patient monitors or nurses' monitoring stations).

In another embodiment, first and second medical devices 2405, 2410 communicate with each other over a communication bus 2421. Communication bus 2421 can include any one or more of the communication networks, systems, and methods described above, including the Internet, a hospital WLAN, a LAN, a personal area network, etc. For example, any of the networks describe above with respect to FIGS. 1, 2, 6, 7, 19, etc. can be used to facilitate communication between a plurality of medical devices, including first and second medical devices 2405, 2410, discussed above. One such embodiment is illustrated in FIG. 24B.

Figure 24B:
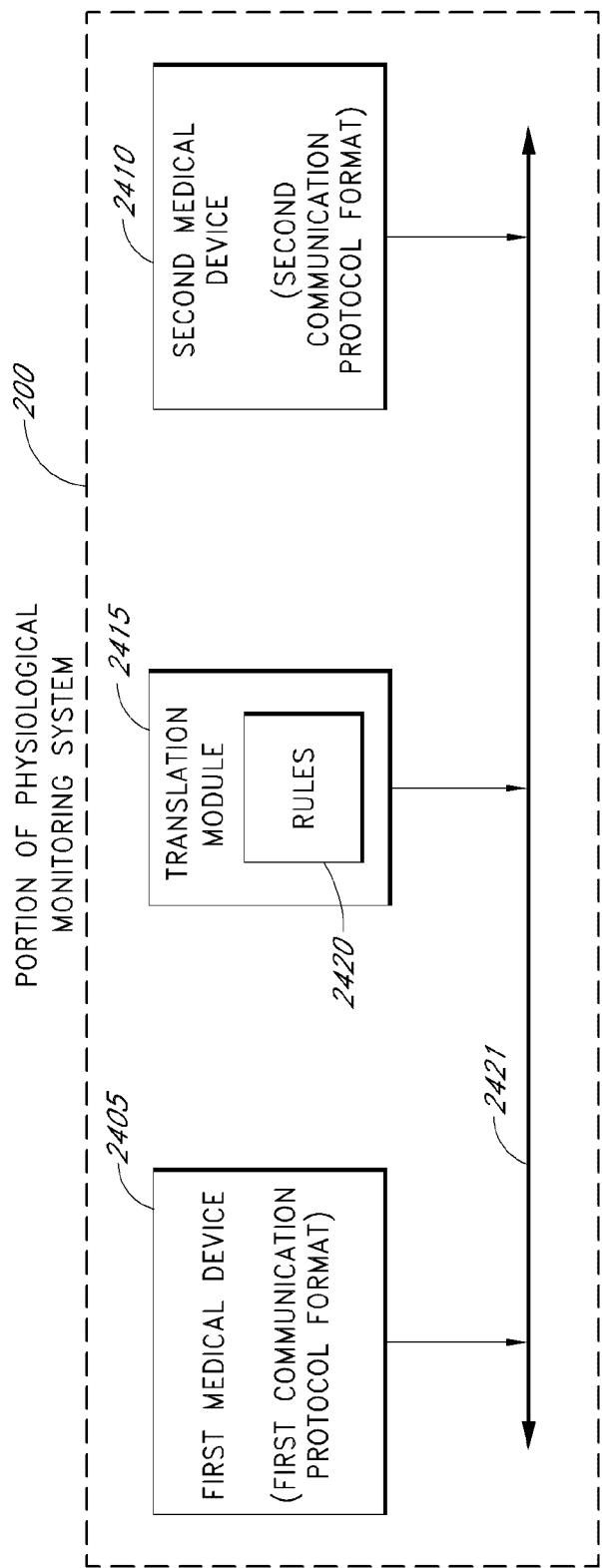
FIG. 24B illustrates a first medical device and a second medical device that communicate with one another via a translation module and a communication bus.

In FIG. 24B, first medical device 2405 provides a message to the communication bus 2421. The message is intended for receipt by the second medical device 2410; however, because first and second medical devices 2405, 2410 communicate according to different communication protocol format, second medical device 2410 is unable to process the message.

Translation module 2415 monitors the communication bus 2421 for such messages. Translation module receives the message and determines that first medical device 2405 is attempting to communicate with second medical device 2410. Translation module 2415 determines that message translation would facilitate communication between first and second medical devices 2405, 2410. Translation module 2415 therefore utilizes an appropriate translation rule stored in a translation module 2420. Translation module 2420 can include a memory, EPROM, RAM, ROM, etc.

The translation module 2415 translates the message from the first medical device 2405 according to any of the methods described herein. Once translated, the translation module 2415 delivers the translated message to the communication bus 2421. The second medical device 2410 receives the translated message and responds appropriately. For example, the second medical device may perform a function and/or attempt to communication with the first medical device 2405. The translation module 2415 facilitates communication from the second medical device 2410 to the first medical device 2405 in a similar manner.

The first medical device 2405 and the second medical device 2410 can be, for example, any of the medical devices or systems communicatively coupled to the hospital network 222 illustrated in FIG. 2. These medical devices or systems can include, for example, point-of-care devices (such as bedside patient monitors), data storage units or patient record databases, hospital or clinical information systems, central monitoring stations (such as a nurses' monitoring station), and/or clinician devices (such as pagers, cell phones, smart phones, personal digital assistants (PDAs), laptops, tablet PCs, personal computers, pods, and the like).

In some embodiments, the first medical device 2405 is a patient monitor for communicatively coupling to a patient for tracking a physiological parameter (e.g., oxygen saturation, pulse rate, blood pressure, etc.), and the second medical device 2410 is a hospital information system ("HIS") or clinical information system ("CIS"). In some embodiments, the patient monitor can communicate physiological parameter measurements, physiological parameter alarms, or other physiological parameter measurement information generated during the monitoring of a patient to the HIS or CIS for inclusion with the patient's electronic medical records maintained by the HIS or CIS.

In some embodiments, the first medical device 2405 is an HIS or CIS and the second medical device 2410 is a nurses' monitoring station, as described herein. However, the translation module 2415 can facilitate communication between a wide variety of medical devices and systems that are used in hospitals or other patient care facilities. For example, the translation module 2415 can facilitate communication between patient physiological parameter monitoring devices, between a monitoring device and a nurses' monitoring station, etc.

Using the translation module 2415, a patient monitoring sub-system, such as those described herein (e.g., physiological monitoring system 200), can push data to the HIS or pull data from the HIS even if the HIS uses a different implementation of the HL7 protocol, or some other electronic medical communication protocol.

In certain embodiments, the patient monitoring sub-system can be configured to push/pull data at predetermined intervals. For example, a patient monitor or clinician monitoring station can download patient data automatically from the HIS at periodic intervals so that the patient data is already available when a patient is connected to a patient monitor. The patient data sent from the HIS can include admit/discharge/transfer ("ADT") information received upon registration of the patient. ADT messages can be initiated by a hospital information system to inform ancillary systems that, for example, a patient has been admitted, discharged, transferred or registered, that patient information has been updated or merged, or that a transfer or discharge has been canceled.

In other embodiments, the patient monitoring sub-system can be configured to push/pull data to/from the HIS only when the HIS is solicited by a query. For example, a clinician may make a request for information stored in a patient's electronic medical records on the HIS.

In still other embodiments, the patient monitoring sub-system can be configured to push/pull data to/from the HIS in response to an unsolicited event. For example, a physiological parameter of a patient being monitored can enter an alarm condition, which can automatically be transmitted to the HIS for storing in the patient's electronic medical records. In yet other embodiments, any combination of the above methods or alternative methods for determining when to communicate messages to and from the HIS can be employed.

Example system architectures and example triggers for the communication of messages involving the translation module 2415 have been described. Turning now to the operation of the translation module, FIGS. 25A-25D illustrate an example medical message at different phases or steps of a translation process. The translation process will be described in more detail below in connection with FIGS. 26, 27A and 27B.

FIG. 25A illustrates an example ADT input message 2505 received by the translation module 2415 from an HIS. The ADT input message 2505 is implemented according to the HL7 communication protocol and contains information related to the admission of a patient to a hospital. The ADT message 2505 includes multiple segments, including a message header segment 2506, an event segment, a patient identification segment, a patient visit segment, role segments, a diagnosis segment, and multiple custom segments.

In some embodiments, the message header ("MSH") segment 2506 defines how the message is being sent, the field delimiters and encoding characters, the message type, the sender and receiver, etc. The first symbol or character after the MSH string can define the field delimiter or separator (in this message, a "caret" symbol). The next four symbols or characters can define the encoding characters. The first symbol defines the component delimiter ("~"), the second symbol defines the repeatable delimiter ("|"), the third symbol defines the escape delimiter ("\"), and the fourth symbol defines the sub-component delimiter ("&"). All of these delimiters can vary between HL7 implementations.

In some embodiments, the example header segment 2506 further includes the sending application ("VAFC PIMS"), the receiving application ("NPTF-508"), the date/time of the message ("20091120104609-0600"), the message type ("ADT~A01"), the message control ID ("58103"), the processing ID ("P"), and the country code ("USA"). As represented by the consecutive caret symbols, the header segment also contains multiple empty fields.

FIG. 25B illustrates the message header segment 2506 after it has been parsed into fields or elements based on an identified field delimiter (the caret symbol). In certain embodiments, the parsed input message comprises an XML message that is configured to be transformed according to extensible stylesheet language transformation (XSLT) rules.

In certain embodiment, the parsed input message can be encoded. FIG. 25C illustrates the parsed message header segment of the input message after being encoded (e.g., using a Unicode Transformation Format-8 ("UTF-8") encoding scheme).

The encoded message header segment shows some of the various data types that can be used in the message. For example, the sending application ("VAFC PIMS") of the third parsed field and the receiving application ("NPTF-508") of the fifth parsed field are represented using a hierarchic designator ("HD") name data type. The date/time field (the seventh parsed field) is represented using the time stamp ("TS") data type. The processing ID field (the eleventh parsed field) is represented using the processing type ("PT") data type. The fields that do not include a data type identifier are represented using the string ("ST") data type. Other possible data types include, for example, coded element, structured numeric, timing quantity, text data, date, entry identifier, coded value, numeric, and sequence identification. The data types used for the various fields or attributes of the segments can vary between formatting implementations.

FIG. 25D illustrates an example output message 2510 from the translation module 2415 based on the example input message 2505 of FIG. 25A. The output message 2510 includes a message acknowledgement segment 2512.

Turning to the operation of the translation module, the translation module 2415 can, for example, create, generate, or produce an output message that is reflective of the input message based on an application of the set of translation rules 2420. In some embodiments, the translation module 2415 can, for example, translate, transform, convert, reformat, configure, change, rearrange, modify, adapt, alter, or adjust the input message based on a comparison with, and application of, the set of translation rules 2420 to form the output message. In some embodiments, the translation module 2415 can, for example, replace or substitute the input message with an output message that retains the content of the input message but has a new formatting implementation based upon a comparison with, and application of, the set of translation rules 2420.

Figure 26:
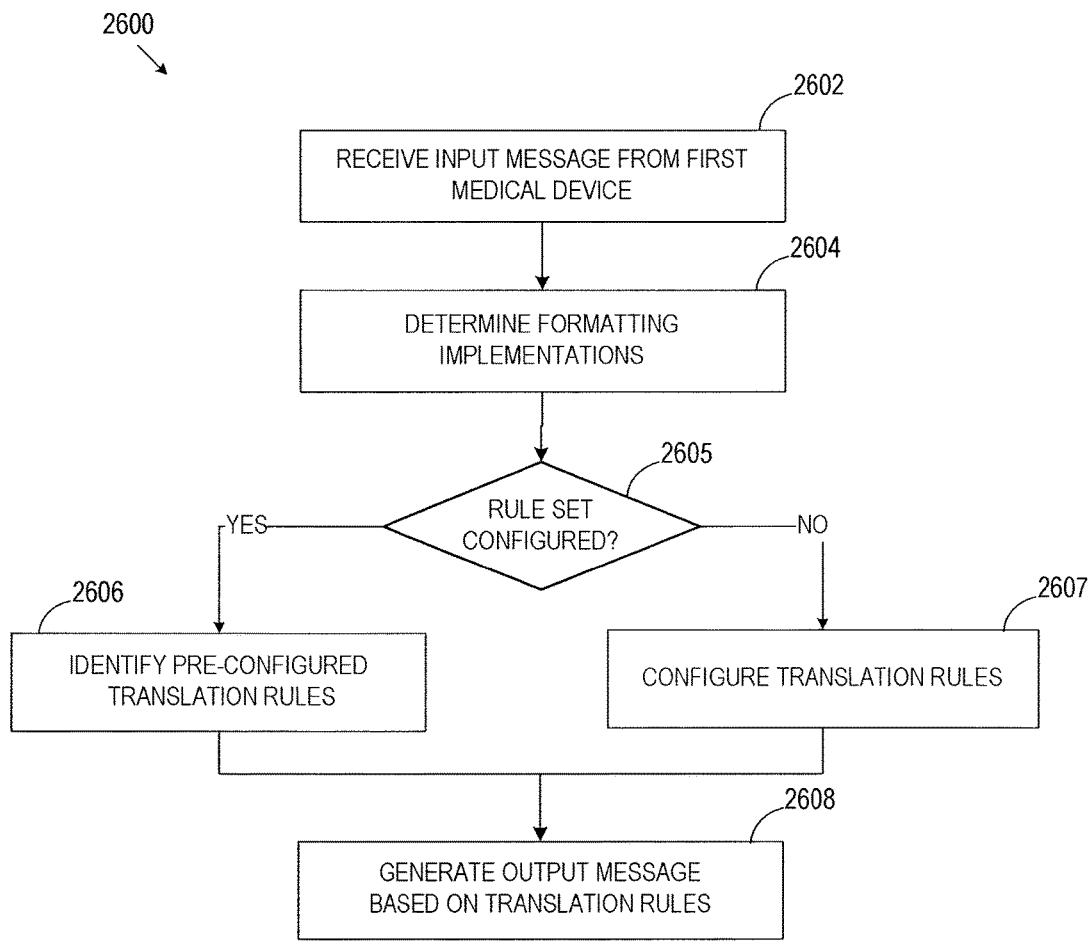
FIG. 26 illustrates a translation process for generating an output message based on an input message and a comparison with translation rules associated with the translation module.

FIG. 26 illustrates a translation process 2600 for generating an output message based on an input message and a comparison with the set of translation rules 2420 associated with the translation module 2415. The translation process 2600 starts at block 2602 where the translation module 2415 receives an input message from a first medical device.

At block 2604, the translation module 2415 determines the formatting implementation of the input message and the formatting implementation to be used for the output message. In certain embodiments, the input message can include one or more identifiers indicative of the formatting implementation. In some embodiments, the determination of the formatting implementation can be made, for example, by analyzing the message itself by identifying the delimiter or encoding characters used, the field order, the repeatability of segments, fields, or components, the data type of the fields, or other implementation variations. In certain embodiments, the translation module 2415 can separate or parse out the formatting from the content of the message (as shown in FIG. 25B) to aid in the determination of the formatting implementation. In some embodiments, the translation module 2415 determines the formatting implementation of the input message by referencing a database that stores the implementation used by each device with which the translation module 2415 has been configured to interface.

In certain embodiments, the determination of the formatting implementation required by the output message can also be determined from the input message. For example, the input message can include a field that identifies the intended recipient application, facility, system, device, and/or destination. The input message can alternatively include a field that identifies the type of message being sent (e.g., ADT message) and the translation module 2415 can determine the appropriate recipient from the type of message being sent and/or the sending application, device, or system. The translation module 2415 can then determine the formatting implementation required by the intended recipient of the input message.

At decision block 2605, the translation module 2415 determines whether a rule set has been configured for the translation from the identified formatting implementation of the input message to the identified formatting implementation to be used for the output message. The rule set may have been manually configured prior to installation of the translation module software or may have been automatically configured prior to receipt of the input message. If a rule set has already been configured, then the translation process 2600 continues to block 2606. If a rule set has not been configured, then a rule set is configured at block 2607. The configuration of the rule set can be performed as described below in connection with FIGS. 28 and 29A-29D. The translation process 2600 then continues to block 2608.

At block 2606, the translation module 2415 identifies the pre-configured rules from the set of translation rules 2420 that govern translation between the determined formatting implementation of the input message and the formatting implementation of the output message. In some embodiments, the identification of the pre-configured rules can be made manually.

At block 2608, the translation module 2415 generates an output message based on the configured rule set(s) of the translation rules 2420. In certain embodiments, the output message retains all, or at least a portion of, the content of the input message but has the format expected and supported by the intended recipient of the input message.

The translation rules 2420 can include, for example, unidirectional rules and/or bidirectional rules. A unidirectional rule is one, for example, that may be applied in the case of a message from a first medical device (e.g., 2405) to a second medical device (e.g., 2410) but is not applied in the case of a message from the second medical device to the first medical device. For example, a unidirectional rule could handle a difference in the delimiters used between fields for two different formatting implementations of, for example, the HL7 communication protocol. The translation module 2415 can apply a field delimiter rule to determine if the field delimiter is supported by the intended recipient of the input message. If the field delimiter of the input message is not supported by the intended recipient, the field delimiter rule can replace the field delimiter of the input message with a field delimiter supported by the intended recipient.

For example, an input message from an input medical device can include a formatting implementation that uses a "caret" symbol ("^") as the field delimiter or separator. However, the formatting implementation recognized by the intended recipient medical device may use a "pipe" symbol ("|") as the field delimiter. The translation module 2415 can identify the field delimiter symbol used in the formatting implementation recognized by the intended recipient medical device from the set of translation rules 2420 and generate an output message based on the input message that uses the pipe field delimiter symbol instead of the caret field delimiter symbol used in the input message. The rule to substitute a pipe symbol for a caret symbol would, in this case, only apply to messages that are sent to a recipient device that recognizes the pipe symbol as a field delimiter. This rule could be accompanied by a complementary rule that indicates that a caret symbol should be substituted for a pipe symbol in the case of a message that is intended for a recipient device that is known to recognize the caret symbol as the field delimiter.

Another unidirectional rule can handle the presence or absence of certain fields between different formatting implementations. For example, an input message from an input medical device can include fields that would not be recognized by the intended recipient medical device. The translation module 2415 can generate an output message that does not include the unrecognized or unsupported fields. In situations where an input message does not include fields expected by the intended recipient medical device, the set of translation rules 2420 can include a rule to insert null entries or empty " " strings in the fields expected by the intended recipient medical device and/or to alert the recipient device of the absence of the expected field. The sender device may also be notified by the translation module 2415 that the recipient device does not support certain portions of the message.

Other unidirectional rules can facilitate, for example, the conversion of one data type to another (for example, string ("ST") to text data ("TX") or structured numeric ("SN") to numeric ("NM")), and the increase or decrease in the length of various portions of the message. Unidirectional rules can also be used to handle variations in repeatability of portions of the message. For example, the translation module 2415 can apply a field repeatability rule to repeated instances of a segment, field, component, or sub-component of the message to determine how many such repeated instances are supported by the recipient device, if any, and deleting or adding any repeated instances if necessary. For example, a phone number field of a patient identification segment can be a repeatable field to allow for entry of home, work, and cell phone numbers.

Bidirectional rules can also be used. Such rules may apply equally to messages between first and second medical devices (e.g., 2405, 2410) regardless of which device is the sender and which is the recipient. A bidirectional rule can be used to handle changes in sequence, for example. In certain implementations, an input message from an input medical device can include a patient name field, or fields, in which a first name component appears before a last name component. However, the intended recipient medical device may be expecting an implementation where the last name component appears before the first name component. Accordingly, the set of translation rules 2420 can include a bidirectional rule to swap the order of the first and last name components when communicating between the two medical devices, or between the two formatting implementations. In general, field order rules can be applied to determine whether the fields, components, or sub-components are in the correct order for the intended recipient and rearranging them if necessary. Other bidirectional rules can be included to handle, for example, other sequential variations between formatting implementations or other types of variations.

The translation rules 2420 can also include compound rules. For example, a compound rule can include an if-then sequence of rules, wherein a rule can depend on the outcome of another rule. Some translation rules 2420 may employ computations and logic (e.g., Boolean logic or fuzzy logic), etc.

Figure 27A:
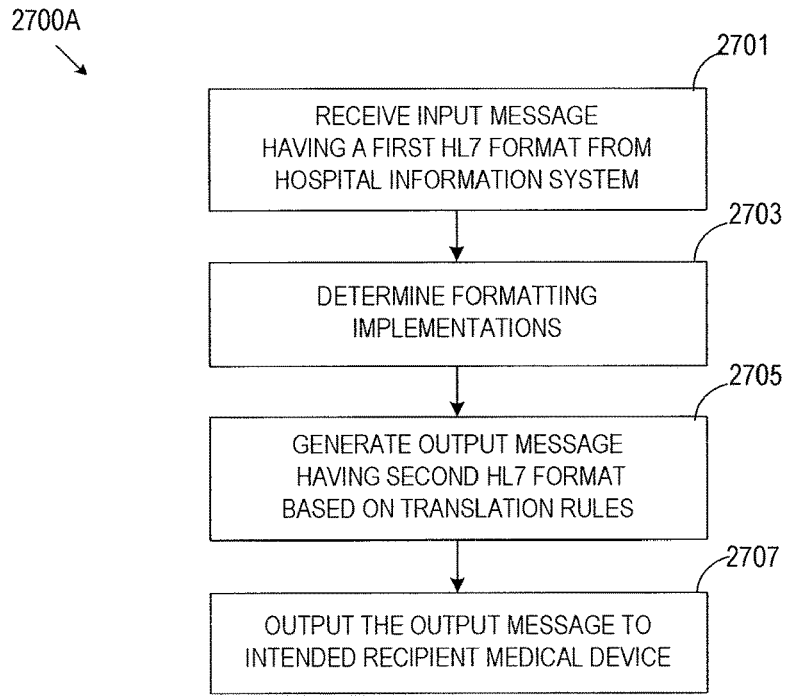
FIG. 27A illustrates a translation process in which the translation module facilitates communication of an HL7 message from a Hospital Information System ("HIS") having a first HL7 format to an intended recipient medical device having a second HL7 format.
Figure 27B:
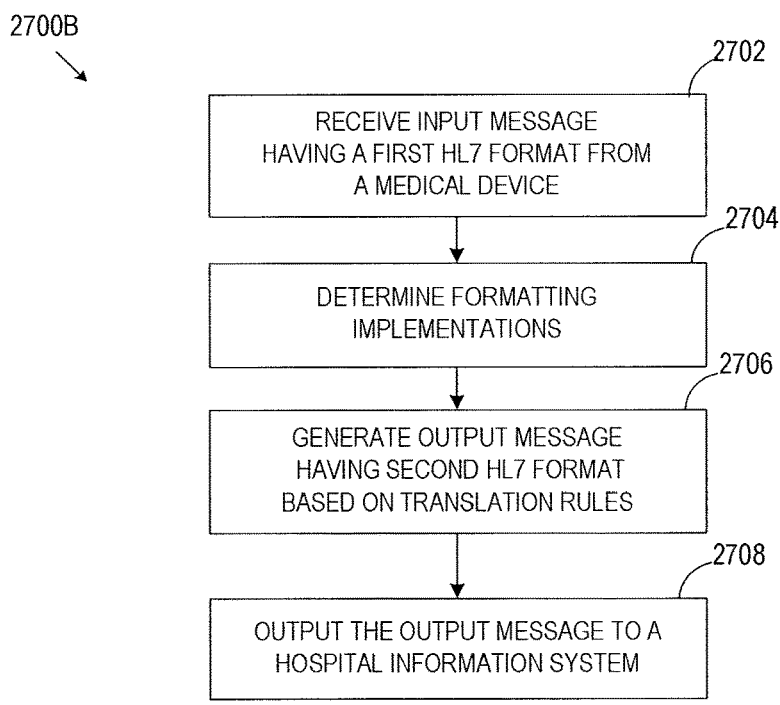
FIG. 27B illustrates a translation process in which the translation module facilitates communication of an HL7 message from a medical device having a first HL7 format to a HIS having a second HL7 format.

As discussed above, the messages communicated over the hospital-based communication network can employ the HL7 protocol. FIGS. 27A and 27B illustrate translation processes 2700A, 2700B in which HL7 messages are communicated between a HIS and a medical device over a hospital-based communications network or a clinical network. The translation processes 2700A, 2700B will be described with the assumption that the rules governing "translation" between the first and second HL7 formats have already been configured.

FIG. 27A illustrates a translation process 2700A in which the translation module 2415 facilitates communication of an HL7 message, such as the ADT message of FIG. 25A, from an HIS having a first HL7 format to an intended recipient medical device, such as a patient monitor or a clinician monitoring station, having a second HL7 format.

The translation process 2700A starts at block 2701, where the translation module 2415 receives an input message having a first HL7 format from the HIS. In certain embodiments, the input message includes information regarding, for example, the admission of a patient and/or patient identification and patient medical history information from an electronic medical records database.

At block 2703, the translation module 2415 determines the formatting implementation of the input message and the formatting implementation to be used for the output message. These determinations can be made in a similar manner to the determinations discussed above in connection with block 2604 of FIG. 26.

At block 2705, the translation module 2415 identifies the rules that govern translation between the determined HL7 format of the input message and the HL7 format of the output message and generates an output message having the second HL7 format based on the identified rules. In certain embodiments, the output message retains the content of the input message sent by the HIS but has the format expected and supported by the intended recipient of the input message.

At block 2707, the translation module 2415 can output the output message to the intended recipient over the hospital-based communications network. In certain embodiments, the intended recipient can transmit an acknowledgement message back to the hospital information system acknowledging successful receipt or reporting that an error occurred.

FIG. 27B illustrates a translation process 2700B in which the translation module 2415 facilitates communication of an HL7 message from a medical device, such as a patient monitor, having a first HL7 format to an HIS having a second HL7 format. For example, the patient monitor can transmit reporting event data m such as patient alarm data, to the HIS to store in the patient's electronic medical records.

The translation process 2700B starts at block 2702, where the translation module 2415 receives an input message having a first HL7 format from the medical device. In certain embodiments, the input message includes patient monitoring data or alarm data regarding one or more physiological parameters of the patient being monitored for storage in an electronic medical records database associated with the HIS.

At block 2704, the translation module 2415 determines the formatting implementation of the input message and the formatting implementation to be used for the output message. These determinations can be made in a similar manner to the determinations discussed above in connection with block 2604 of FIG. 26.

At block 2706, the translation module 2415 identifies the rules that govern translation between the determined HL7 format of the input message and the HL7 format of the output message and generates an output message having the second HL7 format based on the identified rules. In certain embodiments, the output message retains the content of the input message sent by the medical device but has the format expected and supported by the HIS.

At block 2708, the translation module 2415 can output the output message to the hospital information system over the hospital-based communications network. In certain embodiments, the HIS can transmit an acknowledgement message back to the medical device acknowledging successful receipt or reporting that an error occurred.

FIGS. 26, 27A and 27B described the operation of the translator module 2415. FIGS. 28 and 29A-29D will be used to illustrate the description of the configuration of the translation rules 2420.

The translation rules 2420 can be implemented as one or more stylesheets, hierarchical relationship data structures, tables, lists, other data structures, combinations of the same, and/or the like. In certain embodiments, the translation rules 2420 can be stored in local memory within the translation module 2415. In other embodiments, the translation rules 2420 can be stored in external memory or on a data storage device communicatively coupled to the translation module 2415.

The translation module 2415 can include a single rule set or multiple rule sets. For example, the translation module 2415 can include a separate rule set for each medical device/system and/or for each possible communication pair of medical devices/systems coupled to the network or capable of being coupled to the network. In some embodiments, the translation module 2415 can include a separate rule set for each possible pair of formatting implementations that are allowed under a medical communication protocol such as, for example, the HL7 protocol.

Figure 28:
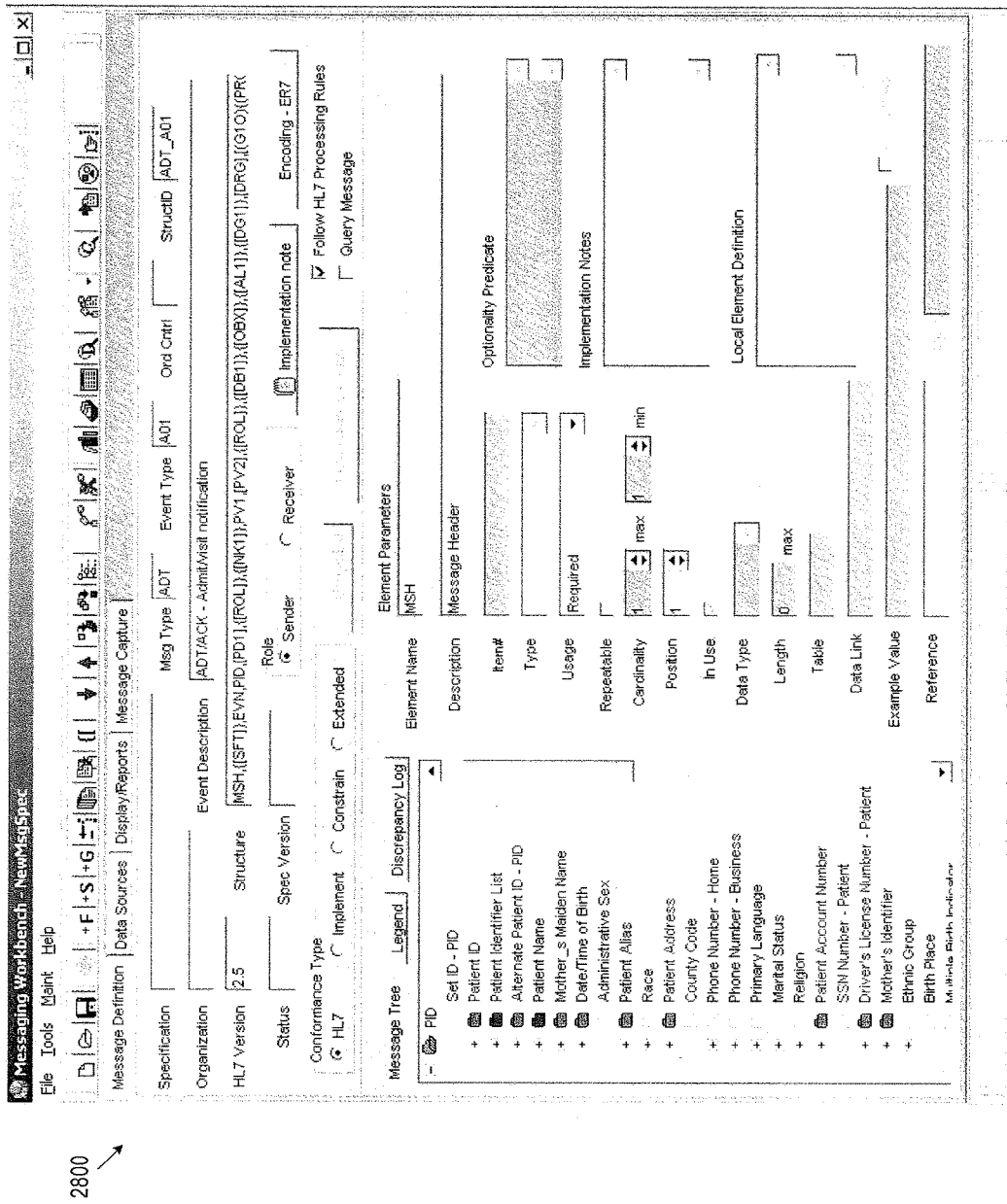
FIG. 28 illustrates an example screenshot from a messaging implementation software tool for manually configuring translation rules to be used by the translation module.

In certain embodiments, the translation rules 2420 can be manually inputted using, for example, the messaging implementation software tool 2800 illustrated in FIG. 28. For example, the software developer for a particular hospital network can determine the protocol message formats used by the devices and/or systems that are or can be coupled to the hospital network and then manually input rules to facilitate "translation" between the various protocol message formats supported or recognized by the devices and/or systems.

FIG. 28 illustrates an example screenshot from a messaging implementation software tool 2800 for manually configuring translation rules 2420 to be used by the translation module 2415. The screenshot from the messaging implementation software tool 2800 illustrates various parameters that may differ between formatting implementations of an electronic medical communication protocol, such as HL7. The screenshot also includes areas where a user can input information that defines, or is used to define, translation rules for converting between different HL7 implementations. In some embodiments, the messaging implementation software tool 2800 stores a variety of pre-configured rule sets based, for example, on known communication protocol implementations of various medical devices. In such embodiments, a user may configure one or more translation rules 2420 to be used in communications involving such devices by entering identification information, such as the device manufacturer, model number, etc. Based on this identification information, the messaging implementation tool 2800 can identify a pre-configured set of translation rules for communication with that device.

In other embodiments, the translation rules 2420 can be automatically generated. For example, the automatic generation of a new set, or multiple sets, of rules can be triggered by the detection of a newly recognized "communicating" medical device or system on a network. In certain embodiments, the automatic generation of a new set or multiple sets of rules can occur at the time a first message is received from or sent to a new "communicating" medical device or system coupled to the network. In still other embodiments, the automatic generation of rule sets includes updating or dynamically modifying a pre-existing set of rules.

The automatic generation of translation rule sets can be carried out in a variety of ways. For example, in some embodiments, the translation module 2415 can automatically initiate usage of a pre-configured set of translation rules 2420 based upon, for example, the make and model of a new device that is recognized on the network. In certain embodiments, the translation module 2415 can request one or more messages from the new device or system and then analyze the messages to determine the type of formatting being implemented, as illustrated by the automatic rule configuration process 2900A of FIG. 29A. The automatic rule configuration process 2900A starts at block 2901, where the translation module 2415 receives one or more messages from a detected medical device or system on the network. The messages can be received upon transmission to an intended recipient medical device or system or in response to a query sent by the translation module 2415 or another medical device or system coupled to the network.

At block 2903, the translation module 2415 determines the protocol of the one or more received messages by, for example, analyzing the message or by consulting a database that indicates what communication protocol/format is implemented by each medical device or system on the network. In certain embodiments, the translation module 2415 is configured to handle medical messages implemented using a single common protocol, such as HL7. Accordingly, if a determination is made that the received messages are implemented using a non-supported or non-recognized protocol, the translation module can ignore the messages received from the detected medical device or system, output an alert or warning, or allow the messages to be sent without being translated.

At block 2905, the translation module 2415 determines the formatting implementation of the received message(s). In certain embodiments, the received messages can include one or more identifiers indicative of the formatting implementation. In other embodiments, the determination of the formatting implementation can be made, for example, by analyzing the message itself by checking field order, the delimiter or encoding characters used, or other implementation variations. In certain embodiments, the translation module 2415 can separate or parse out the formatting from the content of the message to aid in the determination of the formatting implementation.

At block 2907, the translation module 2415 configures one or more rules or rule sets to handle messages received from and/or sent to the detected medical device or system. In certain embodiments, the configuration of the rules involves the creation or generation of new rules. In other embodiments, the configuration of the rules involves the alteration or updating of existing rules. The configured rules or rule sets can be included with the translation rules 2420. If a set of rules already exists for the formatting implementation used by the new device or system, then the configuration of new translation rules may not be required. Instead, existing translation rules can be associated with the new device or system for use in communication involving that device or system. In other embodiments, the translation module 2415 can create a new set of rules geared specifically for the new device or system or can modify an existing set of rules based on subtle formatting variations identified.

In other embodiments, the translation module 2415 can generate test message(s) that may be useful in identifying the communication protocol and implementation used by a device or system. For example, the translation module can generate test messages to cause the newly detected device or system to take a particular action (e.g., store information) and then query information regarding the action taken by the newly detected device to determine whether or how the test message was understood. This is illustrated by the automatic rule configuration process 2900B of FIG. 29B.

The automatic rule configuration process 2900B starts at block 2902, where the translation module 2415 transmits one or more test, or initialization, messages to a remote device or system detected on a network. The test messages can be configured, for example, to instruct the remote device or system to take a particular action (e.g., store patient information). In certain embodiments, the test messages can be configured to generate a response indicative of the type of formatting recognized or supported by the remote device or system. In other embodiments, the test messages can be configured such that only devices or systems supporting a particular formatting implementation will understand and properly act on the test messages.

At block 2904, the translation module 2415 queries the remote device or system to receive information regarding the action taken based on the test message sent to the remote device or system to determine whether the test message was understood. For example, if the test message instructed the remote device or system to store patient information in a particular location, the translation module 2415 can query the information from the location to determine whether the test message was understood. If the test message was not understood, the translation module 2415 can, for example, continue sending test messages of known formatting implementations until a determination is made that the test message has been understood.

At block 2906, the translation module 2415 determines the protocol and formatting implementation based on the information received. As an example, in certain embodiments, the test message can include an instruction to store patient name information. The test message can include a patient name field having a first name component followed by a surname component. The translation module 2415 can then query the remote device or system to return the patient surname. Depending on whether the patient surname or the first name is returned, this query can be useful in determining information about the order of fields in the formatting implementation being used by the remote device or system. As another example, the test messages can instruct the detected device or system to store repeated instances of a component. The translation module 2415 can then query the device or system to return the repeated instances to see which, if any, were stored. This repeatability information can also be useful in determining whether certain fields are allowed to be repeated in the formatting implementation being used by the remote device for system, and, if so, how many repeated instances are permitted.

At block 2908, the translation module 2415 configures one or more rules to handle messages received from and/or sent to the detected medical device or system. For example, the rules can convert messages from the message format used by a first medical device to that used by a second medical device, as described herein. In certain embodiments, the configuration of the rules involves the creation or generation of new rules. In other embodiments, the configuration of the rules involves the alteration or updating of existing rules. If a set of rules already exists for the formatting implementation used by the new device or system, then the configuration of new translation rules may not be required. Instead, existing translation rules can be associated with the new device or system for use in communication involving that device or system.

Figure 29A:
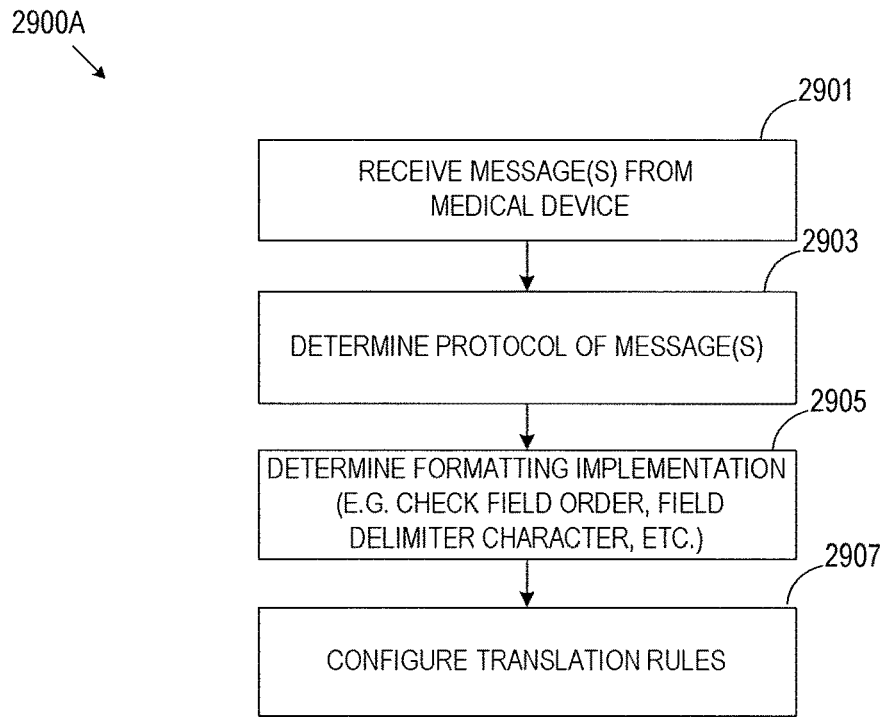
FIGS. 29A and 29B illustrate automatic rule configuration processes performed by the translation module.
Figure 29B:
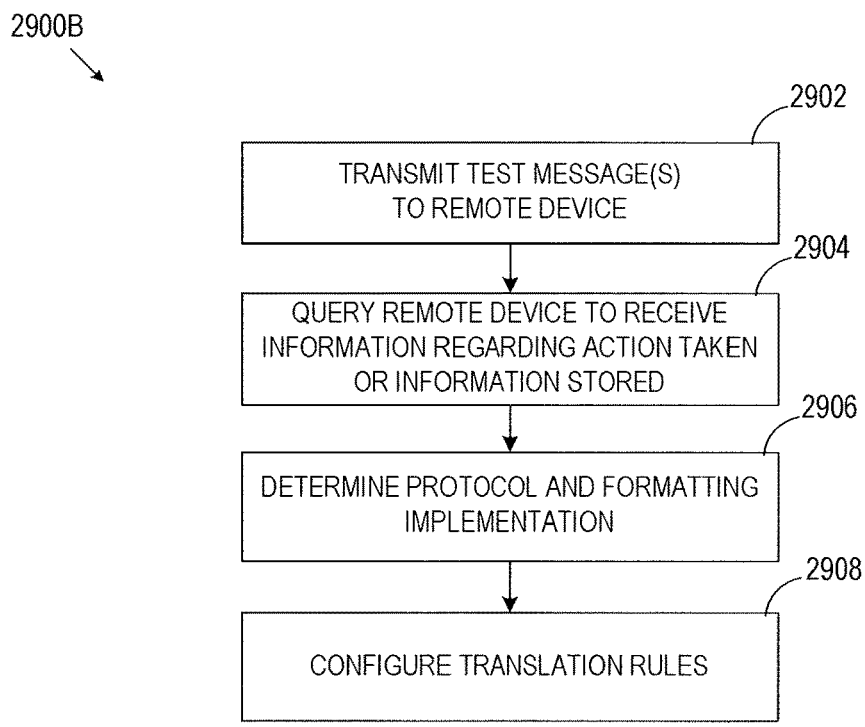
Figure 29C:
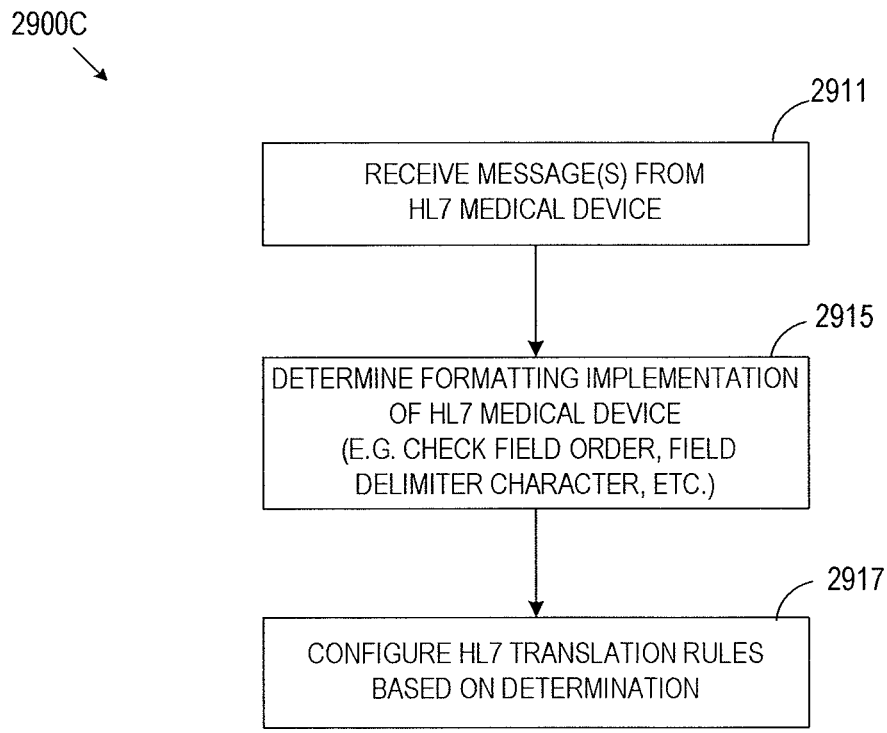
FIGS. 29C and 29D illustrate automatic rule configuration processes performed by the translation module for messages utilizing the HL7 protocol.
Figure 29D:
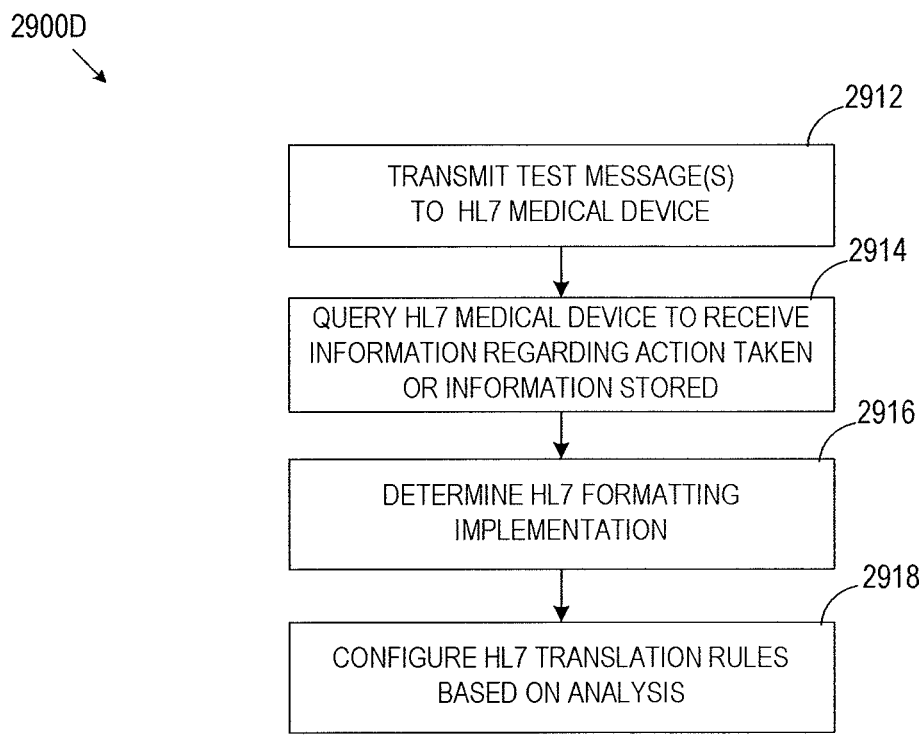

FIGS. 29C and 29D illustrate automatic rule configuration processes performed by the translation module 2415 for messages utilizing the HL7 protocol. The HL7 protocol can be used, for example, to communicate electronic messages to support administrative, logistical, financial, and clinical processes. For example, HL7 messages can include patient administration messages, such as ADT messages, used to exchange patient demographic and visit information across various healthcare systems.

The automatic rule configuration process 2900C illustrated in FIG. 29C is similar to the process 2900A illustrated in FIG. 29A. At block 2911, the translation module 2415 receives one or more messages from an HL7 medical device. At block 2915, the translation module 2415 determines the formatting implementation of the HL7 medical device from the one or more messages received. As discussed above, the determination of the formatting implementation can be made, for example, by checking field order or sequence, field delimiter characters, repeatability, cardinality, and other HL7 implementation variations.

At block 2917, the translation module 2415 configures one or more rules to handle messages received from and/or sent to the HL7 medical device. In certain embodiments, the configuration of the rules involves the creation or generation of new rules for the detected formatting implementation. In other embodiments, the configuration of the rules involves the dynamic alteration or updating of existing rules. If a set of rules already exists for the formatting implementation used by the new HL7 medical device, then the configuration of new translation rules may not be required. Instead, existing translation rules can be associated with the new HL7 medical device for use in communication involving that device.

The automatic rule configuration process 2900D illustrated in FIG. 29D is similar to the process 2900B illustrated in FIG. 29B. At block 2912, the translation module 2415 transmits one or more test, dummy, or initialization messages to an HL7 medical device. In other embodiments, the translation module 2415 can cause one or more test messages to be transmitted to the new HL7 medical device from another HL7 medical device. As described above, the test messages can include messages having known HL7 formats configured to determine whether the HL7 device understands the test messages. The test messages can include test ADT messages, for example.

At block 2914, the translation module 2415 queries the HL7 medical device to receive information regarding an action taken or information stored in response to the test message. At block 2916, the translation module 2415 determines the formatting implementation of the HL7 device based on the information received. In certain embodiments, the translation module 2415 can analyze the information received to determine whether the test message or messages were properly understood. If none of the test messages were properly understood, the translation module 2415 can send additional test messages having other known HL7 formats and repeat blocks 2914 and 2916.

At block 2918, the translation module 2415 configures one or more translation rules to handle messages received from and/or sent to the detected HL7 medical device. In certain embodiments, the configuration of the translation rules involves the creation or generation of new translation rules. In other embodiments, the configuration of the rules involves the alteration or updating of existing rules. If a set of translation rules already exists for the formatting implementation used by the new HL7 medical device, then the configuration of new translation rules may not be required. Instead, existing translation rules can be associated with the new HL7 medical device for use in communication involving that HL7 medical device.

The automatic rule configuration processes described above can be triggered by the detection of a network device or system by the translation module 2415. The medical devices referred to in FIGS. 29A-29D can include any of the devices or systems illustrated in FIG. 2 and discussed above.

In some embodiments, the automatic generation of translation rules can advantageously occur post-installation and post-compilation of the messaging sub-system software, which includes the translation module 2415. In certain embodiments, the automatic generation or dynamic modification of the translation rules 2420 can occur without having to recompile or rebuild the translation module software. This feature can be advantageous in terms of efficiently complying with U.S. Food and Drug Administration ("FDA") requirements regarding validation of software used in healthcare environments.

Take, for example, a situation where a medical device manufacturer plans to use the translation module 2415 to facilitate communication between a particular medical device or system that is to be installed in a hospital (e.g., a patient monitoring system, as described herein), or other patient care facility, and other devices or systems that are already installed at the hospital (e.g., the HIS or CIS). Any software required for the operation of the new medical device to be installed may be at least partially validated for FDA compliance prior to installation at the hospital despite the fact that, for example, the HL7 implementations of other existing devices or systems at the hospital may still be unknown. For example, any aspects of the software for the new medical device that are dependent upon receiving messages from other hospital devices can be validated pre-installation as being capable of fully and correctly operating when the expected message format is received. Then, once the medical device is installed at the hospital, the validation of the software can be completed by showing that the translation module 2415 is able to provide messages of the expected format to the newly installed device. In this way, FDA validation tasks can be apportioned to a greater extent to the pre-installation timeframe where they can be more easily carried out in a controlled manner rather than in the field.

In addition, the translation module 2415 can further help streamline FDA validation, for example, when a medical device or system is expected to be installed at different hospitals whose existing devices use, for example, different implementations of the HL7 protocol. Normally, this type of situation could impose the requirement that the entire functionality of the software for the new medical device be completely validated at each hospital. However, if the translation module 2415 is used to interface between the new medical device and the hospital's existing devices, then much of the software functionality could possibly be validated a single time prior to installation, as just described. Then, once installed at each hospital, the software validation for the medical device can be completed by validating that correct message formats are received from the translation module (the translation rules for which are field-customizable). This may result in making on-site validation procedures significantly more efficient, which will advantageously enable more efficient FDA compliance in order to bring life-saving medical technology to patients more quickly by the use of field-customizable translation rules.

Patient Monitoring Reports

Devices and methods for monitoring physiological parameters such as blood oxygen saturation, pulse rate, blood pressure, and many others, are described herein. Such medical monitoring devices are often programmed with alarm limits to automatically detect when a physiological parameter has a value that is, for example, outside the range of values considered safe or healthy for that particular physiological parameter. In some embodiments, when such an alarm condition is detected, various actions can be taken. For example, the bedside medical monitor can emit an audible or visual alarm. In addition, in some cases, after the alarm condition has persisted for some set amount of time (e.g., 5 sec.), the alarm condition can be displayed at, for example, a central patient monitoring station, as described herein. Moreover, if the alarm condition continues to persist for some set amount of time (e.g., 10 sec.), the clinician assigned to care for the patient who is experiencing the alarm condition can be notified by, for example, a pager or other notification device.

The number of detected alarm conditions is, of course, dependent upon the settings for the alarm criteria that indicate an alarm condition. In some embodiments, such alarm criteria can include a threshold value, which may indicate the boundary between values for a physiological parameter that are considered safe or normal, and those that are considered to indicate a medical condition which may require attention from a clinician. The nearer such an alarm threshold is set to values that are common for that particular physiological parameter in healthy individuals under normal circumstances, the larger the number of alarm events that will be expected to be detected. Generally speaking, the closer the alarm criteria come to being satisfied by the normal expected range of values for a given physiological parameter, then the greater the odds of detecting any deviation from the normal range of values that may indicate that the patient is in need of some type of medical intervention (e.g., administration of drugs, CPR, ventilator, etc.). This can be desirable in the sense that it becomes less likely that a patient will experience medical duress without triggering an alarm, which can be referred to as a false negative.

Reduction of false negatives does not come without a cost, however. Namely, alarm criteria for physiological parameters that are successful in reducing false negatives may also increase the rate of false positives, where alarm conditions are detected even though the patient may not be experiencing any clinically significant medical duress. If false positives become too frequent, they can become burdensome to clinicians, who are responsible for investigating alarm conditions, resetting the monitoring devices from the alarm state, etc. In addition, frequent false positives can even put patients at risk by reducing the importance assigned to alarm events by clinicians, whether consciously or subconsciously. Thus, it is desirable to determine alarm criteria for medical monitoring applications that strike a satisfactory balance that limits false negatives to an acceptable rate without unduly increasing false positive alarm events. In some cases, false positives may be preferred to false negatives, especially in circumstances where the consequences of a false negative would be severe to the patient. Such a preference for maintaining the occurrence of false negatives at a relatively low rate can be reflected in the choice of alarm limit criteria. It is not necessarily the case, however, that false positives are always preferred to false negatives. Moreover, alarm criteria that may be satisfactory for one type of patient may be unsatisfactory for other types of patients. The appropriate balance between false positives and false negatives may vary for different medical monitoring applications.

For example, in the case of blood oxygen saturation monitoring, typical SpO2 values of healthy individuals may fall in the range of 95-100%. Therefore, if a patient monitoring device were configured with an SpO2 alarm threshold of 94%, the number of false positive alarm events may be relatively high. In contrast, if the SpO2 alarm threshold were set at 92%, then the number of false positives would likely be reduced, but the number of false negatives may increase beyond a satisfactory level in some medical monitoring applications. Therefore, devices and methods for providing data that would aid in the selection of an alarm threshold that would reduce false positives while still maintaining false negatives at or below a satisfactory level would be very useful. Such devices and methods could be used for establishing alarm criteria for a wide variety of physiological parameters.

Figure 30:
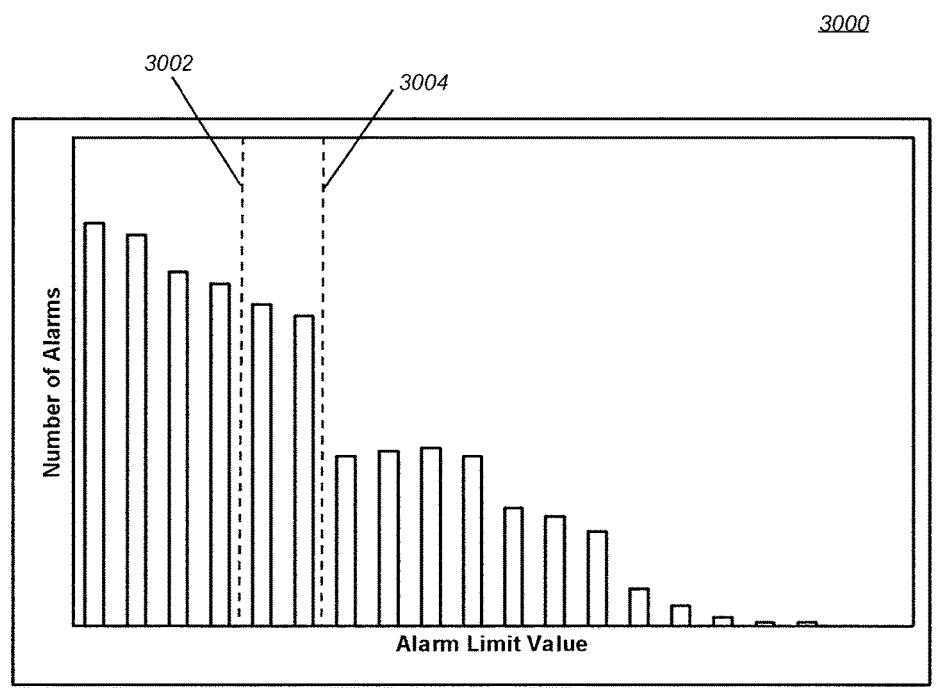
FIG. 30 is an example graph of the distribution of alarm events for a given physiological parameter as a function of alarm limit values.

FIG. 30 is an example graph 3000 of the distribution of alarm events for a given physiological parameter as a function of alarm limit values. The graph 3000 plots the number of detected alarm conditions versus a range of alarm limit values. The graph 3000 reflects, for example, a hypothetical situation where physiological parameter alarm data is collected from a statistically-significant number of patients of a particular type (e.g., cardiac patients) over the course of a statistically-significant period of time using a range of different alarm limit values. Of course, the distribution of alarm events as a function of alarm limit values will generally vary for different physiological parameters.

The graph 3000 shows a set of linearly increasing alarm limit values on the x-axis. The corresponding number of detected alarm conditions for each alarm limit value is plotted on the y-axis. As illustrated, for this particular physiological parameter, the number of detected alarm conditions generally decreases as the alarm limit value is increased. Each bar in the graph 3000 may be representative of, for example, a combination of false positive alarm events and correctly detected alarm events (e.g., detection of an alarm event when the patient was actually in need of medical assistance).

The dashed vertical line 3002 represents one possible alarm limit threshold value. When the physiological parameter value is above the threshold indicated by the dashed vertical line 3002, for example, an alarm condition is detected, whereas when the physiological parameter value is below the threshold, no alarm condition is detected. The dashed vertical line 3004 represents another possible alarm limit value.

As shown on the graph 3000, the illustrated alarm limit values 3002, 3004 are only separated by two values on the x-axis. However, the number of alarms detected using each of the two illustrated alarm thresholds 3002, 3004 is approximately halved in going from the first alarm threshold 3002 to the second alarm threshold 3004. Thus, in this case, the number of alarm thresholds is non-linearly related to variation in the alarm limit values. This is illustrative of the realization that, in some cases, a hospital or other patient care facility could make relatively small changes to the alarm criteria used in monitoring a physiological parameter while disparately impacting the number of detected alarms and false positives. In some cases, the number of detected alarms could be significantly reduced, for example, by reducing the number of false positives without necessarily increasing the risk of false negatives in a clinically-significant way. Even if, however, no disproportionate change in the number of false positives can be achieved with a relatively small adjustment to alarm criteria (e.g., an alarm threshold value), the techniques described herein may still be useful in some circumstances for incrementally reducing the number of false positives in a safe manner. Of course, changes to the alarm criteria used for monitoring patients are not to be taken lightly; generally speaking, hospital administrators or other responsible personnel should authorize any changes to alarm criteria.

In some embodiments, a device and/or system is provided for collecting medical monitoring information from patients in a patient care domain. For example, the medical monitoring information can be collected from a clinically-significant number of patients over a clinically-significant period of time. In some embodiments, the patient care domain is a group of patients of a similar type, or a group of patients who exhibit similar medical characteristics, conditions, defects, etc., and, as such, can also be expected to undergo monitoring alarm conditions for similar reasons. For example, the patient care domain could consist of a group of cardiac patients on a hospital floor, etc.

In some embodiments, a number of bedside patient monitors are used to collect physiological signals from the patients. The raw physiological signals can be processed by the bedside patient monitors. For example, the bedside patient monitors may perform averaging of the raw signals, filtering, etc. The bedside patient monitors may also perform computations to calculate the value of a physiological parameter. The bedside patient monitors may then output an indication of a physiological parameter value (e.g., SpO2, pulse rate, blood pressure, etc.) and its trending over time. Physiological information such as the raw physiological signals, processed physiological signals, and/or calculated physiological parameter values, for example, for each of the patients can then be transmitted to, and stored by, for example, a central repository. In some embodiments, this information is stored by a networked database such as, for example, the round-robin database 722 described herein. In some embodiments, the central repository can store medical monitoring information for the patients in a particular domain (e.g., a hospital ward) over a period of time such as a week, or a month, for example.

At the initial time of monitoring, an algorithm, or algorithms, may be applied to the raw physiological signals, processed physiological signals, and/or computed physiological parameter values for detecting whether a first set of alarm criteria are satisfied. This can be done by, for example, each bedside patient monitor for each patient in the patient care domain. The first set of alarm criteria are, for example, those criteria implemented in the patient monitoring devices that perform real-time monitoring functions to detect alarm conditions. If the alarm criteria are satisfied, then an alarm can be generated, as described herein. The central repository can also be used to store the occurrences of alarm conditions for each patient.

In some embodiments, once a statistically-significant amount of patient monitoring data has been collected at the central repository, a reporting module can access the central repository and use these data to simulate the alarm events that would have been detected had the patient monitoring devices in the patient care domain used a different set of alarm criteria than those that were actually used at the time of monitoring.

In some embodiments, the reporting module is used in conjunction with the patient monitoring systems described herein (e.g., those shown in FIGS. 1, 2, 6, 7, 19, and others). In some embodiments, the reporting module is a server or other computing device communicatively coupled to a network of bedside patient monitoring devices, a central monitoring station, a database, and other devices that can form a patient monitoring system. The reporting module can include a processor for analyzing patient monitoring data. The reporting module can also include, for example, electronic memory for storing patient monitoring data.

In some embodiments, if the central repository includes, for example, physiological parameter trend data for each of the patients, then the reporting module can access the trend data and can re-analyze it using, for example, the same algorithm, or algorithms, previously used by the bedside patient monitoring devices for detecting whether alarm criteria are satisfied. However, in this case a second alarm criteria can be used that is different from the first alarm criteria that was used to detect alarm conditions, for example, in real time when the patient monitoring data was actually collected. In some embodiments, the reporting module re-analyzes the stored patient monitoring data using multiple different new alarm criteria. Thus, the reporting module can generate information showing how the number of alarms detected changes as a function of changing alarm criteria.

Figure 31:
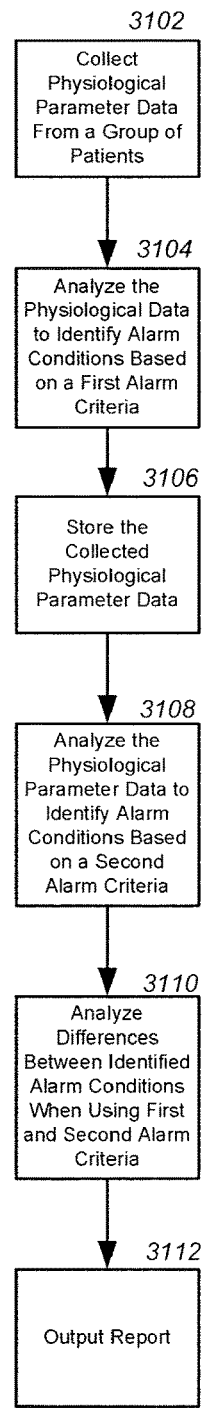
FIG. 31 is a flow chart that illustrates a method for determining the variation in identified alarm conditions resulting from varying alarm criteria.

FIG. 31 is a flow chart that illustrates a method 3100 for determining the variation in identified alarm conditions resulting from varying alarm criteria. The method 3100 begins at block 3102 where physiological parameter data is collected from a group of patients in a patient care domain. For example, the physiological parameter data can be collected by a number of different bedside patient monitoring devices distributed throughout a patient care facility. The collected physiological parameter data can include, for example, any type of information relevant to the physiological parameter being monitored and the patient from whom the physiological parameter data is being collected. Again, some examples of physiological parameter data that can be collected are raw physiological signals, processed physiological signals, calculated values of a physiological parameter, etc.

At block 3104, the physiological parameter data is analyzed to identify alarm conditions based upon a first set of alarm criteria. The alarm criteria can be configurable so as to modify the physiological conditions that will trigger an alarm. In some embodiments, the analysis of the physiological parameter data is performed in substantially real-time by, for example, the bedside patient monitoring devices in order to detect alarm conditions as they occur. The alarm criteria will generally depend upon the particular physiological parameter being monitored. In some embodiments, the alarm criteria is a single threshold value. In some embodiments, the alarm criteria includes multiple threshold values that define, for example, an enclosed range of safe or normal values for the physiological parameter. Other types of alarm criteria can also be used.

At block 3106, the physiological parameter data is stored at, for example, a central repository (e.g., the round-robin database 722). In some embodiments, the central repository stores all, or substantially all, of the physiological parameter data that was collected at block 3102. For example, the central repository can store a physiological information such as the raw physiological signals from each patient, or physiological signals that have already been processed or altered to some extent by, for example, the bedside patient monitoring devices. In addition, the central repository can store information about any alarm conditions that were detected for each patient at block 3104. For example, the central repository can store the timing and type of each alarm condition for each patient.

At block 3108, the physiological parameter data that was previously stored can be analyzed to identify alarm conditions based on a second alarm criteria that is different from the first criteria used at block 3104. This analysis can be performed by, for example, the reporting module described herein. If, for example, in the case of blood oxygen saturation monitoring, detected pulse oximetry signals were analyzed at the actual time of monitoring using an alarm threshold of 94% oxygen saturation, then later at block 3108, the pulse oximetry signals can be re-analyzed using an alarm threshold of 93% oxygen saturation, or 92% oxygen saturation, etc. This analysis of the previously-collected physiological parameter data can be used to simulate the effect of a new alarm threshold in a riskless manner, since patients can still be monitored at, for example, blocks 3102, 3104 using alarm criteria that are already accepted and validated. This ability to simulate the effect of changing alarm criteria on the alarm conditions that are identified from physiological data is advantageous to hospitals and other patient care facilities as a means of adjusting alarm criteria to be specifically adapted for that particular hospital or patient care facility. Specially adapted alarm criteria are advantageous because alarm criteria that work well at one hospital, or for one type of patient, are not necessarily guaranteed to work well at another hospital, or for another type of patient. This can be due to differences in the type of monitoring equipment that is used, differences in patient population, differences in the type of medical care offered, differences in medical procedures implemented by clinicians, etc.

In some embodiments, the algorithm, or algorithms, that are applied by the reporting module to the collected physiological parameter data at block 3108 are the same as, or substantially similar to, those which were applied at the time of monitoring in order to detect real-time alarm conditions, though this may not be required in all embodiments. In addition, in some embodiments, the physiological parameter data stored at the central repository is the same as, or substantially similar to, the physiological parameter data to which alarm detection algorithms were applied by, for example, bedside patient monitors at the time of collection of the data. In this way, different alarm criteria can be simulated as if they had actually been used at the time of collection of the physiological parameter data to detect real-time alarm conditions.

At block 3110, the reporting module can analyze the effect of the simulated alarm criteria on alarm conditions that are detected. For example, the reporting module can analyze the change, if any, in the number of detected alarm conditions using the new simulated alarm criteria. This information can be provided for each patient and/or for the combined group of patients, for example. In addition, the reporting module can analyze differences in the timing at which alarm conditions were detected. Generally speaking, the reporting module can analyze any change in the number, type, timing, duration, etc. of alarm conditions that are detected when using the second alarm criteria as compared to the alarm conditions detected using the first alarm criteria that were applied at the time of monitoring.

At block 3112, the reporting module can output a report that identifies, explains, summarizes, or otherwise bears upon the effect of the simulated alarm criteria. This report can be beneficial to, for example, hospital administrators in determining whether any changes to the alarm criteria used by, for example, the bedside patient monitors are warranted. For example, as described herein, in some circumstances the alarm criteria could be changed so as to reduce the number of false positives that are detected. The reporting module enhances the ability of hospital administrators to make such decisions because it can provide information about the effect that such changes would have had if they had been previously implemented. Generally speaking, hospital administrators will have the final responsibility for determining whether changes to the alarm criteria can be safely made in order to, for example, reduce false positives without unacceptably increasing false negatives.

FIG. 32 illustrates an example report with a table 3200 showing how simulated alarm criteria affect alarm detection events. The table 3200 includes row entries for five different simulated alarm criteria, though any number of new alarm criteria could be simulated. The table 3200 includes column entries for the number of alarms detected using each simulated alarm criteria. The number of alarms could be broken down, for example, according to patient, or listed as a total sum of alarms detected for all of the patients for whom physiological parameter data was collected.

The table 3200 also includes column entries for the change in the number of alarms that were detected using each of the simulated alarm criteria as compared to the number of alarms that were detected using the actual alarm criteria applied at the time of collection of the physiological parameter data. This change could be indicated as the difference in the number of alarms, the percent difference, etc.

Many other types of information and information formats exist for reporting the effect of the simulated alarm criteria. FIG. 32 illustrates only an example report that could be generated by the reporting module based upon the simulated alarm criteria. It should be understood that such reports could include a wide variety of information relating to the impact of the simulated alarm criteria to help hospital administrators make a decision as to whether changes to alarm criteria should be made. In addition, such reports can be presented in a wide variety of formats, including tables, charts, graphs, lists, spreadsheets, etc.

Figure 33:
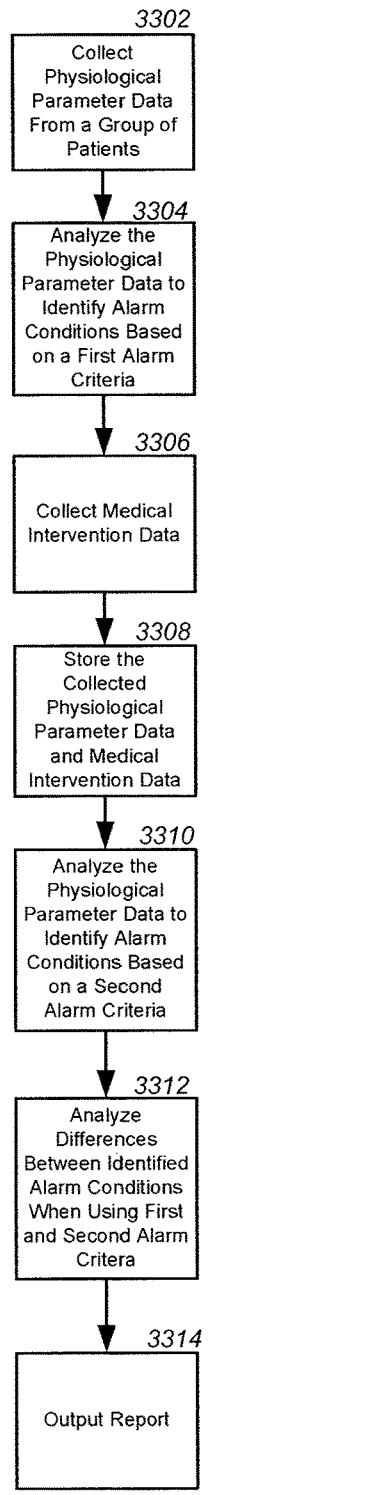
FIG. 33 is a flow chart that illustrates another method for determining the variation in identified alarm conditions that occur as a result of varying alarm criteria.

FIG. 33 is a flow chart that illustrates another method 3300 for determining the variation in identified alarm conditions that occur as a result of varying alarm criteria. The method 3300 is similar to the method 3100 illustrated in FIG. 31, however, the method 3300 additionally involves determinations of, for example, the expected effect of simulated alarm limits on false positive alarms and false negative alarms.

The method 3300 can proceed through blocks 3302 and 3304 as described above with respect to the method 3100 and blocks 3102, 3104 illustrated in FIG. 31. At block 3306, however, the method 3300 further includes collection of medical intervention data. The medical intervention data can include, for example, records of whether a patient required some type of medical intervention at any point in time while the physiological parameter was being monitored. Such medical interventions could include, for example, the administration of a drug, attention from a physician or nurse (e.g., non-routine attention), attention from a rapid response team, administration of a treatment or procedure, etc. The medical intervention data can also include any pertinent information about the medical intervention such as, for example, the type, the time, and the duration of the medical intervention, the medical cause that necessitated the intervention, relationship to detect alarm events, etc.

In some embodiments, the medical intervention data that is collected at block 3306 is used to determine which, if any, of the alarm conditions detected at block 3304 were false positive alarms and/or which were alarms that represented true indications of medical duress. Later, this information can be used, for example, to determine whether various simulated alarm criteria would have eliminated any identified false positive alarms or whether the simulated alarm criteria would have resulted in non-detection of any alarms that actually did indicate a need for medical intervention (e.g., resulting in a false negative). In addition, the medical intervention data can be used to identify false negatives and to determine whether simulated alarm criteria would have resulted in detection of such false negatives. This information can be analyzed and presented in a report to further aid hospital administrators in making a determination of whether to change alarm criteria used by patient monitoring devices based upon simulated alarm criteria, as described herein.

The medical intervention data can be obtained in a variety of ways. For example, medical intervention data can be recorded by clinicians as medical interventions become necessary. These records can then be manually imported into the central repository that also stores the collected physiological parameter data. Medical intervention data can be automatically imported into the central repository from the patient's electronic medical record stored in, for example, a Hospital Information System or a Clinical Information System. In some embodiments, the bedside patient monitoring devices can be configured so as to prompt clinicians to enter medical intervention data, for example, after an alarm is disabled. Other techniques for obtaining records of medical interventions can also be used.

If a record of a medical intervention that has been performed on behalf of the patient is, for example, temporally associated with the timing of a detected alarm condition (e.g., they are separated by some length of time less than a pre-determined threshold), this can be taken as a sign of an accurately detected alarm condition. For example, if a detected alarm condition is followed by a medical intervention relatively shortly thereafter, then it can be presumed that the alarm condition required medical attention. If, however, a record of a medical intervention that has been performed is not temporally associated with the timing of any detected alarm condition for that patient, then this can be an indication of a false negative since the medical condition that necessitated the intervention did not trigger an alarm. Later in the method 3300, after various new alarm criteria have been simulated, it can be determined whether such simulated criteria would have detected the false negative, or whether the new simulated criteria would have still detected the alarm condition that was accurately detected by the alarm criteria in place at the time of monitoring.

In some embodiments, medical intervention data can include an automated estimation of whether or not a medical intervention for a given patient has taken place. An estimation of whether or not a medical intervention was required after an alarm detection event can be automatically made based upon, for example, the length of time that a clinician spent with the patient after responding to an alarm event, or whether a physician came to check on the patient within some time limit of a detected alarm event. This information can be collected using the clinician proximity detection devices and systems described herein. For example, in some embodiments, a patient monitoring device can start a timer after an alarm detection event has occurred. If the presence of a physician (e.g., as identified by a clinician token, as described herein) is detected within some predetermined amount of time, then an estimation can be made that the physician visit was in response to the alarm event. As such, the physician visit can be identified as a medical intervention. Similarly, a patient monitoring device can track the amount of time that a clinician (e.g., a nurse) spends in proximity to the patient after silencing an alarm. If the amount of time with the patient exceeds a certain threshold, then it can be inferred that some type of medical intervention was necessary in response to the alarm event.

In addition, an estimate of whether or not medical intervention was required, for example, after an alarm event can be determined by analyzing the physiological parameter data collected for that patient. For example, the reporting module can analyze the trend values for the physiological parameter and determine whether the physiological parameter continued to worsen after the alarm event was detected. In some embodiments, the reporting module can analyze the trend data to determine whether the patient's condition, as indicated by the trend values of the physiological parameter, was worse 1 min. after the alarm detection event, whether it was worse 5 min. later, and/or whether it was worse 10 min. later. Different time limits can of course also be used. If such an analysis indicates that the patient's condition deteriorated after the alarm event was detected, then this can be taken as an indication that the alarm did in fact indicate that the patient was experiencing medical duress and that the alarm was not a false positive.

As just described, the medical intervention data used in the method 3300 can come from actual records of medical interventions that occurred. Alternatively, or additionally, the medical intervention data used in the method 3300 can be estimated based upon factors such as, for example, the amount of time clinicians spent with the patient in the wake of a detected alarm event or the behavior of the physiological parameter within some relevant time after a detected alarm event. Other factors and methods for estimating the occurrence of a medical intervention can also be used. While medical intervention data that results from actual clinician records may be more accurate and reliable, some such occurrences of medical interventions may go unreported. Estimated medical intervention data can be useful since the reliance upon clinicians to maintain accurate records is reduced, though the estimates may be somewhat less reliable than actual clinician records.

At block 3308, the collected physiological parameter data and the medical intervention data can be stored in, for example, the central repository (e.g., the round-robin database 722) for later analysis by the reporting module. The reporting module can include logic used for correlating the collected medical intervention data with the detected alarm events. For example, the logic can include rules or criteria for determining whether or not a given medical intervention for a patient was related to an alarm condition experienced by that patient. For example, in the case of medical intervention data obtained from actual clinician records, a particular medical intervention for a patient can be correlated with a detected alarm event for that patient if the medical intervention and the alarm event occurred within a certain amount of time of one another. Other methods are also possible for matching medical intervention data with corresponding detected alarm events that were possibly related to the medical intervention. For example, such a correlation can be based upon the type of medical intervention that was performed and the type of physiological parameter for which monitoring data has been obtained. Some medical interventions may be viewed as being particularly likely to be related to a specific physiological parameter. In such cases, the reporting module logic may be configured to make it more likely that such a medical intervention will be marked as being correlated with alarm events triggered by that physiological parameter.

At block 3310, the reporting module analyzes the physiological parameter data using second alarm criteria, for example, as described with respect to FIG. 31 (e.g., block 3108). At block 3312, the reporting module can analyze any differences between those alarm conditions identified using the first alarm criteria versus those alarm conditions identified using simulated second alarm criteria. For example, after determining the alarm conditions that would have been detected by the second alarm criteria, the reporting module can determine how many of the true alarm conditions that were correctly identified at the actual time of monitoring using the first alarm criteria would have still been detected if the simulated alarm criteria had instead been implemented. It is desirable that such true alarm conditions still be detected so as to avoid increasing the number of false negatives. Accordingly, information regarding the number of true alarm conditions that would go undetected using a given simulated alarm criteria can be provided to hospital administrators to aid in determining whether a proposed change to the alarm criteria should be adopted.

In addition, the reporting module can analyze the effect of the simulated alarm criteria on any false negatives that were identified based on medical intervention data. In some embodiments, the reporting module determines whether the simulated alarm criteria would have detected any false negatives that were not identified by the first alarm criteria actually used by the patient monitoring devices. This can be done, for example, by executing logic designed to determine whether any alarm conditions detected using the simulated alarm criteria are temporally correlated with a previously-identified false negative event. If, for example, an alarm condition identified by the simulated alarm criteria precedes the timing of the identified false negative by some period of time less than a given threshold, then this can be taken as an indication that the alarm condition would have been an indicator of the false negative. Other logical tests can also be applied to correlate alarm conditions detected using the simulated alarm criteria with false negatives that have been identified based on medical intervention data.

At block 3314, the reporting module outputs a report that identifies, explains, summarizes, or otherwise bears upon the effect of the simulated alarm criteria. In some embodiments, the report can provide an indication of the effect that the simulated alarm criteria would be expected to have on not only the number of detected alarm events but also the number, percentage, proportion, etc. of, for example, previously undetected false negatives that may have been detected using the simulated alarm criteria. The report can also include an indication of, for example, the number, percentage, proportion, etc. of actual alarm conditions that were correctly identified using the first alarm criteria but may not have been identified using the second alarm criteria. The report can also include other information as well.

FIG. 34 illustrates an example report with a table 3400 showing how simulated alarm criteria affect the total number of alarm detection events as well as how the simulated alarm criteria affect, for example, false negatives and false positives. The table 3400 is similar to the table 3200 illustrated in FIG. 32, and includes row entries for five different simulated alarm criteria. The table 3400 includes column entries for the number of alarms detected using each simulated alarm criteria. The table 3200 also includes column entries for the change in the number of alarms that were detected using each of the simulated alarm criteria as compared to the number of alarms that were detected using the actual alarm criteria applied at the time of collection of the physiological parameter data.

In addition, the table 3400 includes column entries for the estimated number or percentage of false negatives that previously went undetected but would have been detected using a particular simulated alarm criteria. The table 3400 also includes column entries for the estimated number or percentage of true alarm conditions that were correctly identified using the first alarm criteria but would not have been identified using a particular simulated alarm criteria (i.e., new false negatives resulting from the simulated alarm criteria). These values can be determined or estimated by the reporting module, as described herein. The table 3400 could also include information regarding change in false positives, for example, the number of false positives that were detected by the first alarm criteria that would not have been detected by the simulated alarm criteria, or vice versa.

Again, FIG. 34 illustrates only an example report that could be generated by the reporting module based upon the simulated alarm criteria. It should be understood that such reports could include a wide variety of information to help hospital administrators make a decision as to whether changes to alarm criteria should be made. In addition, such reports can be presented in a wide variety of formats, including tables, charts, graphs, lists, spreadsheets, etc.

In addition to simulating alarm criteria, as described herein, the reporting module can also simulate the effect of other configuration changes in the bedside patient monitoring devices and/or a central patient monitoring station. For example, the reporting module can simulate the effect of different alarm notification delay times. As discussed herein, in some embodiments, when an alarm condition is detected, bedside patient monitors may be configured to wait until a predetermined alarm notification delay time has elapsed before transmitting notification of the alarm event to either a clinician or to a central monitoring station. In addition, the central monitoring station can likewise be configured to wait until a predetermined alarm notification delay time has elapsed before actually transmitting a notification of the detected alarm to a clinician by, for example, a page or other notification method.

These notification delay times can be useful in reducing the frequency of false positive alarm notification events when alarm conditions only transiently persist. Such transient alarm conditions may be triggered by, for example, sudden exertion or emotion. The reporting module can be useful in simulating the effect of differing notification delay times on alarm notification events. This can be useful because, for example, relatively slight modifications to the notification delay times could result in an important reduction in the number of false positives to which clinicians must respond.

Figure 35:
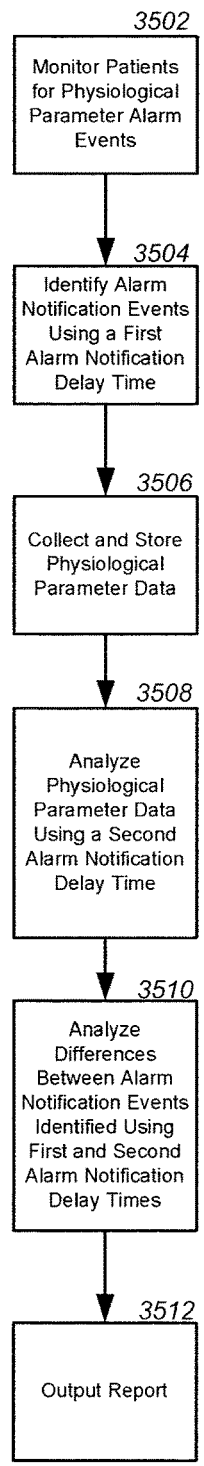
FIG. 35 is a flow chart that illustrates a method for determining the variation in alarm notification events that occurs as a result of varying alarm notification delay times.

FIG. 35 is a flow chart that illustrates a method 3500 for determining the variation in alarm notification events that occurs as a result of varying alarm notification delay times. The method 3500 begins at block 3502 where patients are monitored for physiological parameter alarm events, as described herein.

The method 3500 proceeds to block 3504 where alarm notification events are identified based upon a first alarm notification delay time. For example, an alarm notification event may be a notification by a bedside patient monitor to a central monitoring station of an alarm condition. In this case, the first alarm notification delay time could be measured as the elapsed time between when an alarm condition was detected at the bedside monitor and when notification of the alarm was sent to the central monitoring station. In addition, an alarm notification event may be a notification from a patient monitoring device to a clinician of an alarm condition. In this case, the first alarm notification delay time can be measured as the elapsed time between when an alarm condition was detected and when the clinician was notified.

At the initial time of monitoring, an algorithm, or algorithms, may be applied to the raw physiological signals, processed physiological signals, and/or computed physiological parameter values for detecting whether an alarm condition has persisted for the duration of the first alarm notification delay time. This can be done by, for example, each bedside patient monitor for each patient in the patient care domain. If an alarm condition persists for the duration of the first alarm notification delay time, then an alarm notification event can be recognized.

At block 3506, physiological parameter data is collected and stored at, for example, a central repository (e.g., the round-robin database 722), as described herein. At block 3508, the physiological parameter data is re-analyzed by, for example, the reporting module using a second alarm notification delay time that is different from the first alarm notification delay time. If, for example, the first alarm notification delay time used by the patient monitoring device at block 3504 were 5 sec., the physiological parameter data could be re-analyzed using an alarm notification delay time of, for example, 6 sec., or 7 sec., etc. Shorter delay times could also be simulated.

In some cases, if the alarm condition is only transient in nature, a relatively small lengthening of the alarm notification delay time could result in the alarm condition ceasing before an alarm notification event is generated. In this way, adjustment of the alarm notification delay time can potentially safely reduce the number of alarm notification events to which clinicians must respond. This can in turn increase the effectiveness of patient care by allowing clinicians to focus their time on attending to alarm events that are non-transient. Of course, any change to alarm notification delay times should generally be approved by hospital administrators or other responsible personnel to ensure that, for example, increases in the alarm notification delay times do not unacceptably put patients at risk by increasing the amount of elapsed time between a detected alarm and the arrival of a clinician.

The analysis of the previously-collected physiological parameter data by the reporting module can be used to simulate the effect of a new alarm notification delay time in a riskless manner since patients can still be monitored at, for example, blocks 3502, 3504 using a delay time that has already been accepted and validated. This ability to simulate the effect that new alarm notification delay times would have, without necessarily actually implementing them, is advantageous to hospitals and other patient care facilities as a means of adjusting alarm notification delay times to be specifically adapted for that particular hospital or patient care facility. As described herein with respect to alarm criteria, a change in the alarm notification delay times may result in significantly fewer alarm notification events without necessarily increasing the risk to patients.

At block 3510, the reporting module can analyze differences between clinician notification events that are detected using the first alarm notification delay time as compared to those that are detected using the second alarm notification delay time. For example, the reporting module may determine whether the total number of alarm notification events decreases or increases, and by how much, in response to a change in the alarm notification delay time. This information can be presented to hospital administrators in the form of tables, charts, spreadsheets, etc. to assist them in determining whether a change in the alarm notification delay times implemented by the patient monitoring devices would be advantageous.

Clinician response time data can also be collected and stored for analysis by the reporting module. Clinician response time can be measured as, for example, the elapsed time between when a clinician is notified of an alarm condition and when the clinician arrives at the patient's room to shutoff the alarm and check the patient's status. This elapsed time can be measured by, for example, the bedside patient monitoring devices and transmitted to the central repository of data. Clinician response times can be stored for each clinician and/or for a group of clinicians as a whole. As a result, the reporting module can output information regarding, for example, the maximum, minimum, and average response times for each clinician, and/or for a group of clinicians as a whole. This data may be useful to hospital administrators as an indicator of the performance of an individual clinician, or a group of clinicians, in responding to monitoring alarms in a prompt manner.

Display Features

Figure 36A:
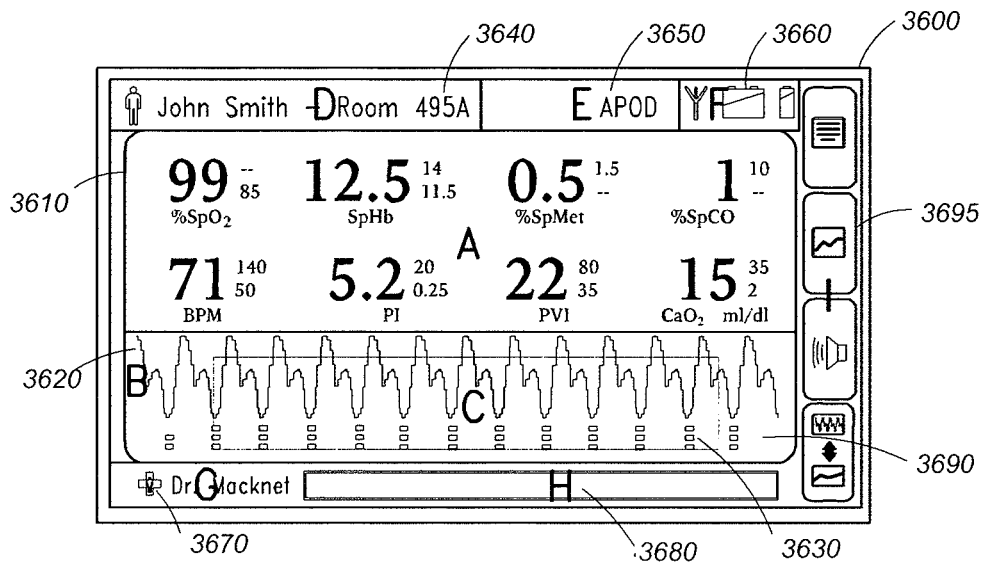
Figure 36B:
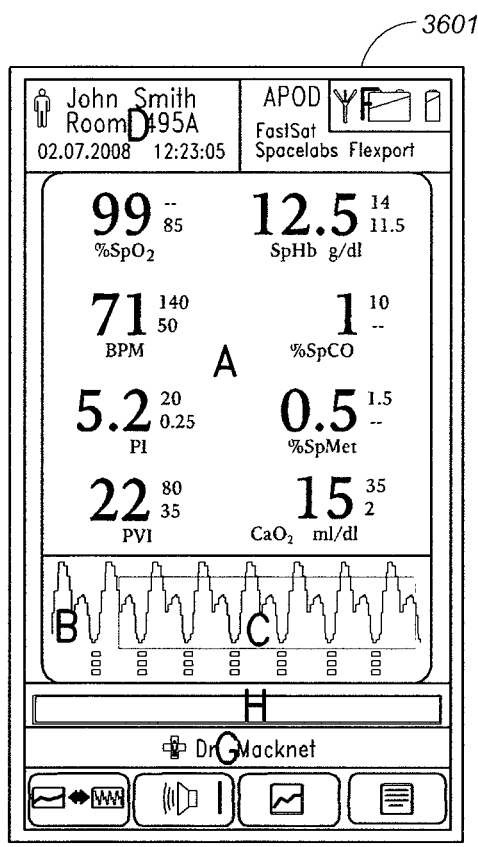

FIGS. 36A-B illustrate displays having layout zones including zones for parameters 3610, a plethysmograph 3620, a prompt window 3630, patient information 3640, monitor settings 3650, monitor status 3660, user profiles 3670, a parameter well 3680, pulse-to-pulse signal quality bars 3690 and soft key menus 3695. Advantageously, each zone dynamically scales information for readability of parameters most important to the proximate user. Also, the prompt window 3630 utilizes layered messaging that temporarily overwrites a less critical portion of the display. Further, the parameter well 3680 contains parameters that the proximate user has chosen to minimize until they alarm. These and other display efficiency features are described below.

FIGS. 37A-F illustrate displays that vary layouts and font sizes according to the number of installed parameters. Horizontal and vertical display formats are shown for displaying eight parameters (FIG. 37A); seven parameters (FIG. 37B); six parameters (FIG. 37C); five parameters (FIG. 37D); four parameters (FIG. 37E); and three parameters (FIG. 37F). Advantageously, font size increases with fewer installed parameters. Further, parameter layout varies according to the number of rows and spacing according to the number of installed parameters. Also, the plethysmograph display increases in size with few installed parameters. In addition, font size of text information scales according to the amount of information displayed, e.g. patient name is displayed in a smaller font when date and time information is added.

Figure 38A:
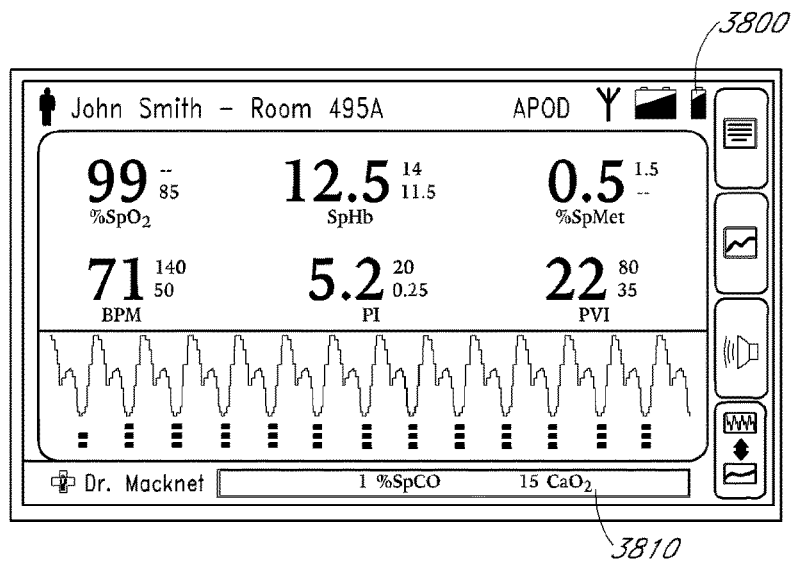
Figure 38B:
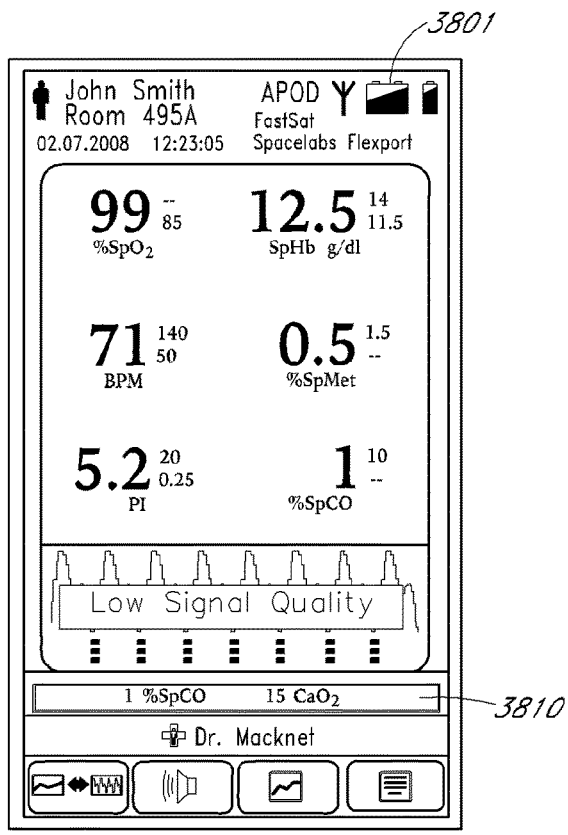

FIGS. 38A-B illustrate displays 3800 having parameter wells 3810. In particular, parameter values are displayed in either a main display portion or in a parameter well. Through a menu selection or by user profile activated by user proximity, a parameter is minimized to the parameter well. Advantageously, one or more parameters in the parameter well are displayed in a relatively small font. However, when a minimized parameter alarms, it is removed from the parameter well and return in a relatively larger font to the main display.

Figure 39A:
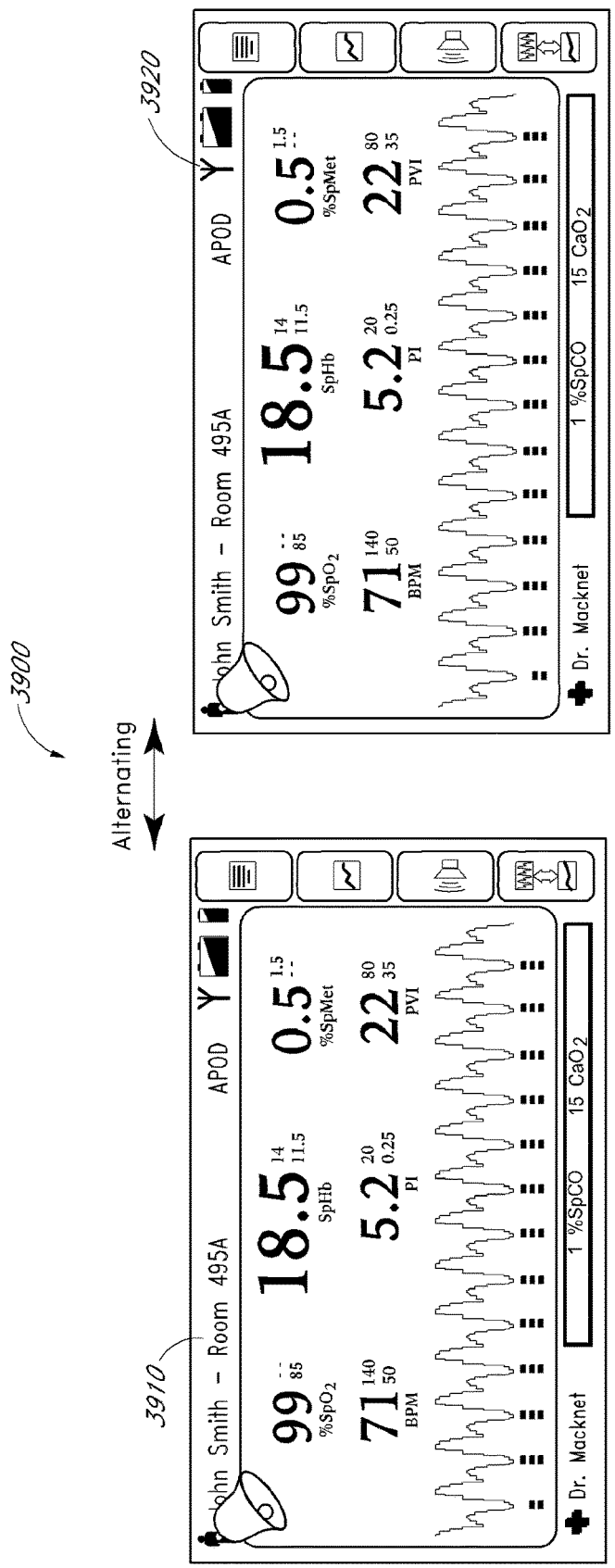
Figure 39B:
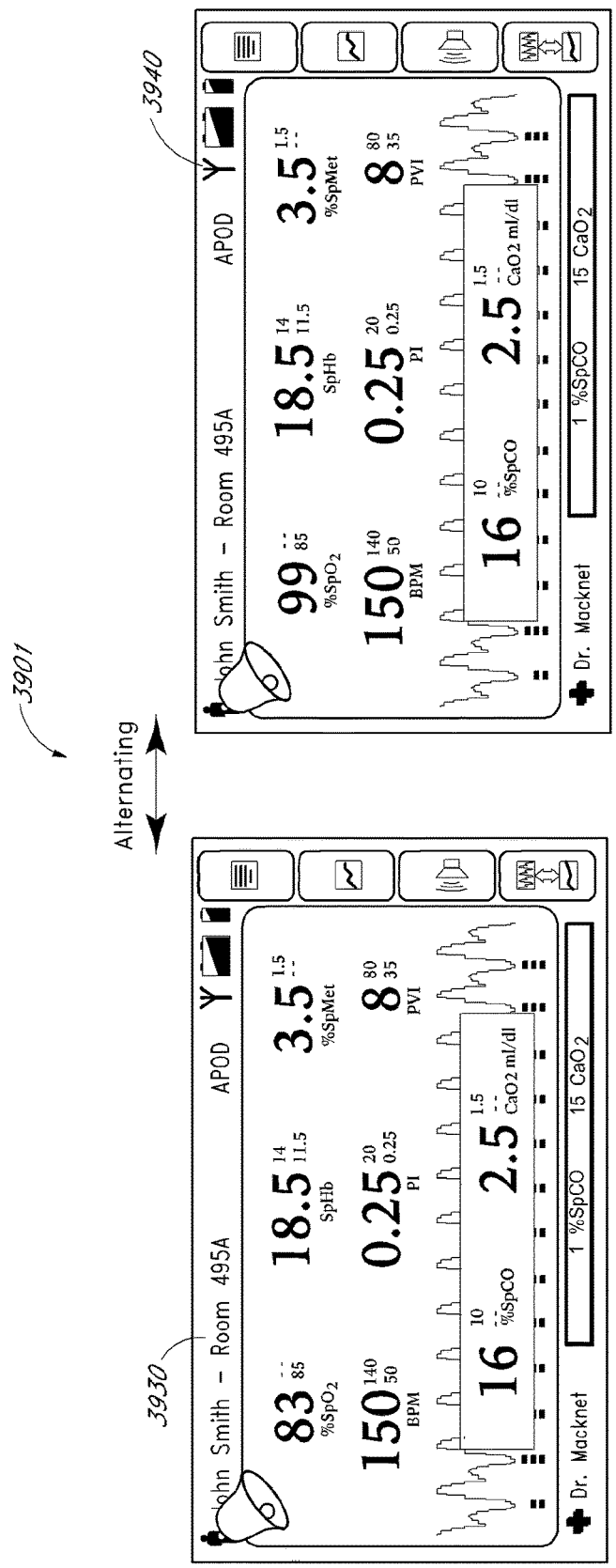
Figure 40A:
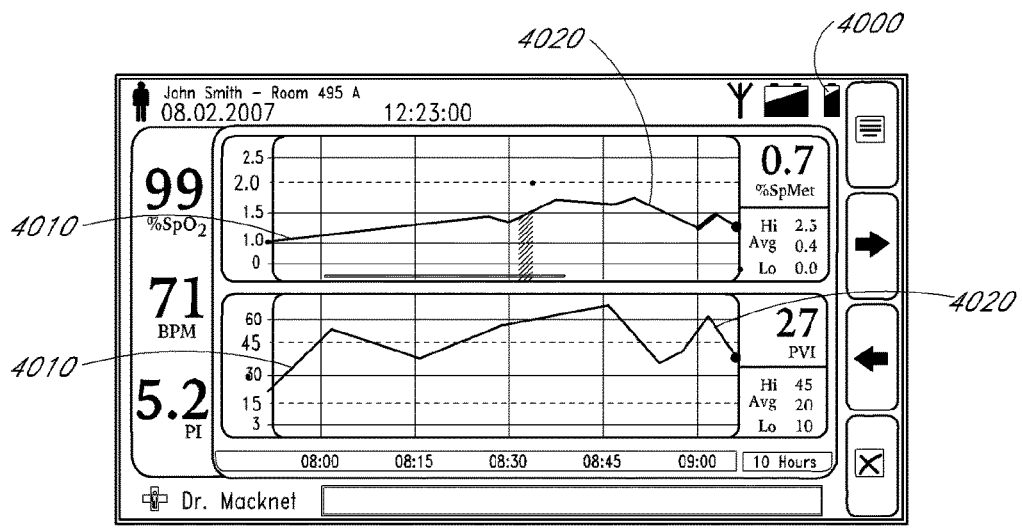
Figure 40B:
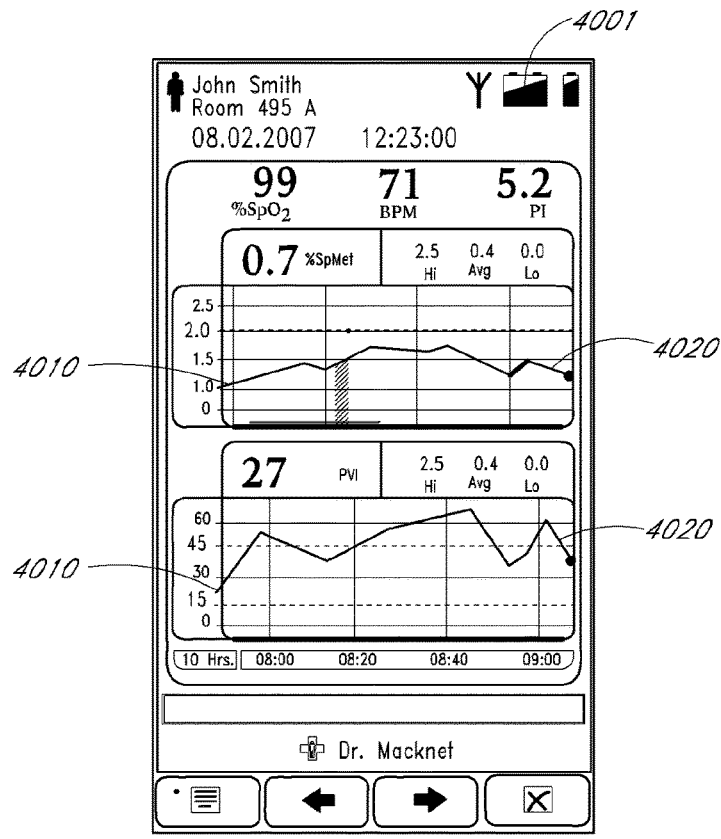

FIGS. 39A-B illustrate enlarged parameter displays 3900, 3901 that increase the font size of alarming parameters. In normal conditions, all parameters are display in a same sized font. When an alarm occurs, the violating parameter's actual value and limit values are displayed in a larger font and also blink to draw attention to the violation. In another embodiment, where all parameters are displayed at or near the maximum-sized font, then the alarming parameter will increase only slightly in size while all other parameters are reduced in size. Thus, the effect is an appearance that the alarming parameter is enlarged. In an embodiment, if either a single parameter alarms (FIG. 39A) or all parameters alarm (FIG. 39B), the background color also blinks at the same frequency so as to contrast with the blinking font, such as between a red background color and a soft red background color.

Figure 41:
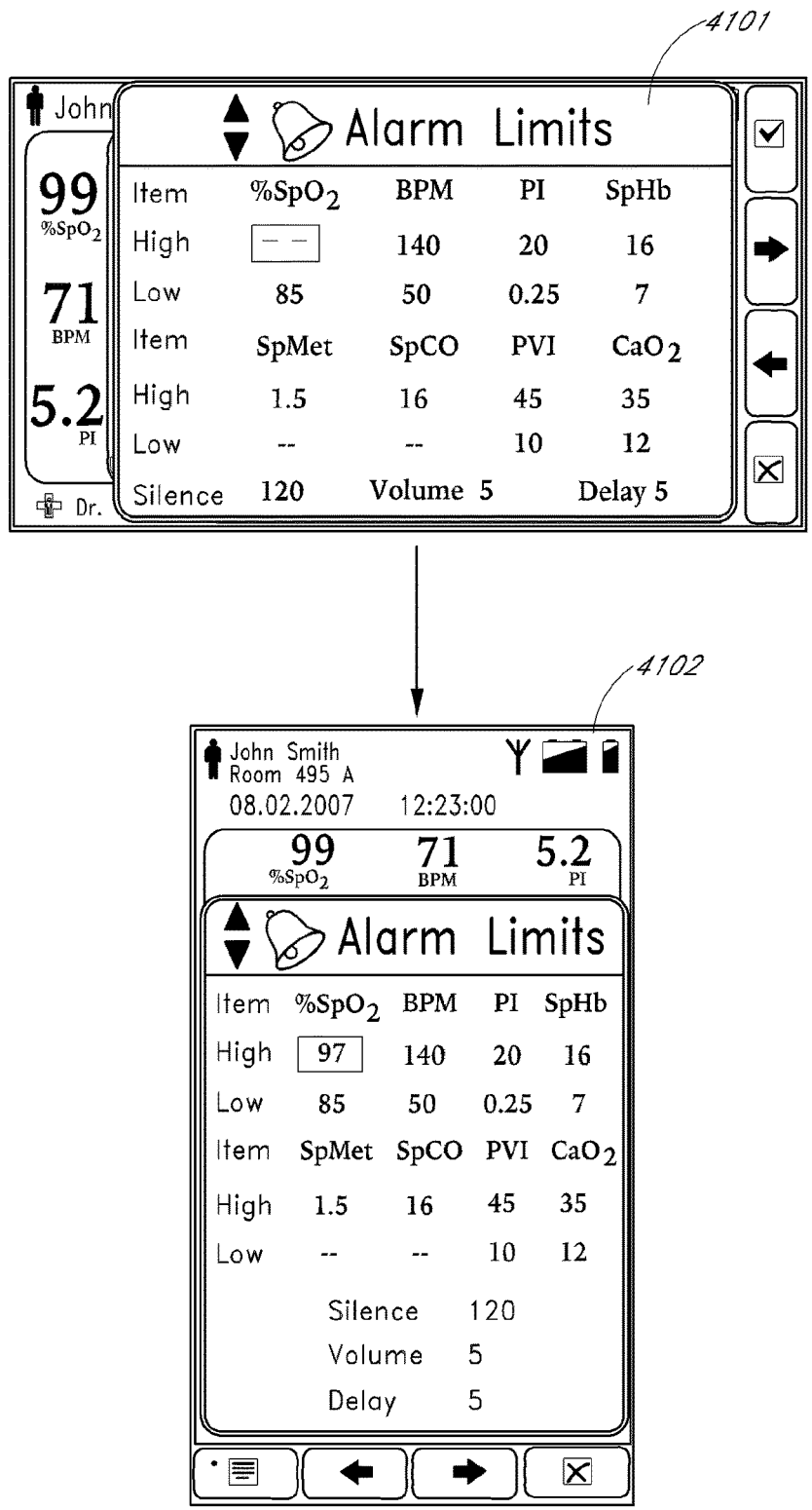

FIGS. 40-43 illustrate additional display embodiments having various advantageous features. FIGS. 40A-B illustrate trend displays 4000 having colored alarm zones 4010 so that a user can readily identify the historical severity of a patient condition that triggers an alarm. FIG. 41 illustrate displays that invert arrow keys to match the cursor. FIGS. 43A-B illustrate trend displays and corresponding set-up screens.

Figure 42:
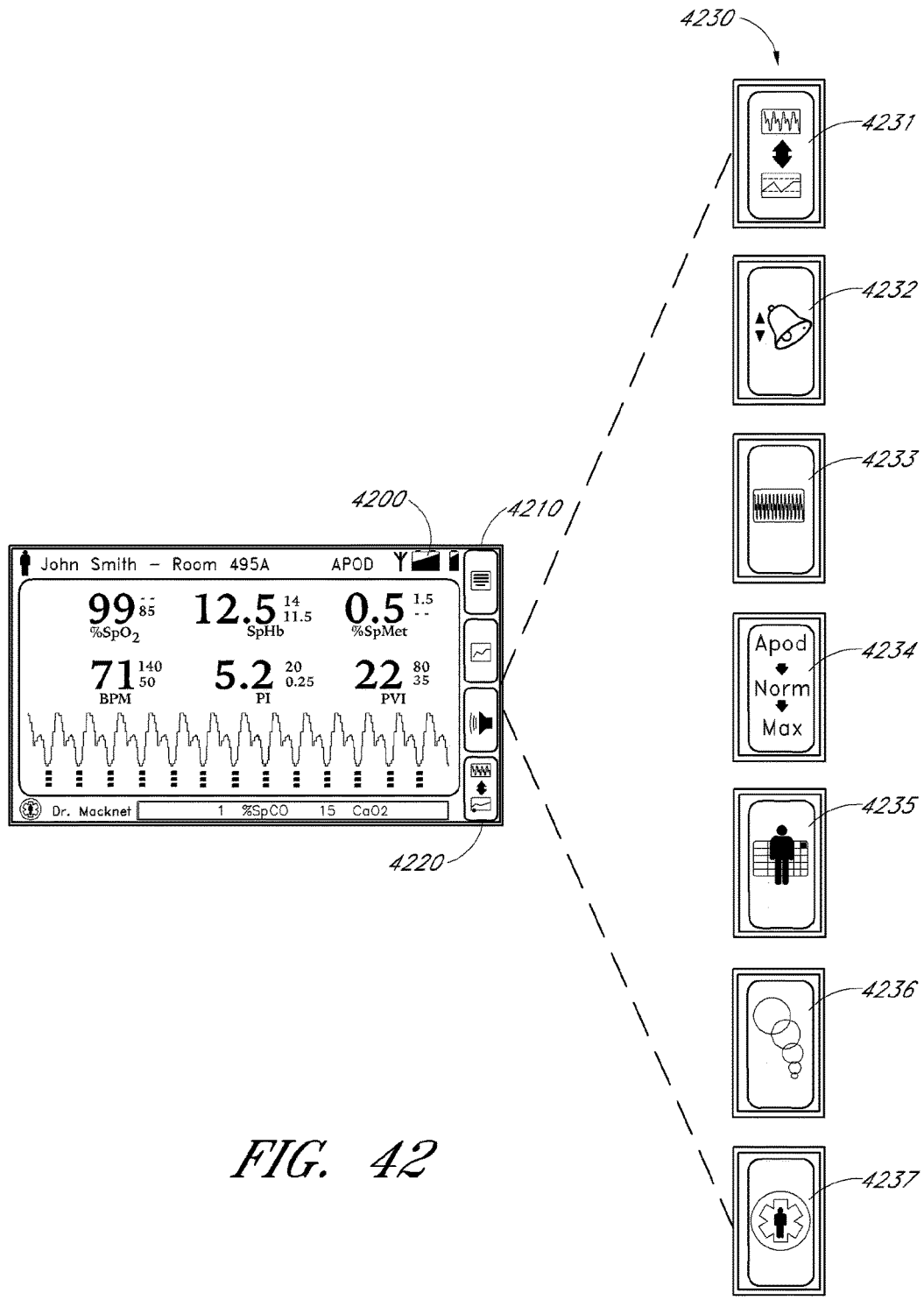
Figure 43A:
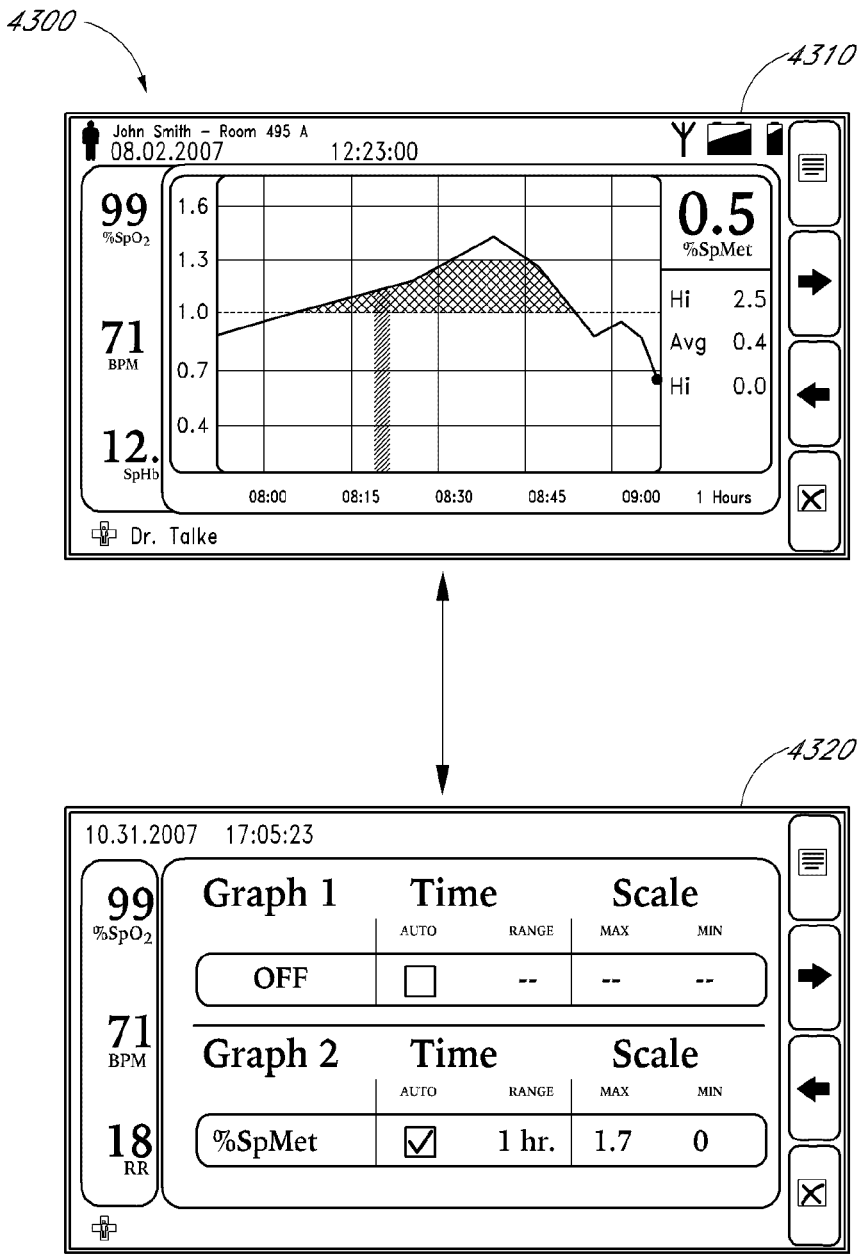

FIG. 42 illustrates a display having user-selectable jump-screens. In particular, through a menu option choice, a user can choose one of multiple jump screens, such as the seven choices shown, that they can access from the home page. In an embodiment, the default behavior for the button is the Trend-Toggle button 4231. Other buttons are Alarm Limits 4232, Compressed Waveform View or PI & PVI trend overlay 4233, Mode Sensitivity 4234, Patient Assess 4235, Parameter Detail Toggle 4236 and User Profile Login 4237.

Information and signals described herein can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

Depending on the embodiment, certain acts, events, or functions of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, conventional processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, or variables.

In addition, although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

What is claimed is:

1. A method of reducing nuisance alarms for a physiological parameter by determining an alarm threshold optimized for a specific care unit, the care unit including a plurality of patients being monitored for the physiological parameter, the method comprising:
   in the care unit, electronically measuring patient specific physiological parameters for the plurality of patients using a plurality of patient monitors;
   electronically providing the patient specific physiological parameters to a threshold recommendation system;
   receiving at least one recommended parameter specific alarm threshold value, said value responsive to a number of alarms triggered by said patient specific physiological parameters at said at least one recommended parameter specific alarm threshold value;
   said at least one recommended parameter specific alarm threshold value calculated to reduce said number of alarms at said care center for said parameter by determining how many alarms are generated for each of a range of threshold values and choosing a threshold value from the range of threshold values that reduces a number of alarms; and
   programming at least one of said plurality of patient monitors with a threshold value incorporating information gained by said suggested threshold value.

2. The method of claim 1, wherein electronically measuring patient specific physiological parameters comprises receiving physiological parameter measurements from the plurality of patient monitors operated in the care unit and stored at a central repository.

3. The method of claim 2, wherein the physiological parameters comprises one or more of raw physiological signals, detected alarm events, or care provider indications of medical interventions.

4. The method of claim 1, wherein the method is repeated for different care units and the receiving the at least one recommendation comprises a different recommendation for at least two different care units.

5. The method of claim 1, wherein said at least one recommended parameter specific alarm threshold value is calculated to reduce said number of alarms at said care center for said parameter by determining how many alarms are generated for each of the range of threshold values based on differences in one or more of timing, number, type, or duration of alarm conditions and choosing the threshold value from the range of threshold values that reduces the number of alarms.

6. The method of claim 1, wherein said at least one recommended parameter specific alarm threshold value is calculated to reduce said number of alarms at said care center for said parameter by determining how many alarms are generated for each of the range of threshold values based on differences in an alarm delay time and choosing the threshold value from the range of threshold values that reduces the number of alarms.

7. The method of claim 1, wherein said at least one recommended parameter specific alarm threshold value is calculated to reduce said number of alarms at said care center for said parameter by determining how many alarms are generated for each of the range of threshold values at least in part by correlating temporally proximate medical interventions with alarm events to identify true alarms and distinguish false alarms and choosing the threshold value from the range of threshold values that reduces the number of alarms.

8. The method of claim 7, further comprising providing the medical intervention information to the threshold recommendation system.

9. The method of claim 7, wherein the medical intervention information is estimated based on care provider time spent with a patient.

10. The method of claim 9, wherein care provider time spent with the patient is estimated by one or more of a presence of clinician token, a number of consecutive alarm silences or a length of alarm silences.

11. The method of claim 9, wherein medical intervention information is estimated based on trend activity of the physiological parameter which is temporally proximate an alarm event.

12. The method of claim 11, wherein the trend activity indicative of a medical intervention comprises continued low or decreasing parameter values.

13. The method of claim 11, wherein the trend activity indicative of a medical intervention comprises continued low or decreasing parameter values.

14. The method of claim 1, wherein the care unit is one of a hospital or care facility.

15. The method of claim 1, wherein the recommended parameter specific alarm threshold is an inflection point on a graph of alarm limits vs number of alarms for the patient specific physiological parameters.

16. A method of determining an alarm threshold optimized for a specific patient care unit, the alarm threshold selected to reduce nuisance alarms for a physiological parameter in the care unit, the care unit including a plurality of patients being monitored for the physiological parameter, the method comprising:

accessing measurements of patient physiological parameters across the plurality of patients using a plurality of monitoring devices in the patient care unit;

using the measurements, determining a first number of alarms that would have been triggered at a first parameter alarm threshold;

using the measurements, determining a second number of alarms that would have been triggered at a second parameter alarm threshold different from the first threshold;

selecting one of the first and second alarm thresholds that if applied would reduce alarm activations; and recommending, to the patient care unit, use of a care unit specific alarm threshold responsive to the selected one of the first and second alarm thresholds.

17. The method of claim 16, wherein the measurements of patient physiological parameters comprises one or more of raw physiological signals, detected alarm events, or care provider indications of medical interventions.

18. The method of claim 16, wherein the method is repeated for different care units and the analyzing the physiological parameter measurements provides a different recommendation resulting from one or more differences of a type of monitoring equipment used, patient population, a type of medical care offered, or a type of medical procedures implemented for the different care units.

19. The method of claim 16, further comprising correlating temporally proximate medical interventions with alarm events to identify true alarms and distinguish false alarms.

20. The method of claim 19, wherein the medical intervention information is manually recorded by a care provider.

21. The method of claim 19, wherein the medical intervention information is estimated based on care provider time spent with a patient.

22. The method of claim 21, wherein care provider time spent with the patient is estimated by one or more of a presence of clinician token, a number of consecutive alarm silences or a length of alarm silences.

23. The method of claim 21, wherein medical intervention information is estimated based on trend activity of the physiological parameter which is temporally proximate an alarm event.

24. The method of claim 23, wherein the trend activity indicative of a medical intervention comprises continued low or decreasing parameter values.

25. The method of claim 23, wherein the trend activity indicative of a medical intervention comprises continued low or decreasing parameter values.

26. The method of claim 16, wherein the care unit is one of a hospital or care facility.

* * * * *